United States Patent
Leventis et al.

(10) Patent No.: US 9,593,225 B2
(45) Date of Patent: *Mar. 14, 2017

(54) MULTIFUNCTIONAL POROUS ARAMIDS (AEROGELS), FABRICATION THEREOF, AND CATALYTIC COMPOSITIONS DERIVED THEREFROM

(71) Applicant: The Curators of the University of Missouri, Columbia, MO (US)

(72) Inventors: Nicholas Leventis, Rola, MO (US); Chariklia Sotiriou-Leventis, Rolla, MO (US); Malik Adnan Saeed, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/969,650

(22) Filed: Dec. 15, 2015

(65) Prior Publication Data

US 2016/0102187 A1    Apr. 14, 2016

Related U.S. Application Data

(63) Continuation-in-part of application No. 14/529,823, filed on Oct. 31, 2014, now Pat. No. 9,260,581, which is a continuation-in-part of application No. 13/909,574, filed on Jun. 4, 2013, now Pat. No. 8,877,824.

(60) Provisional application No. 61/689,352, filed on Jun. 4, 2012.

(51) Int. Cl.

| | | |
|---|---|---|
| *C08J 9/00* | (2006.01) | |
| *C08J 9/28* | (2006.01) | |
| *C07C 209/36* | (2006.01) | |
| *C07C 45/38* | (2006.01) | |
| *C07C 67/10* | (2006.01) | |
| *C07C 2/86* | (2006.01) | |
| *B01J 37/08* | (2006.01) | |
| *B01J 37/03* | (2006.01) | |
| *B01J 23/52* | (2006.01) | |
| *B01J 23/42* | (2006.01) | |
| *B01J 23/44* | (2006.01) | |
| *B01J 35/10* | (2006.01) | |
| *B01J 13/00* | (2006.01) | |
| *B01J 27/22* | (2006.01) | |
| *C07C 67/343* | (2006.01) | |
| *C01B 31/00* | (2006.01) | |

(52) U.S. Cl.
CPC ............ *C08J 9/286* (2013.01); *B01J 13/0091* (2013.01); *B01J 23/42* (2013.01); *B01J 23/44* (2013.01); *B01J 23/52* (2013.01); *B01J 27/22* (2013.01); *B01J 35/10* (2013.01); *B01J 37/035* (2013.01); *B01J 37/086* (2013.01); *C01B 31/00* (2013.01); *C07C 2/861* (2013.01); *C07C 45/38* (2013.01); *C07C 67/10* (2013.01); *C07C 67/343* (2013.01); *C07C 209/36* (2013.01); *C07C 2527/20* (2013.01); *C07C 2531/28* (2013.01); *C08J 2201/0502* (2013.01); *C08J 2205/024* (2013.01); *C08J 2205/026* (2013.01); *C08J 2205/042* (2013.01); *C08J 2300/202* (2013.01); *C08J 2377/00* (2013.01); *C08J 2385/00* (2013.01)

(58) Field of Classification Search
CPC ................ C08J 9/286; C08J 2201/0502; C08J 2205/024; C08J 2300/202; C08J 2377/00; C08J 2385/00; B01J 13/0091; B01J 23/42; B01J 23/44; B01J 23/52; B01J 27/22; B01J 35/10; B01J 37/035; B01J 37/086; C01B 31/00; C07C 2/861; C07C 45/38; C07C 67/10; C07C 67/343; C07C 209/36; C07C 2527/20; C07C 2531/28
See application file for complete search history.

(56) References Cited

U.S. PATENT DOCUMENTS 9,260,581 B2 * 2/2016 Leventis et al. ..... B01J 13/0091
2014/0128488 A1    5/2014 Lotti et al.

* cited by examiner

*Primary Examiner* — Nathan M Nutter
(74) *Attorney, Agent, or Firm* — C. John Brannon; Brannon Sowers & Cracraft PC

(57) ABSTRACT

The present disclosure provides a series of new and improved porous polyamide aerogels derived from multifunctional aromatics that combine the high mechanical strength of aramids with the pore structure of aerogels. The polyamide aerogels have a hyperbranched structure, relatively low density, high porosity and may be derived from functionalized monomers having more aromatic groups than functional groups. The present disclosure also provides a new method for producing the porous polyamide aerogels by polymerizing an aromatic multifunctional carboxylic acid or a ferrocene multifunctional carboxylic acid with a polyfunctional aromatic isocyanate at moderate reaction conditions followed by drying with liquid $CO_2$. Also disclosed are various methods of use of these polyamide aerogels in a variety of applications, particularly in the generation of various precious metal catalysts. Thus, monolithic nanoporous carbon-supported Fe, Au, Pt, Pd, Co, Ni, Ru, and Rh catalysts are disclosed herein, which are derived by pyrolysis and transmetalation via galvanic replacement of ferrocene-based polyamide aerogels.

10 Claims, 46 Drawing Sheets

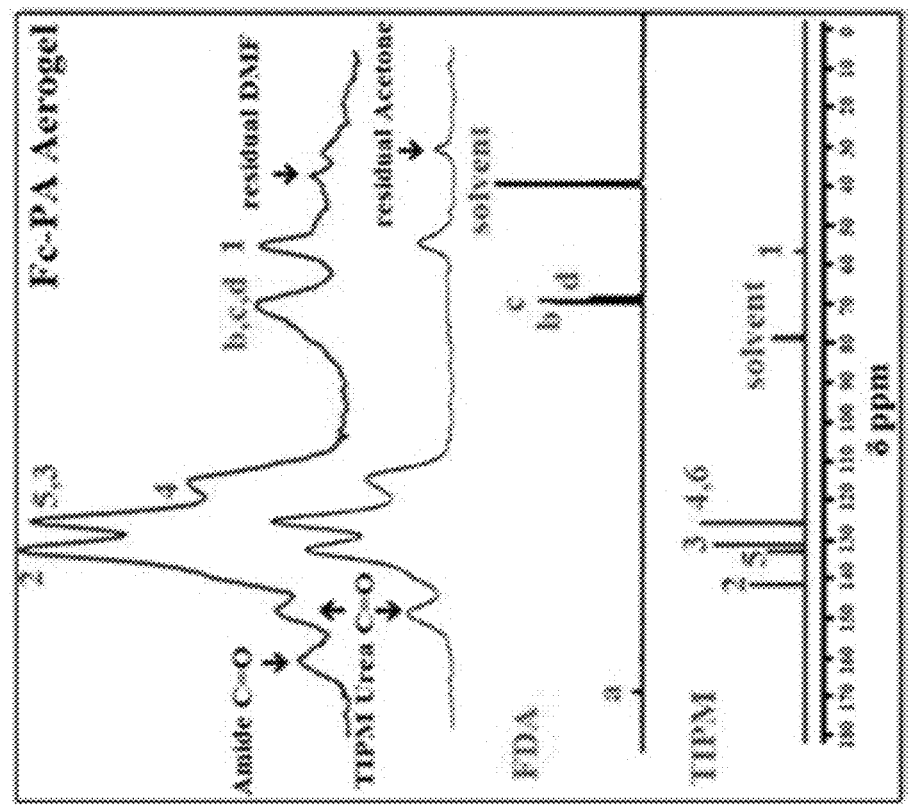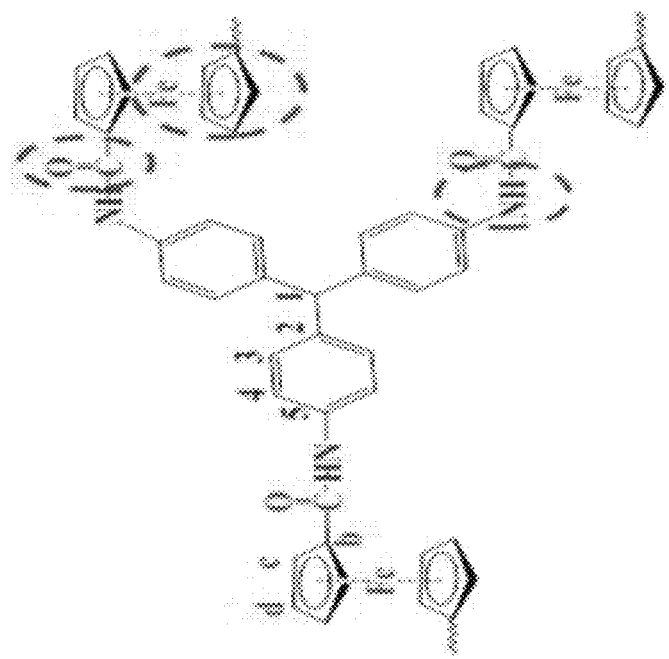
FIG. 9

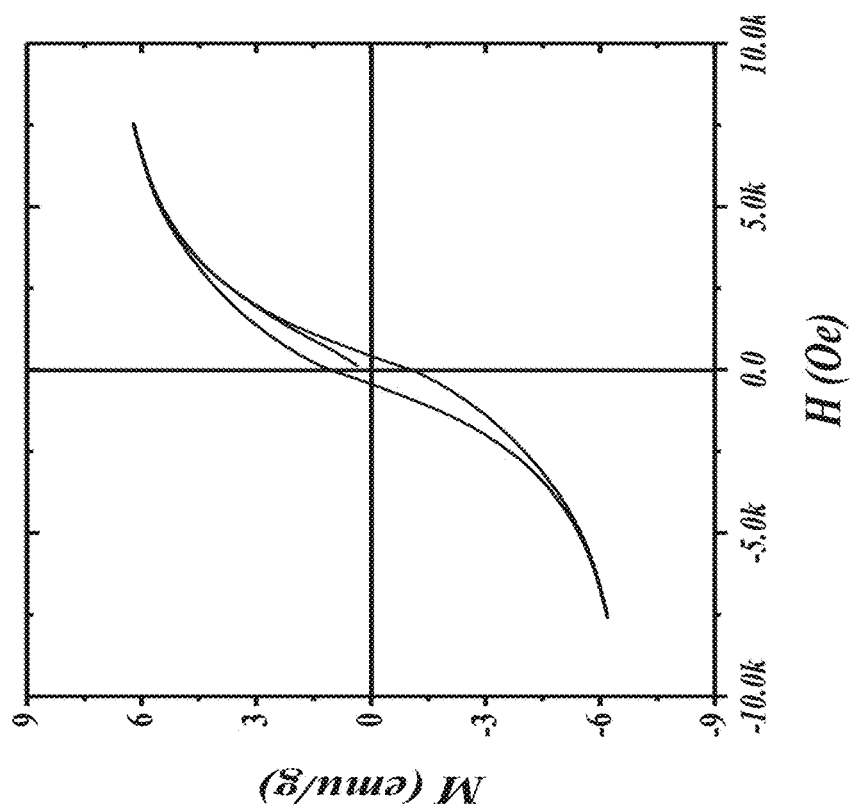
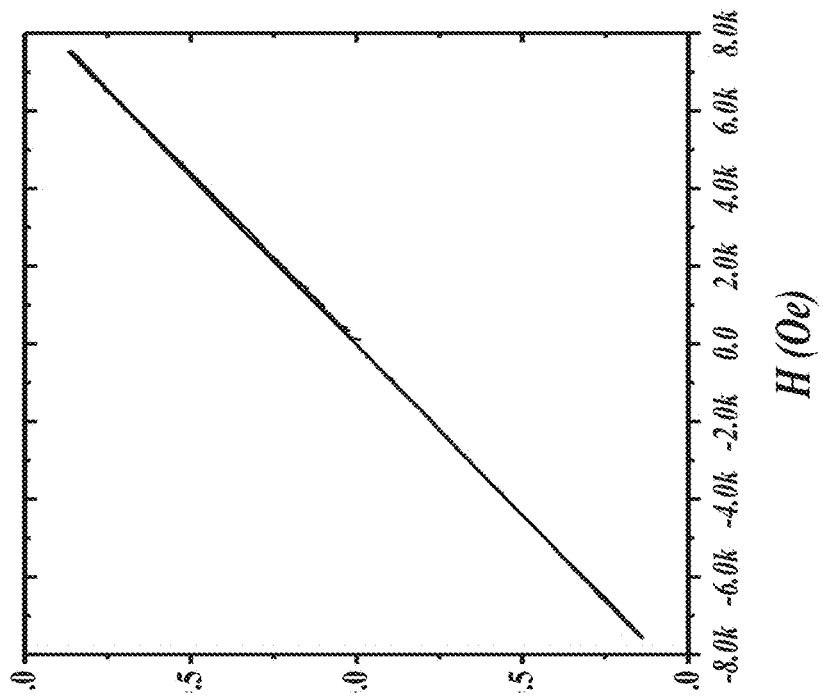
FIG. 18

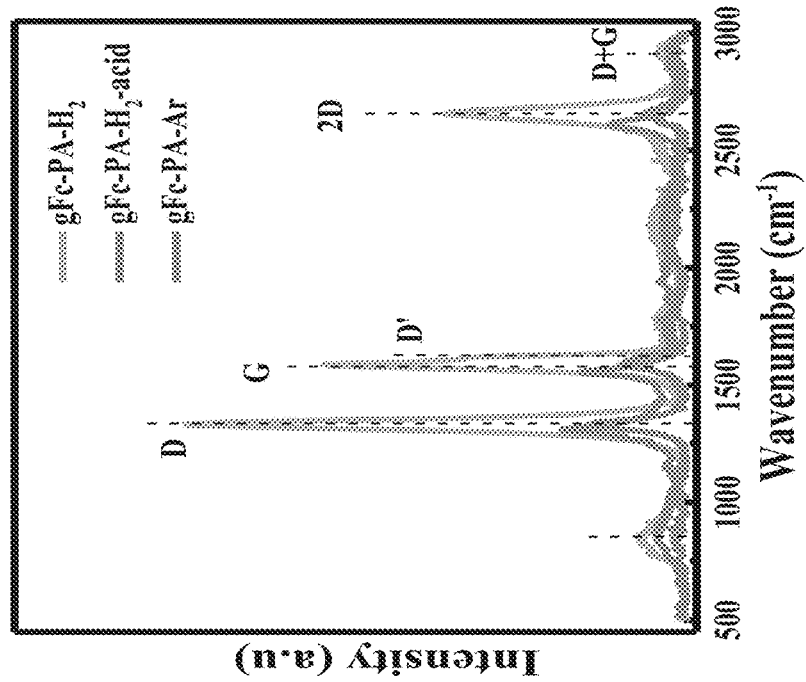
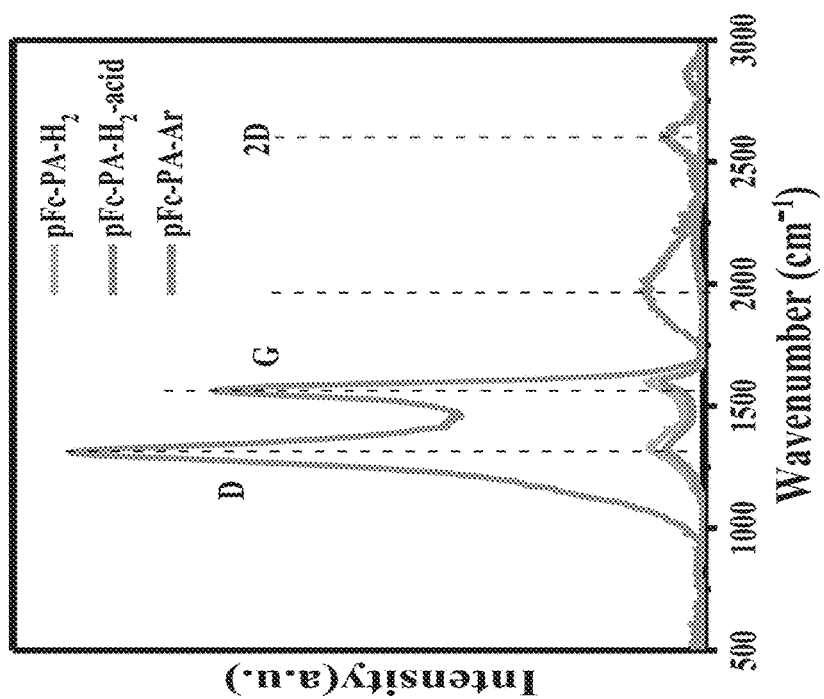
FIG. 21

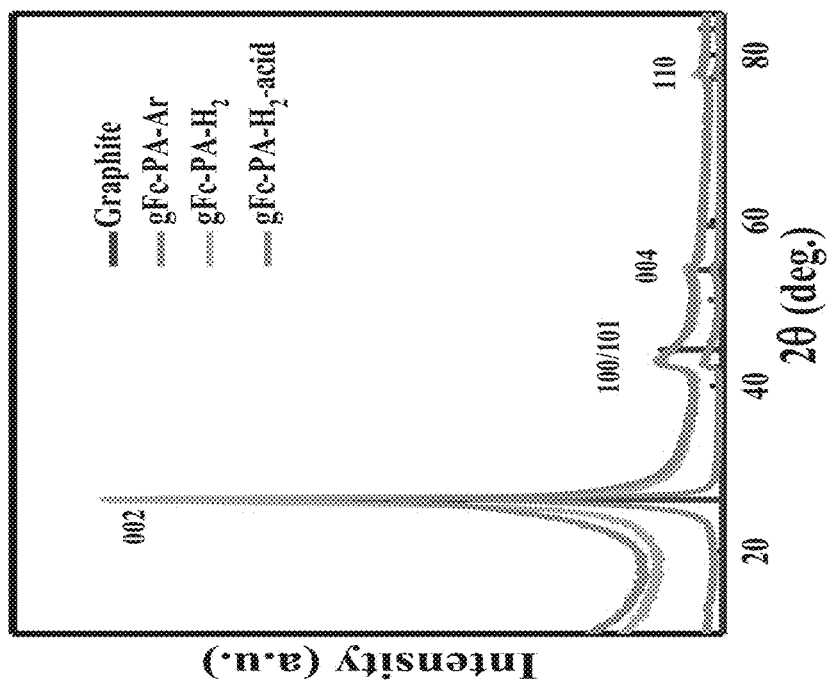
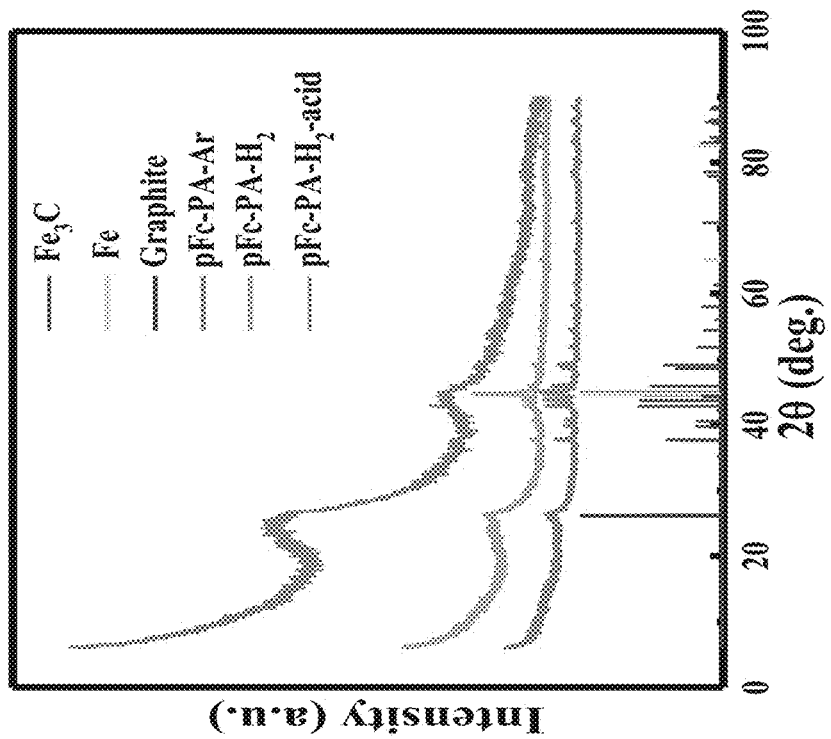
FIG. 22

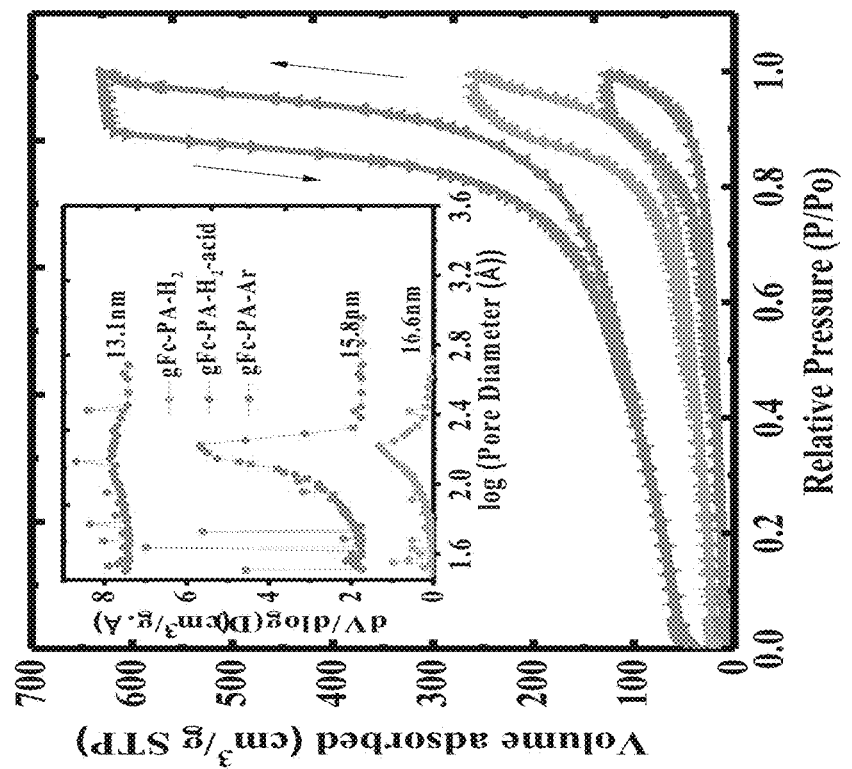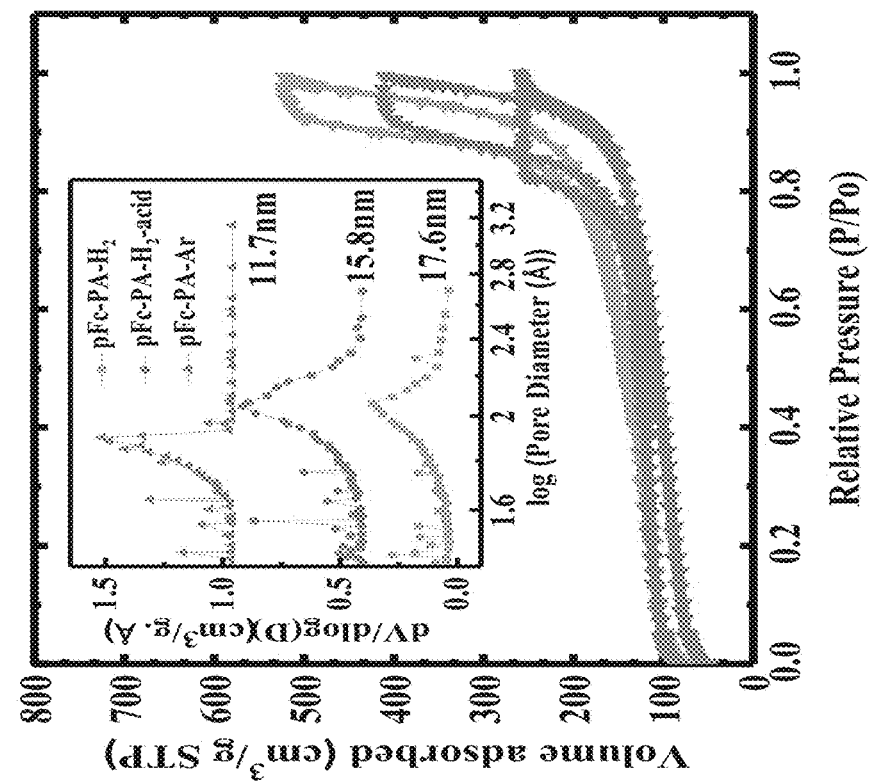
FIG. 23

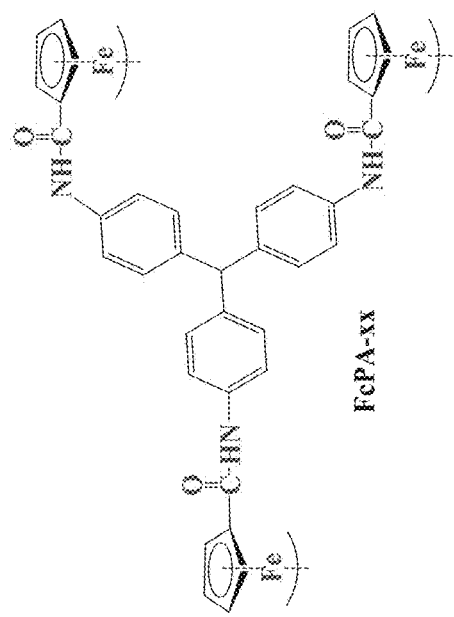
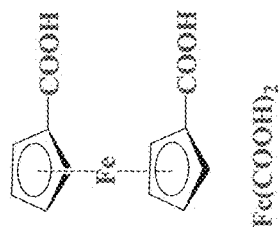
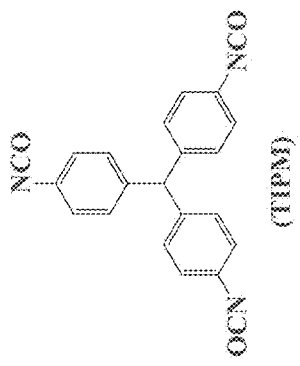
FIG. 31

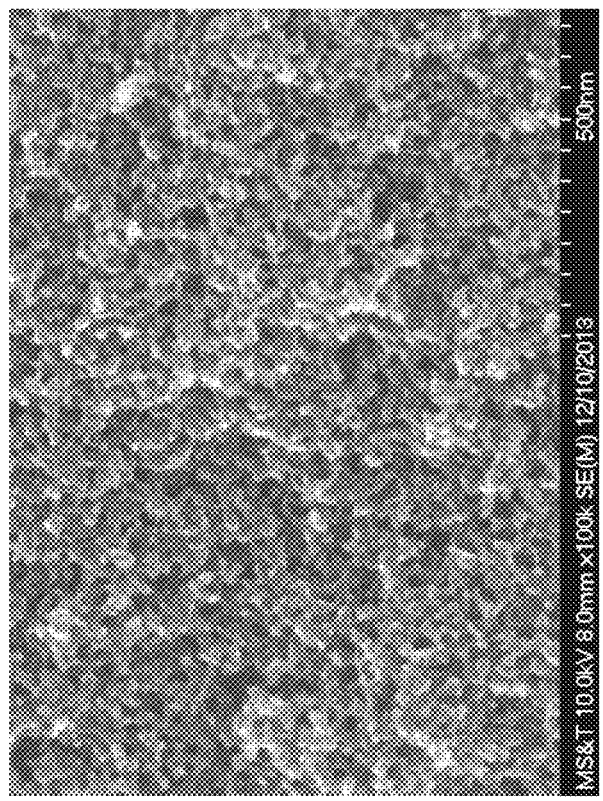
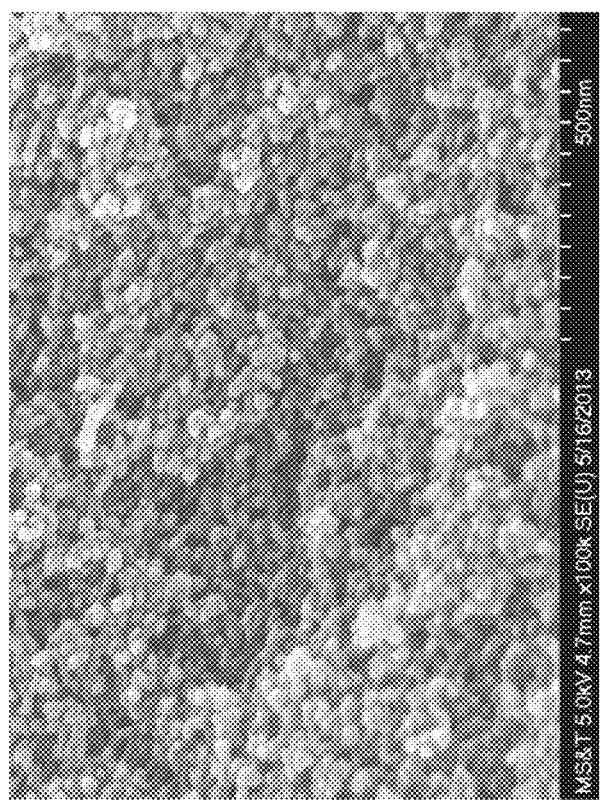
FIG. 33

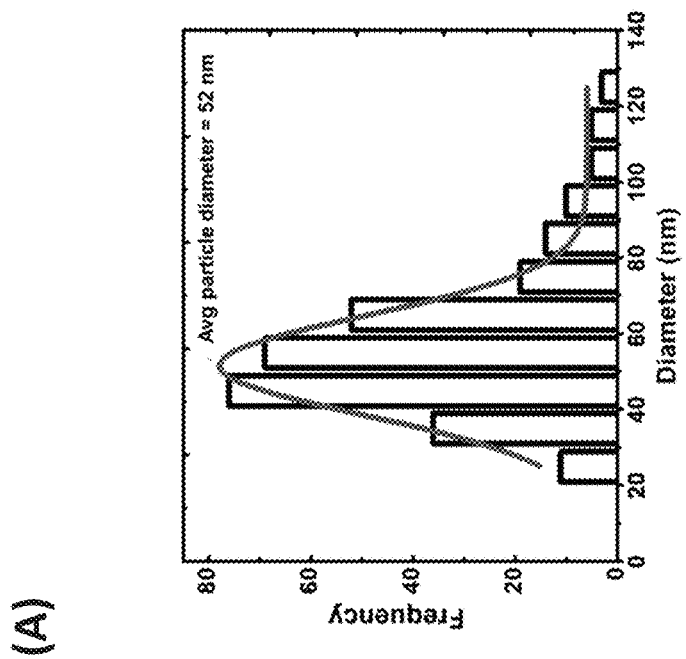
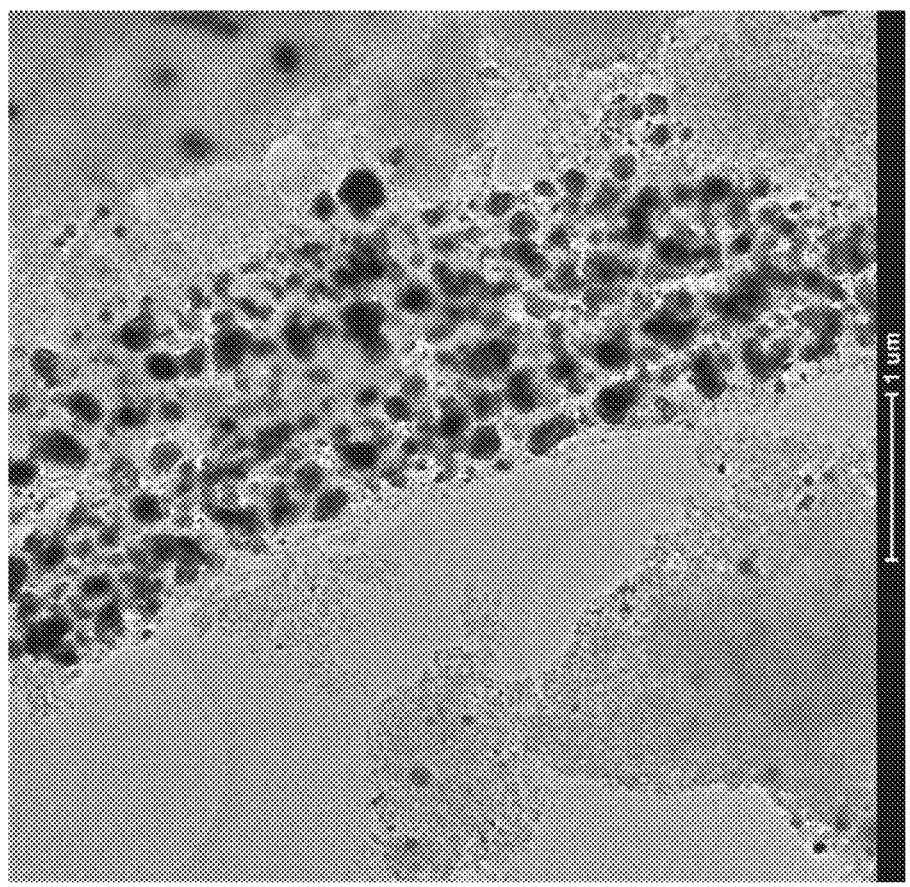
FIG. 36

(c)

MULTIFUNCTIONAL POROUS ARAMIDS (AEROGELS), FABRICATION THEREOF, AND CATALYTIC COMPOSITIONS DERIVED THEREFROM

CROSS-REFERENCE TO RELATED APPLICATIONS

This application is a continuation-in-part of and claims priority to co-pending U.S. patent application Ser. No. 14/529,823, filed on Oct. 31, 2014, which claims priority to U.S. patent application Ser. No. 13/909,574, filed on Jun. 4, 2013 (now issued U.S. Pat. No. 8,877,824), which claims the benefit of U.S. Provisional Application Ser. No. 61/689,352, filed Jun. 4, 2012, the disclosures of which are hereby incorporated by reference in their entirety.

GRANT STATEMENT

This invention was made with Government support under Grant No. CHE-0809562 awarded by the National Science Foundation and Grant No. W911NF-14-1-0369, W911NF-10-1-0476 and WF911NF-12-0029 awarded by the US Army Research Office. The U.S. Government has certain rights in the invention.

FIELD OF INVENTION

The present disclosure relates to Kevlar-type polyamide aerogels and more specifically to a new series of porous polyamide aerogels with increased mechanical strength and improved thermal and acoustic insulation.

BACKGROUND OF INVENTION

Polymeric cellular solids (foams) nearly eliminate convective heat transfer and thus combine low density with low thermal conductivity, both properties desirable for thermal insulation. Further reduction in the rate of heat transfer is realized with pore sizes below the mean free path of the pore-filling gas (68 nm for air at standard temperature-pressure (STP)). Such mesoporous (2-50 nm) materials include aerogels which typically exhibit poor mechanical properties. Systematic efforts to improve the mechanical properties of polymeric aerogels by crosslinking fibrous cellulose wet-gels with isocyanates have resulted in some improvement of mechanical properties, but have proven time-consuming and inefficient.

Therefore, what is needed are polymeric aerogels having sufficient strength and structural integrity without the need for post-gelation treatment and efficient methods for their production from readily available starting materials. This present disclosure addresses these needs.

Aerogels are porous materials and with small inter-connected pores. The three major types of aerogels are inorganic, organic, and carbon aerogels. Inorganic aerogels can be obtained by supercritical drying of highly cross-linked and transparent hydrogels synthesized by polycondensation of metal alkoxides. Silica aerogels are the most well known inorganic aerogels. Organic aerogels can be synthesized by supercritical drying of the gels obtained by the sol-gel polycondensation reaction of monomers such as, for example, resorcinol with formaldehyde, in aqueous solutions. Carbon aerogels can be obtained by pyrolyzing the organic aerogels at elevated temperatures. It is believed that carbon aerogels are the only electron conductive aerogels; therefore since their discovery, they have been suggested for use as electrodes for fuel cells or as super-capacitors because of their mesoporous structure.

Transition metals are induced in carbon aerogels with the goal of modifying structure, conductivity or catalytic activity, due to homogenous distribution of metal nano particles in the 3-D network of carbon. Thus, carbon supported metal aerogels may be potentially invaluable, as they have unique properties of metals as well as carbon aerogels. The metal in metal aerogel is of nano-size as a result of heat treatment; hence, as a consequence, the nanomaterials often exhibit properties atypical of their bulk metal. This may make them promising materials for applications in the preparation of electrodes, batteries, super capacitors, adsorbents, molecular sieves and catalysts, due to their easy preparation, good textural and chemical properties, in addition to their unique properties like high surface area, porosity and low density.

Conventionally, it has been reported that metal-doped carbon aerogels may be prepared by three main strategies. The first is the addition of the soluble metal precursor (metal salts) in the initial mixture. The second involves the use of a resorcinol derivative containing an ion exchange moiety that can be polymerized using sol-gel technique. The repeating unit of the organic polymer contains a binding site for metal ions to ensure a uniform dispersion of dopant metal. The third approach is to deposit the metal precursor on the organic or carbon aerogel by one of the various methods such as incipient wetness, wet impregnation, adsorption, sublimation and supercritical deposition. The drawback of first method has to do with the nature of salt, which effects sol-gel chemistry by changing the pH of initial solution, hence making it difficult to control pore texture of carbon matrix. A few publications have suggested that doped metal particles are anchored to the carbon structure of monoliths, where micropores act as nucleation sites for the metal nano particles. The anchoring of metal particles block micropores, hence the surface area of carbon aerogel decreases. The polymerization has been reported to be of two kinds: addition and condensation; the former is catalyzed by base and latter with acid, as the pH influences the molecular environment of the initial mixture polymerization, so it plays a major role in determining the structure and pore texture of resultant gel. The anions of salts used as either polymerization catalyst or ion exchange process, and even as metal precursors, also have been reported to have some effects on the sol-gel chemistry as well as on the resulting gel.

It has also been reported that transition metals and organometallic compounds are good catalysts to induce graphitization of carbon infrastructures during carbothermal process. The solid state pyrolysis is believed to be a convenient way to produce graphitic nano structures. It has been reported that the structure and morphology of the derived nano structured carbons may be tuned by changing the type of carbon source, metal catalyst and conditions of carbonization.

Ferrocene is an organometallic compound with two cyclopentadienyl moieties sandwiching Fe (II). There has been interest toward the incorporation of ferrocene into polymer backbone, due to the high stability, redox properties, electrical, conducting/semiconducting, magnetic, optical, catalytic, and elastomeric properties that can be used for a broad range of applications, such as, for example, electronic devices, formation of redox gels with charge transfer properties, modification of electrodes, and in medical applications for cancer treatment. This interest in ferrocene may be attributable in part to the rich chemistry of iron (II) centers and broad range of synthetic methods available for functionalization of the cyclopentadienyl ligands.

Conventionally, aromatic diamines have been known to be valuable building blocks for the preparation of polyamides that are used to produce desired alterations in the chemical nature of a macro chain. It has been reported that the properties of polyamides may be modified further by the addition of metal in their core structure. Inclusion of metals in the polymers may create the possibility of producing specialty materials with useful electrical, magnetic or catalytic properties, combined with thermal stability. Thus, inclusion of the ferrocene entity in the polyamide core structure along with flexible linkages may create the possibility of accessing materials that are superior to conventional polyamides with respect to their better balance of physicochemical properties.

Literature reports have described an ordered mesoporous carbon (i.e., well-ordered porous structure with uniform sized mesopores along with narrow pore size distribution in regular carbon frameworks) containing ferrocene derivative using furfuryl alcohol as the main carbon source; but its surface area was very low. There have also been other reports describing a route to make iron and iron oxide filled carbon nano tubes using ferrocene as precursor. The immobilization of ferrocene in layered or porous materials, motivated by the potential application of these materials in fields such as catalysis, sensors, optical devices, etc., has led to materials in which the chemical and physical properties of both the matrix and organometallic entities were often modified. The pyrolysis of ferrocene in argon atmosphere has been reported to produce a very large amount of carbon nano tubes. Another literature report has described the synthesis of ordered mesoporous carbon containing iron oxides by using ferrocene carboxylic acid as metal precursor and sucrose as main carbon precursor. Ordered mesoporous carbon (OMC) was compared with iron modified ordered mesoporous carbon (Fe-OMC) for their electroactivity for $H_2O_2$. The high performance of Fe-OMC is believed to be due to the electroactive substance (iron) being incorporated in its carbon framework, as well as to the increase in the surface area of Fe-OMC.

It has been reported that the precursors containing graphitic building blocks are potentially suitable for the synthesis of graphitized carbon materials. These precursors include polyaromatic hydrocarbons, aromatic molecules, mesophase pitches, polyacrylonitrile and aromatic hydrocarbons like naphthalene, anthracene, pyrene and ferrocene. Metal particles added to carbon aerogels are believed to behave as catalysts for inducing graphitization. It is also believed that the metal catalyst may lower down the temperature of graphitization up to 1000° C. instead of conventional high temperature (2000-3000° C.) required for graphitization. The nanostructures formed may be tailored by changing carbon source, catalytic metals and even the conditions of carbonization. It has been reported that carbon aerogels with partially graphitized structure were synthesized by catalytic graphitization using Cr, Fe, Co, and Ni, and the resulting gels were mesoporous. Macroporous, low content (5%), transition metal-doped carbon aerogels reportedly have been prepared by the sol-gel method from resorcinol-formaldehyde mixtures containing the corresponding metal acetate or chloride. The transition metals specially from the iron sub group have been reported to be excellent catalysts for the graphitization of amorphous carbon due to the d-electron configuration and ionization potential of transition metals. Graphitized metal carbon aerogels in the form of nanostructured rings, onions and ribbons have been reported earlier when different transition metals were treated under various conditions. It has been reported that pyrolysis of metallocenes (e.g., ferrocene, cobaltocene and nickelocene) in the presence or absence of other hydrocarbons gives carbon nanotubes without any external metal catalyst. It has also been reported that pyrolysis gave rise to metal particles such as cobalt and iron covered by graphite sheets or carbon coated metal nano particles.

The metal particles used as catalysts for graphitization of carbon aerogels, in case catalytic particles are transition metals, have also been reported to exhibit magnetic properties; hence the aerogels may have graphitic as well as magnetic properties making them more interesting with different practical applications. Magnetic nanoparticles have attracted significant academic and technological attention because of their unique physical properties and potential applications in magnetic recordings, environmental protection, biomedicine, and magnetic resonance imaging as contrast agents, field-oriented drug delivery systems, biotoxin scavengers, as well as the magnetic fluid hyperthermia. Recently, ferromagnetic transition metal nanoparticles have boosted intensive research work, apparently because of their excellent magnetic properties (the saturation magnetization of Fe nanoparticles is twice that of magnetite, which is a very popular magnetic material). So far, numerous techniques have been developed to synthesize carbon-encapsulated iron nanoparticles (CENPs), including the arc-discharge, detonation, magnetron and ion-beam co-sputtering, RF plasma torch, mechanical milling, catalytic pyrolysis, co-pyrolysis, spray pyrolysis and chemical vapor condensation. Nevertheless, most of the aforementioned techniques require relatively drastic conditions that typically lead to operational complexity and expensive propositions.

The magnetic nanoparticles made of pure metallic phases, despite better magnetic performance, may undergo spontaneous unwanted and uncontrollable reactions: (i) surface oxidation, (ii) agglomeration, and (iii) corrosion. The specific properties of magnetic nanoparticles (that are made of pure metallic phases) may be preserved by encapsulating them in thin protective coatings. Several encapsulation agents have reportedly been proposed to enhance their stability, e.g., silica, polymers, boron nitride, gold and carbon. Polymer-coated nanoparticles are known to have limited stability at elevated temperatures and may become permeable. Silica shells frequently possess a porous structure and are easily etched in alkaline solutions. Boron-nitride (BN) and carbon coatings are free of these drawbacks. These coating agents are resistant to acids, bases, greases, oils and remain stable at high temperature (up to 650 K under a pure oxygen atmosphere). Carbon coatings, unlike their BN counterparts, are expected to be readily susceptible to chemical functionalization. Moreover, the carbon coatings on CENPs produced by these methods often do not clearly show a graphitic structure that is expected to protect effectively the metal cores.

SUMMARY

The present disclosure provides a series of new and improved porous aerogels in the form of hyperbranched polyamide aerogels. The polyamides are prepared from monomers having increased levels of aromatic content per functional group compared to conventional polyamides. Hyperbranched polymers have highly branched architecture with a variety of reactive and non-reactive end groups. In the preparation of certain polymers, it has proven useful to utilize monomers in which the ratio of aromatic rings to functional groups is at least about 1:1.5. Their structure resembles the branching exhibited by many plants, particularly trees. One aspect of the current disclosure involves the new hyperbranched polymeric aerogel having the following repeating units, which comprise carboxamide groups, represented by formula I:

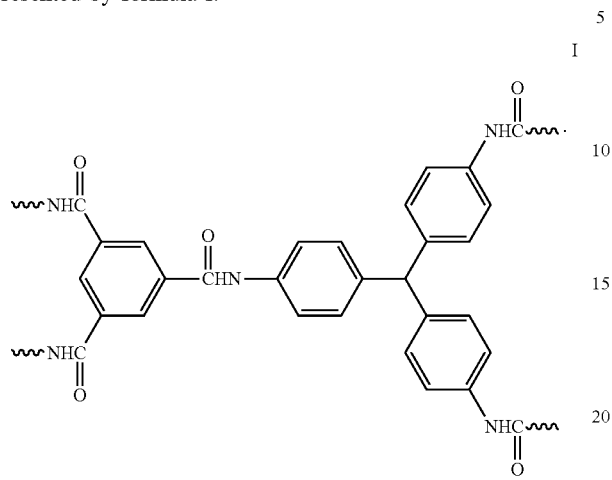

The hyperbranched structure of the polymer can be represented by the following formula II:

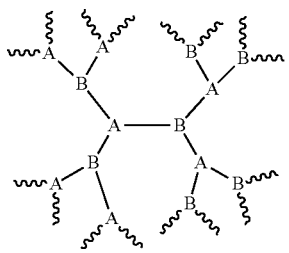

where A is:

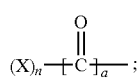

B is:

and X and Y are aromatic groups and units A and B are linked through an amide group. In certain embodiments the ratio of (a+b):(n+m) is at least about 1:1.5. In certain applications, A can be:

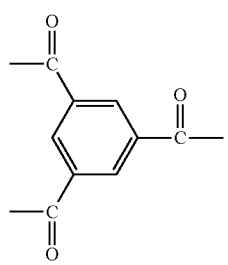

and B can be:

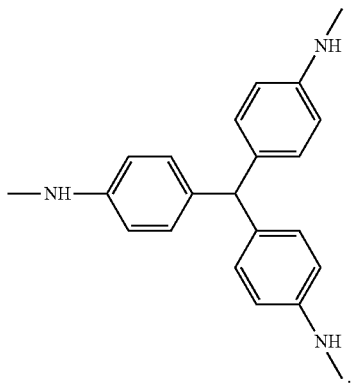

Certain of the porous polymeric aerogels of the present disclosure exhibit a bulk density between 0.205 to 0.399 g/cc, porosity between 69% to 84%, a Young's modulus equal or less than 50 MPa, specific energy absorption between 2 to 37 J/g, a speed of sound between 47 to 375 m/s and a thermal conductivity between 0.028 to 0.039 W/m·K.

The present disclosure further provides a novel method for synthesis of the porous polyamide aerogel with a hyperbranched structure from monomers having increased levels of aromatic content per functional group. Suitable monomers include the combination of an aromatic polycarboxylic acid and an aromatic polyisocyanate. The polymerization proceeds under mild to moderate conditions. Accordingly, one aspect of the present disclosure involves a method for synthesizing the polyamide aerogel from trifunctional aromatic carboxylic acids and trifunctional isocyanates in a dilute aprotic solvent such as DMF at a moderately elevated temperature. In certain examples, the monomer concentrations were selected to provide resulting polymer slurries containing between: (a) about 5-25 wt. % solids, (b) 10-25 wt. % of solids, and (c) 10-15 wt. % solids. A still further aspect of the present disclosure involves the step of drying the wet-gels with liquid $CO_2$. A suitable polycarboxylic acid includes s 1,3,5-tricarboxybenzene (trimesic acid) whereas suitable aromatic polyisocyanates include tris(4-isocyanatophenyl)-methane, methylene biphenyl diisocyanate, 1,3-phenylene diisocyanate, 1,1'-biphenyl diisocyanate and 1,1'-oxy-bis-(isocyanatobenzene).

In another embodiment of the invention, described herein are polyamide polymers incorporating multi-ferrocene groups. In one aspect, these ferrocene-containing polyamide polymers are ferrocene based organic aerogels that are porous. In another aspect, they create a 3D-network in aerogel with Fe metal as a part of the polyamide chain, where the Fe metal is covalently bonded instead of doping, impregnating or ion exchanging. In another embodiment, these aerogels undergo catalytic pyrolysis to produce carbon encapsulated magnetic iron nanoparticles with homogenous distribution of CENPs throughout the aerogel, while maintaining the porous structure, hence ending up in an aerogel with magnetic as well as catalytic properties. Also described herein is a convenient, simple and versatile method for the synthesis of a variety of encapsulated metallic particles depending upon the initial metal precursors and the carbon rich counterpart.

In another embodiment, a method of preparation is described herein in which a ferrocene-based organic aerogel is prepared by a one pot synthesis of just two monomers without any polymerization catalyst, resulting directly in the aerogel. The process is similar to the process described above, but comprises the reaction of a ferrocene carrying a multiplicity of carboxylic acid groups with a polyisocyanato-aromatic compound. Illustrative of this process is the reaction of 1,1'-ferrocene dicarboxylic acid (FDA) and tris (4-isocyanatophenylmethane) (TIPM). It is to be understood that, as contemplated herein, other ferrocene polycarboxylic acids and other polyisocyanato-aromatic compounds may be used as well. Illustrative of other ferrocene polyacids are ferrocene tricarboxylic acids, ferrocene tetraacids, and the like. It is understood that the multiplicity of carboxylic acid groups can be attached on one of the cyclopentadiene rings of the ferrocene or on both cyclopentadiene rings of the ferrocene, in a multiplicity of arrangements.

In another embodiment, described herein is solid state pyrolysis at high temperatures of the ferrocene polyamide aerogels (Fc-PA). In one aspect, this pyrolysis leads to reduction of iron metal and formation of nano-sized metallic particles distributed in carbon matrix, responsible for restructuring the carbon framework into different nano-graphitic structures. In another aspect, it is described herein that the iron particles are catalytic, and are become encapsulated as core by creating graphitic shells of few nm around them. In another aspect, it is described herein that the iron particles become magnetic by heat treatment. High temperature treatment changes these CENPs to different graphitic structures depending upon the pyrolysis conditions.

In another embodiment of the invention, disclosed herein are ferrocenyl carboxamide aerogels that possess numerous useful applications related to those discussed above; illustrative examples are described in the following discussion. In one aspect, these ferrocenyl carboxamide aerogels are prepared by a one-pot reaction of inexpensive isocyanates with ferrocene-containing carboxylic acids, using a method similar to that described above for the carboxamide aerogels, and resulting in decarboxylation and loss of $CO_2$. Illustratively, the inexpensive isocyanates may be compounds such as tris(4-isocyanatophenylmethane) (TIPM), and the ferrocene-containing carboxylic acids may be compounds such as (1,1'-ferrocenedicarboxylic acid) (FDA), and the like. Thus, another aspect of the current disclosure involves the new hyperbranched polymeric aerogels having the following repeating units, which comprise ferrocenyl carboxamide groups, represented by formula III:

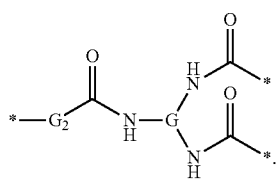

III wherein:
G represents a group selected from aryl, (aryl)-R-(aryl), and (aryl)-R-(aryl)$_2$; where each aryl independently represents an optionally substituted aromatic ring; and where R is a bond or a $C_1$-$C_6$ straight chain or branched chain alkyl group;
$G_2$ represents a ferrocenyl moiety; and
(*) denotes a linkage point.

An illustrative example of the repeating units of the ferrocenyl carboxamide aerogels is shown in the following formula IV:

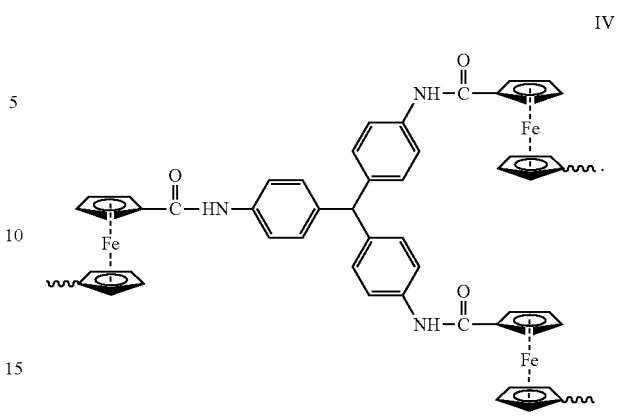

IV

DESCRIPTION OF DRAWINGS

FIG. 9 displays the CPMAS $^{13}C$ NMR of ferrocene polyamide aerogels (Fc-PA).

FIG. 18 displays the magnetic hysteresis curve of Fc-PA aerogel (Left) and pFc-PA-800° C.-$H_2$ (Right) measured at room temperature.

FIG. 21 displays the Raman spectra of pFc-PA aerogels (left) and gFc-PA (right).

FIG. 22 displays the XRD pattern of pFc-PA aerogels (left) and gFc-PA aerogels (right).

FIG. 23 displays $N_2$ sorption isotherms of pFc-PA aerogels (left) and gFc-PA aerogels (right) inset showing BJH pore diameter.

FIG. 31 displays a reaction scheme for synthesis of FcPA-xx aerogels.

FIG. 33 displays SEM data. (A) SEM of FcPA-15. (B) SEM of Fe@C.

DETAILED DESCRIPTION

Figure 1:
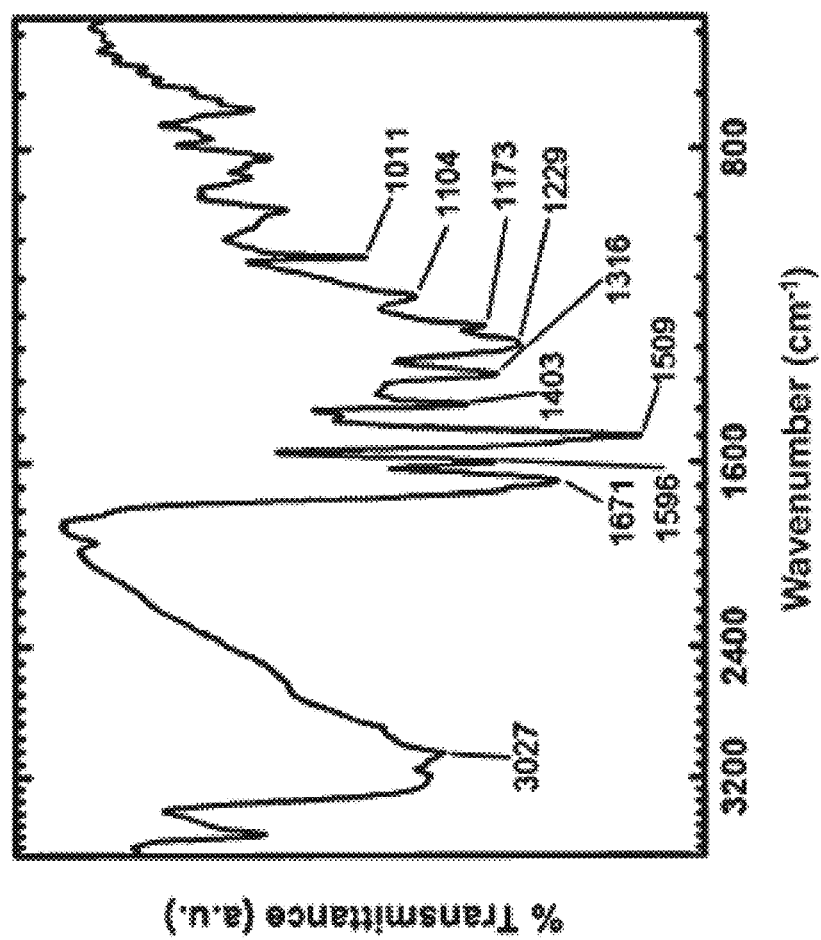
FIG. 1 provides an IR spectrum of a polyamide aerogel prepared from trimesic acid and tris(4-isocyanatophenyl) methane using 15% w/w solids in DMF.

Before the present methods, implementations and systems are disclosed and described, it is to be understood that this invention is not limited to specific synthetic methods, specific components, implementation, or to particular compositions, and as such may, of course, vary. It is also to be understood that the terminology used herein is for the purpose of describing particular implementations only and is not intended to be limiting. Neither are mechanisms which have been provided to assist in understanding the disclosure meant to be limiting.

As used in the specification and the claims, the singular forms "a," "an" and "the" include plural referents unless the context clearly dictates otherwise. Ranges may be expressed in ways including from "about" one particular value, and/or to "about" another particular value. When such a range is expressed, another implementation may include from the one particular value and/or to the other particular value. Similarly, when values are expressed as approximations, for example by use of the antecedent "about," it will be understood that the particular value forms another implementation. It will be further understood that the endpoints of each of the ranges are significant both in relation to the other endpoint, and independently of the other endpoint. "Optional" or "optionally" means that the subsequently described event or circumstance may or may not occur, and that the description includes instances where said event or circumstance occurs and instances where it does not. Similarly, "typical" or "typically" means that the subsequently described event or circumstance often though may not occur, and that the description includes instances where said event or circumstance occurs and instances where it does not.

The present disclosure provides a series of new and improved multifunctional porous aramids (aerogels) having high mechanical strength in combination with the porosity of an aerogel. The design of such aerogels imposes several interrelated chemical and structural issues. According to cellular solid theory, the mechanical strength of porous solids (e.g., honeycombs) increases with density and pore wall thickness. In aerogels, that design rule is complicated by well-defined weak points on the pore walls. Covalently bridging (e.g. crosslinking) inorganic skeletal nanoparticles (e.g., silica, vanadium, rare earth oxides) with polymers renders the structure robust, without adding substantially to the pore wall thickness. Normalized for density, the mechanical properties of those porous materials (referred to as crosslinked polymer aerogels) compete with those of bulk materials and in some aspects, (e.g., the specific energy absorption under compression) surpass the latter. Accomplishing a similar result with a polymer such as Kevlar®- or Nomex®-type aramids presents several challenges because of the limited chances for crosslinking and because the long polymeric strands tend to pack densely in order to maximize their non-covalent interactions (e.g., hydrogen bonding). Initial efforts involved the polymerizations focused on difunctional, single aromatic core monomers that formed flocs and were not characterized further. The polymerization of trifunctional single aromatic monomers initially provided hyperbranched structures that exhibited significant solubility and liquid crystalline properties in certain solvents. However, polymerizations in DMF provided large aggregates (molecular weights in the 700K-1 M range), which at high concentrations behave as shear thinning gels. In order to further decrease the solubility of the aerogel, the aromatic content of the monomer per functional group reacting was further increased. Kevlar and Nomex are registered U.S. trademarks belonging to E. I. du Pont de Nemours and Company CORPORATION DELAWARE 1007 Market Street Wilmington Del. 19898.

Thus, the present disclosure provides a series of new and improved porous hyperbranched polyamide aerogels formed from monomer systems having increased ratios of aromatic content per functional group compared to conventional polyamides. According to one aspect of the present disclosure, the polyamide aerogels may be crosslinked by utilizing monomers having the formula:

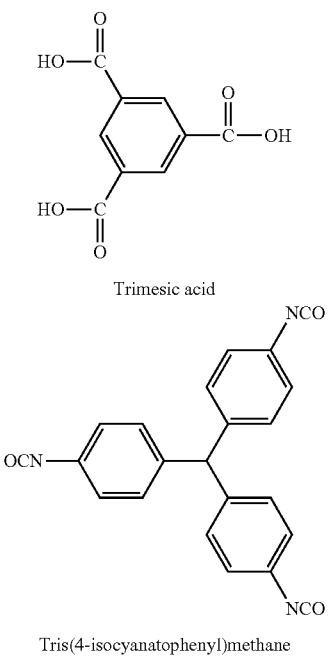

Polymerization of trimesic acid and tris(4-isocyanatophenyl)methane provided a hyperbranched polyamide aerogel having repeating units illustrated below.

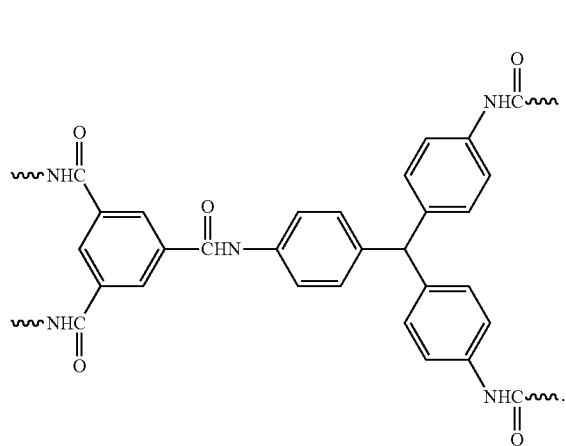

I

The hyperbranched structure of the polymer is illustrated by structure I above. In addition, the direction of the amide linkage can be reversed by utilizing monomers such as 1,3,5-Tris(4-carboxyphenyl)benzene and 1,3,5-triisocyanatobenzene.

The present disclosure further provides a method for the synthesis of the new porous polyamide aerogels. Rather than adopting the conventional pathways to polyamides either by dehydration of the salt product of the reaction between carboxylic acids and amines at relatively high temperature, or by multistep reactions of acid halides and amines, the present method employs an underutilized pathway using the multifunctional aromatic carboxylic acids and the multifunctional aromatic isocyanates in a one-step reaction carried out under mild conditions.

Polymerization of trifunctional aromatic carboxylic acids and isocyanates in dilute DMF solutions using the reaction of the carboxylic acid group (—COOH) with isocyanates (—N═C═O) to produce amides (—NH(C═O)—) induces early phase separation of surface-active aramid nanoparticles that form a solvent-filled 3D network stabilized against collapse by the chemical energy of the interparticle covalent bridges (crosslinks). These wet-gels can then be dried with liquid $CO_2$ to produce lightweight and highly porous materials having substantial strength.

Aspects of the present method include polymerizing trifunctional aromatic carboxylic acids and isocyanates in dilute DMF solutions at a moderately elevated temperature to form a polyamide aerogel. Further aspects of the present method involve the steps of adding a solvent to the wet-gels that is miscible with liquid $CO_2$.

Equations 1 and 2 provide an exemplary synthetic pathway for producing a polyamide aerogel and a possible step-by-step reaction mechanism illustrating the polymerization of a carboxylic acid and an isocyanate. As shown in equation 1, the process is implemented with benzene-1,3,5-tricarboxylic acid (trimesic acid, TMA) and tris(4-isocyanatophenyl)methane (TIPM) in DMF solutions heated to as high as about 135° C., but more preferably as high as about 90° C., with the release of $CO_2$.

In another embodiment, described herein is a series of new polymeric ferrocene carboxamide aerogels. In one aspect, these polymeric ferrocene carboxamide aerogels are porous; in another aspect, they are hyperbranched. The structure of these polymeric ferrocene carboxamide aerogels can be represented by the following formula V:

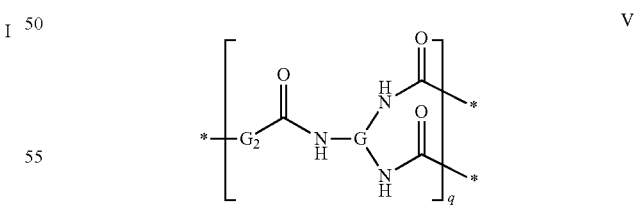

V wherein:
G represents a group selected from aryl, (aryl)-R-(aryl), and (aryl)-R-(aryl)$_2$; where each aryl independently represents an optionally substituted aromatic ring; and where R is a bond or a $C_1$-$C_6$ straight chain or branched chain alkyl group;
$G_2$ represents a ferrocenyl moiety;
(*) denotes a linkage point; and
q is an integer in the range of 2-10000.

Figure 30:
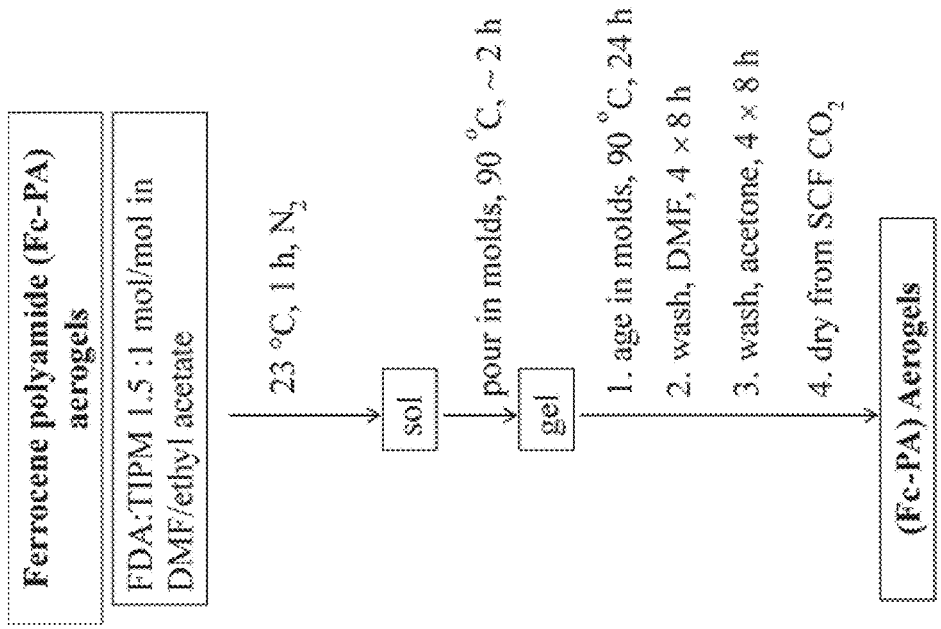
FIG. 30 displays a summary of the formation of ferrocene polyamide aerogels (Fc-PA).

In another embodiment, the present disclosure further provides methods for the synthesis of the new ferrocene carboxamide aerogels (Fc-PA). In one aspect, these methods of synthesis are similar to those described above for the reaction of trifunctional aromatic carboxylic acids and isocyanates, but involve instead the polymerization reaction of multifunctional ferrocene carboxylic acids with polyfunctional aromatic isocyanates to produce the corresponding ferrocene carboxamide groups. In one aspect, these methods comprise the use of an anhydrous aprotic solvent. Illustratively, the aprotic solvent is a carboxamide solvent, such as dimethylformamide (DMF), dimethylacetamide (DMA), N-methyl-2-pyrrolidone (NMP), and the like. Illustratively, equations FA-1 and FA-2 and FIG. 30 below provide an exemplary synthetic pathway for synthesis of a 1,1'-ferrocene dicarboxylic acid, and for its reaction with tris(4-isocyanatophenyl)methane (TIPM) in DMF solution, with the release of $CO_2$, producing the ferrocene carboxamide aerogels. In one aspect, this reaction may be carried out at ambient temperature.

In another embodiment, a new route is described herein to make highly efficient noble metal (Au, Pd, Pt) catalysts. Carbon supported metal aerogels (pFc-PA) were synthesized successfully from the Fc-Pas, followed by transmetalation with noble metals to yield (tFc-PA-Au/Pt/Pd) aerogels. The transmetalation allows one to optimize the catalyst for a given application by using the respective metals for exchange during transmetalation without sacrificing the intricate framework of aerogel. The transmetalated aerogels were used as successful catalysts in a variety of chemical reactions. Illustratively, they can be used for catalyzing the reduction of nitrobenzene, oxidation of alcohols, Heck coupling reactions, and the like. Activities comparable to the best metal catalyst for the respective reactions described in the literature have been achieved. Without being bound by theory, it is believed that the nanoscopic architecture of aerogel provides a continuous carbon framework with mesoporosity along with the homogenous distribution of metal particles providing increased surface for catalysis as compared to the single perimeter catalyst without porosity. The ability of the aerogels nano architecture is to create multiple points of contacts with metal particles with single interfacial perimeter that forms when metal particles are transmetalated. The multiple junctions shorten the average lateral diffusion distance of the reactants to the active catalytic particles as compared to the single perimeter case. Hence the multiplicity of contacts may provide the three dimensional control of the reaction zone. The reusability of the catalyst, even after three times without losing its catalytic activity, makes it a good option on basis of reusability, easy processability and handling.

The noble metal ions from corresponding metal chloride solution are precipitated in the form of metallic particles as a result of redox reaction between noble metal ions and Fe containing species (Fe and $Fe_3C$). Another possible explanation might be formation of free active surface in view of Fe and $Fe_3C$ dissolution in an acidic environment which may play an important role in achieving transmetalation. It is believed that the phenomenon of transmetalation cannot be achieved in the absence of graphitic carbon as it contains surface active groups like hydroxyl ions attached to the edges of the graphene layers which have redox properties for the noble metal ions. This was observed in a control experiment, where transmetalation was only observed at 800° C. but not at lower temperatures.

The anchoring of noble metals (Au, Pd, Pt) on pFc-PA aerogels may be due to donor-acceptor interactions of delocalized p-electrons of graphitic carbon and vacant d-orbital of noble metal with further reduction of metal based on the electron donating properties of the graphitic carbon.

EXAMPLES

The following examples are provided for the purpose of illustration only, and it is to be understood that they are not intended to be limiting, but that other variations and/or modifications are contemplated herein that are known to those skilled in the art, and that are within the scope and spirit of the disclosure herein.

(A) Polymeric Aerogels Comprising Carboxamide Groups.

Example 1

Synthesis of Aramid Aerogels

A solution of TIPM as received (Desmodur RE, 13.3 mL (13.6 g), containing 3.67 g of TIPM in anhydrous ethylacetate, 0.01 mol) and TMA (2.10 g, 0.01 mol) in varying amounts of anhydrous DMF (e.g., 24.0 mL (22.6 g) for 15% w/w solids) was stirred at 90° C. under $N_2$ for 1 h. The resulting sol was poured into polypropylene molds (Wheaton polypropylene OmniVials, Part No. 225402, 1 cm diameter), which were sealed in a glove box and heated at 90° C. for 24 h. (The 15% w/w sol gels in 2.5 h from mixing.) Gels were washed with DMF, acetone (4× with each solvent, using 4× the volume of the gel) and dried with liquid $CO_2$ in the form of a supercritical fluid (SCF). The same procedure was followed at room temperature and at 135° C. (using glass molds) for the CPMAS $^{13}C$ NMR studies.

The method provided is essentially a one-pot, one-step process carried out according to equation 1.

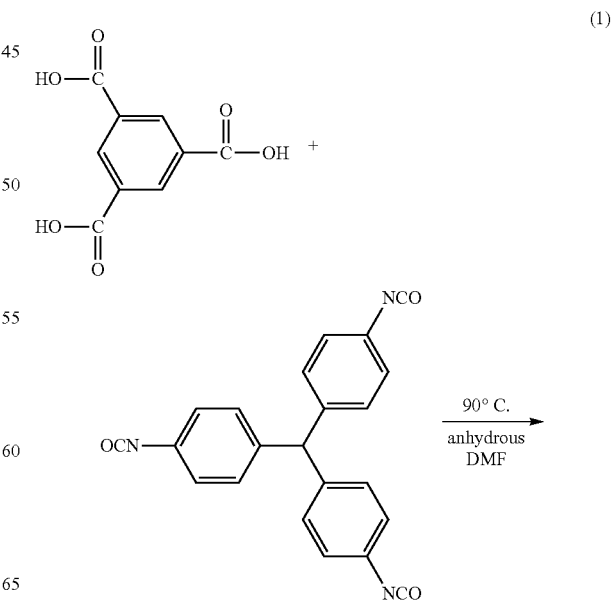

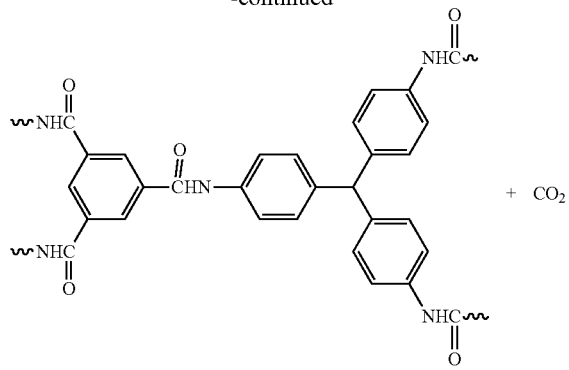

Figure 3:
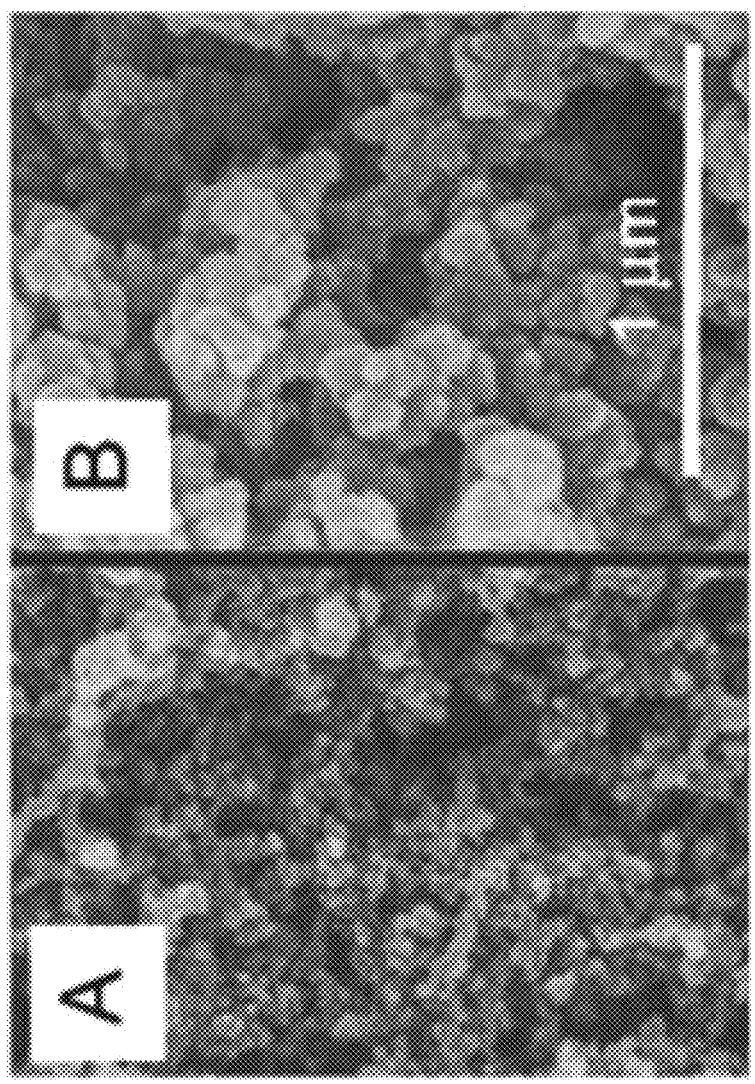
FIG. 3 provides SEM's of aramid aerogels at 5% w/w solids (A) and 25% w/w solids (B).

Monolithic aerogels of variable density were obtained by varying the monomer concentration in the sol. The IR spectrum reproduced in FIG. 3 illustrates the NH stretch at 3027 cm$^{-1}$, the amide carbonyl stretch at 1671 cm$^{-1}$ and the NH bending vibration coupled to the C—N stretch at 1509 cm$^{-1}$. The reaction of the carboxylic acid (—COOH) with an isocyanate (—N═C═O) is a room temperature process yielding an intermediate that is a mixed carbamic-carboxylic anhydride intermediate as illustrated in equation (2).

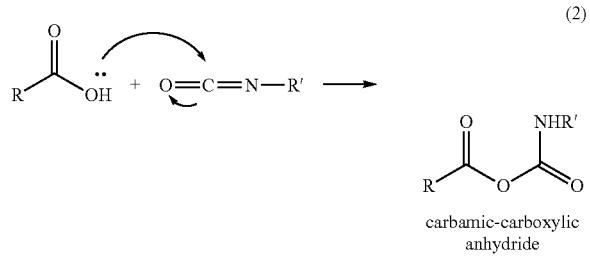

Upon heating the intermediate, decarboxylation occurs producing an amide either by losing the isocyanate sp carbon (equation 3a), or bi-molecularly through urea and anhydride intermediates (equation 3b).

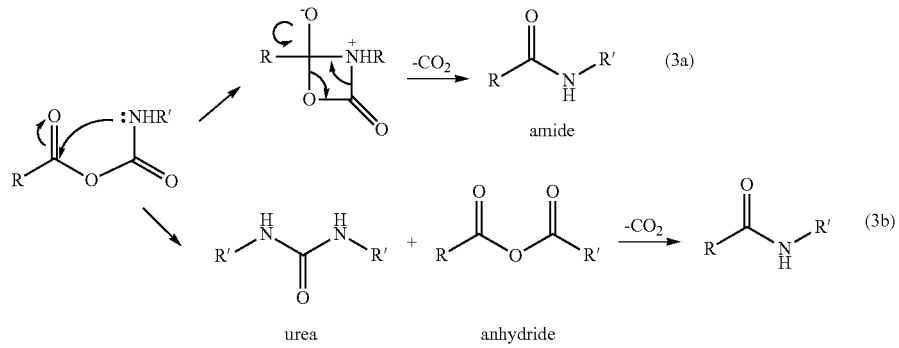

Figure 2:
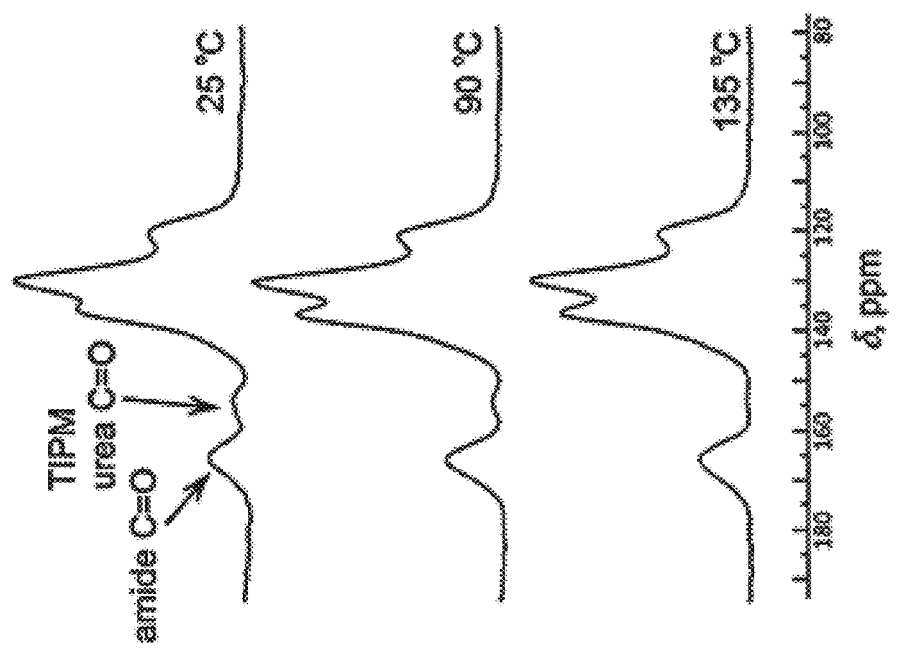
FIG. 2 provides a solid state $^{13}C$ NMR spectra of polyamide aerogels prepared from trimesic acid and tris(4-isocyanatophenyl)methane using 15% w/w solids in DMF at the three temperatures indicated.
Figure 4:
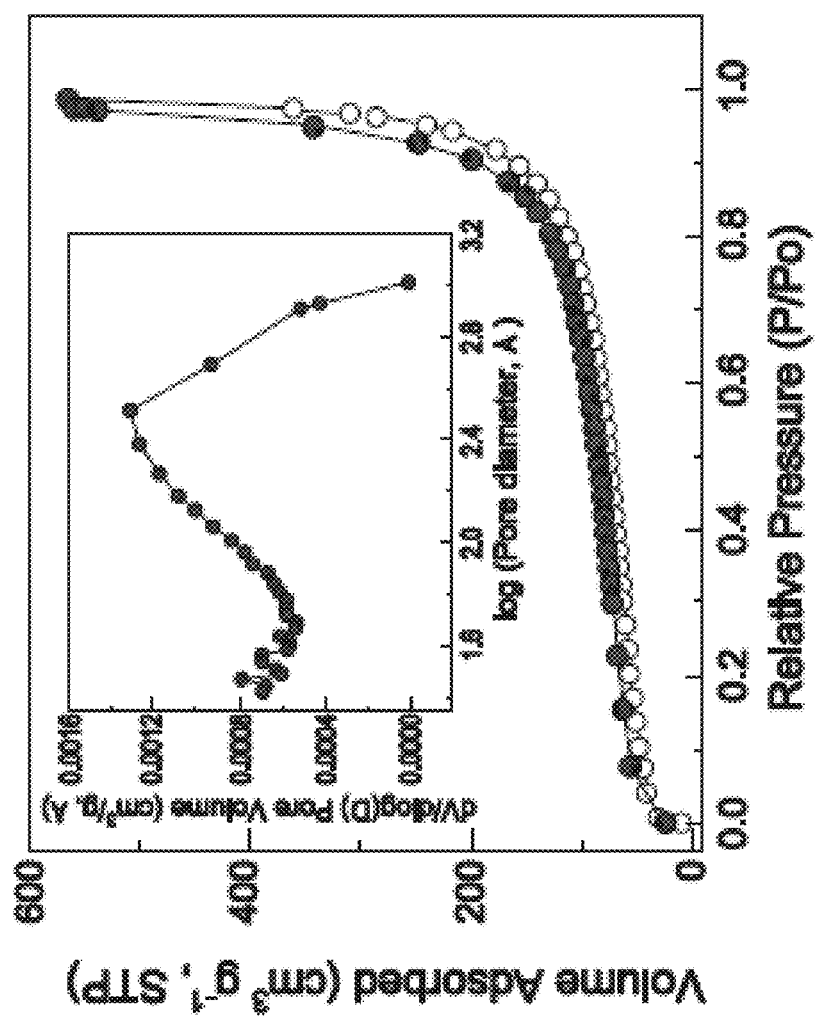
FIG. 4 provides an $N_2$-sorption isotherm (obtained at 77K) of a 15% w/w solids sample (open circles: adsorption; dark circles: desorption). Inset: Pore size distribution via the Barrett-Joyner-Halenda (BJH) plot applied on the desorption branch of the isotherm.

However, once urea and anhydride have been fixed on the network by reaction of their other functional groups via equation 3a, they can no longer diffuse and react further to amide via equation 3b. Indeed, the presence of TIPM-derived polyurea was detected with solids $^{13}$C NMR at 157 ppm (FIG. 2) by comparison with the spectrum of the pure polymer. The amount of TIPM-derived urea decreases by gelation at elevated temperatures (FIG. 4), implying that equation 3a and the first step of equation 3b proceed with comparably fast rates, while the second step of equation 3b (formation of amide by loss of $CO_2$) is significantly slower and is accelerated by heating. All data presented below concern gels obtained by heating to 90° C. (equation 1). Combinations of terephthalic acid/TMT; trimesic acid/diphenyl methane diisocyanate; and TMA/TMI all provided gels.

Example 2

General Testing Methods

Supercritical fluid (SCF) drying was carried out in an autoclave (SPI-DRY Jumbo Supercritical Point Dryer, SPI Supplies, Inc. West Chester, Pa.). Bulk densities were determined from sample weight and dimensions. Skeletal densities were determined with helium pycnometry using a Micromeritics AccuPyc II 1340 instrument. N2 sorption porosimetry was carried out with a Micromeritics ASAP 2020 Surface Area and Porosity Analyzer. IR samples were included in KBr pellets with a Nicolet-FTIR Model 750 Spectrometer. Solid-state $^{13}$C NMR determinations were carried out with a Bruker Avance 300 Spectrometer set at 75.475 MHz for carbon frequency using magic angle spinning (at 7 kHz) with broadband proton suppression and the CPMAS TOSS pulse sequence for spin sideband suppression. SEM determinations were carried out with Au-coated samples on a Hitachi S-4700 field emission microscope. X-ray diffraction (XRD) was carried out with a PANalytical X-Pert Pro Multi-Purpose Diffractometer (MPD) and a Cu Kα radiation source. Mechanical testing under compression utilized an Instron 4469 universal testing machine frame, following the testing procedures and specimen length (2.0 cm) to diameter (1.0 cm) ratio specified in ASTM D 1621-04a (Standard Test Method for Compressive Properties of Rigid Cellular Plastics). Thermal diffusivity measurements, R, were made with a Netzsch NanoFlash Model LFA 447 flash diffusivity instrument using disk samples~1 cm in diameter, 2.0-2.2 mm thick. Heat capacities, Cp, were determined at 23° C. with powders of the same samples (4-8 mg), needed for the determination of their thermal conductivity, A, utilizing a TA Instruments Differential Scanning Calorimeter Model Q2000 calibrated against a sapphire standard and run from −10° C. to 40° C. at 0.5° C. min$^{-1}$ in the modulated T4P mode. The raw Cp data for the polyamide aerogels were multiplied by a factor of 0.920±0.028 based on measuring the heat capacities of rutile, KCl, Al, graphite, and corundum just before the current experiments and comparing values obtained with the literature values.

Example 3

Materials Characterization

Characterization data determined for the polymeric aerogels is summarized in Table 1. The monoliths shrink significantly (from 11% to 41% in linear dimensions relative to their molds, Table 1) in inverse order to monomer concentration. Consequently, bulk densities ($\rho_o$) do not vary proportionally to monomer concentration, ranging from 0.21 to 0.40 g cm$^{-3}$ even though the monomer concentration was varied five-fold, from 5% to 25% w/w solids (lower monomer concentrations did not gel).

TABLE 1

Materials characterization data of polyamide aerogels:

| Solids [% w/w] | Shrinkage [%]$^{a,b}$ | $\rho_o$ [g cm,3]$^a$ | $\rho_s$ [g cm$^{-3}$]$^c$ | Crystallinity 2θ [% degrees)] | Porosity [% v/v] | BET surface area (micropore) [m$^2$g$^{-1}$] | Pore diameter [nm]$^d$($^e$) | Particle diameter [nm] |
|---|---|---|---|---|---|---|---|---|
| 5  | 40.9 ± 0.9 | 0.205 ± 0.008 | 1.266 ± 0.014 | 79 (19, 44) | 84 | 380 (37) | 23.7 (43.0)  | 12.5 |
| 10 | 31.1 ± 0.5 | 0.288 ± 0.005 | 1.268 ± 0.010 | 47 (19, 44) | 77 | 354 (42) | 28.1 (30.3)  | 13.4 |
| 15 | 22.5 ± 0.3 | 0.324 ± 0.010 | 1.282 ± 0.010 | 51 (19, 44) | 75 | 172 (29) | 19.8 (53.6)  | 27.2 |
| 20 | 17.4 ± 0.1 | 0.361 ± 0.008 | 1.277 ± 0.008 | 60 (20, 44) | 72 | 65 (10)  | 22.9 (122.3) | 72.3 |
| 25 | 11.2 ± 0   | 0.399 ± 0.005 | 1.279 ± 0.007 | 58 (20, 44) | 69 | 15 (2)   | 33.5 (459.8) | 313  |

$^a$Represents the Average of 3 samples.
$^b$Shrinkage = 100 × [1-(sample diameter/mold diameter)].
$^c$Single sample, average of 50 measurements.
$^d$By the 4x VTotal/σ method and VTotal by the single-point adsorption method.
$^e$In parentheses, VTotal via VTotal = (1/$\rho_o$) − (1/$\rho_s$).
$^f$Particle diameter = 6/$\rho_s$σ.

Shrinking does not take place during gelation, aging, or solvent exchange; on the contrary, wet-gels swell by ~10% in linear dimensions upon transfer from their molds into fresh DMF. All shrinking takes place during drying with supercritical fluid (SCF) $CO_2$. Therefore, behaving as semipermeable membranes, polyamide wet-gels swell till stretching of the framework—which, therefore must be rather flexible—balances the osmotic pressure of the internal "solution". Then, complete collapse upon drying is halted by the covalent bonding of the network. Skeletal densities, $\rho_s$, fall in the 1.27-1.28 g cm$^{-3}$ range, close to, but lower than the densities of Kevlar® and Nomex® (1.44 g cm$^{-3}$). The invariance of $\rho_s$ with monomer concentration signifies absence of closed pores, and the values reflect the effect of crosslinking on molecular packing. Indeed, X-ray diffraction shows high crystallinity, but peaks are broad (unlike in Kevlar® where they are sharp), precluding large-scale order. Porosities, Π, calculated from $\rho_o$ and $\rho_s$ via Π=100×[(1/$\rho_o$)−(1/$\rho_s$)]/$\rho_o$ decrease from 84% to 69% v/v as $\rho_o$ increases. Despite shrinkage, all samples are highly porous.

Microscopically, aramid aerogels show aerogel-like connectivity of smaller particles into larger agglomerates (FIG. 3). Particle size increases with monomer concentration. All $N_2$ sorption isotherms rise above P/Po=0.9 and do not reach saturation, consistently with the macroporosity observed in the SEM's. Nevertheless, narrow hysteresis loops and substantial specific volumes adsorbed at low P/Po values indicate also the presence of both meso and microporosity. Brunauer-Emmett-Teller (BET) analysis yields high surface areas (σ, 380 m$^2$ g$^{-1}$) for the lower density samples, decreasing dramatically (to 15 m$^2$ g$^{-1}$) as the concentration of monomers increases. In all cases, about 10% of σ is attributed to micropores (via t-plot analysis, Harkins and Jura Model). Average pore diameters calculated by the 4V$_{Total}$/σ method using V$_{Total}$ either from the highest adsorption point in the isotherm, or via V$_{Total}$=(1/$\rho_o$)−(1/$\rho_s$), diverge as $\rho_o$ increases, consistently with larger particles yielding macropores. Calculated particle diameters (=6/$\rho_s$ σ, Table 1) increase with monomer concentration, but remain smaller than those observed in SEM. Therefore, SEM particles are higher aggregates. The lower shrinkage and the increasing particle size with monomer concentration parallels the well-studied base-catalyzed gelation of resorcinol-formaldehyde at high resorcinol-to-catalyst ratios (slower reaction), suggesting microphase separation is convoluted with kinetically controlled polymerization.

Example 4

Mechanical Characterization

Figure 5:
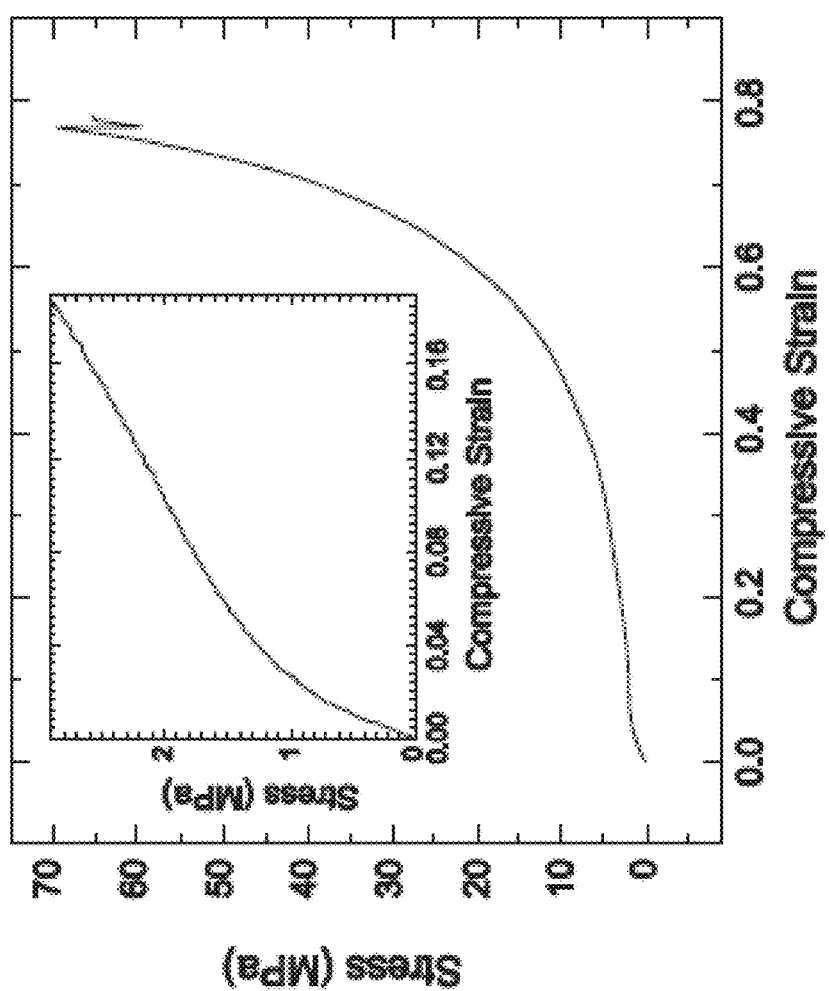
FIG. 5 provides a typical quasi-static compression data of a 15% w/w solids aramid aerogel sample. (Diameter~0.78 cm; Length:Diameter=2:1.)
Figure 6:
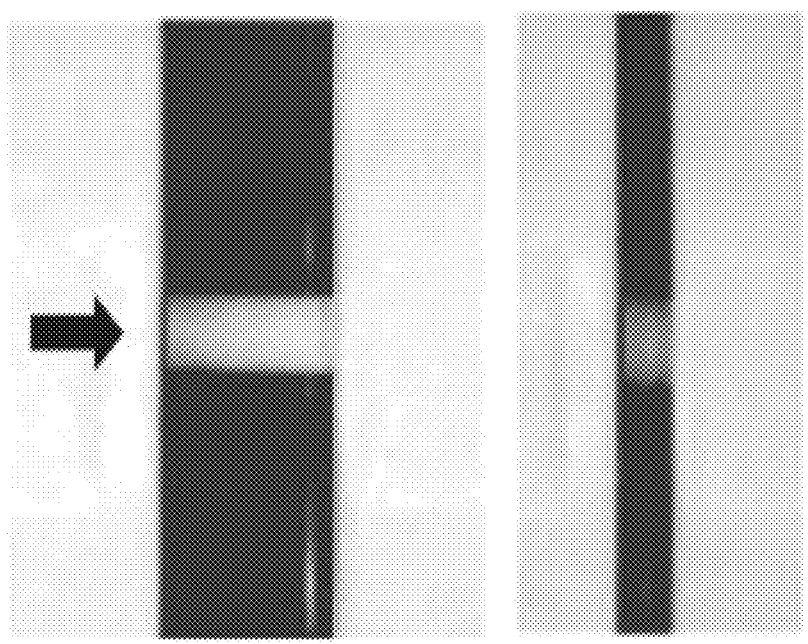
FIG. 6 illustrates the low-strain region magnified for the sample examined in FIG. 5.

Larger particles are expected to have fewer interparticle contacts, therefore lower covalent connectivity and thus lower chemical energy stored in the 3D structure. Hence, not surprisingly, for not very different $\rho_o$, the mechanical properties under quasi-static compression (FIG. 5) decrease precipitously as monomer concentration increases (Table 2). Overall, stress-strain curves show a short linear range (<3% strain) followed by plastic deformation and inelastic hardening. At low $\rho_o$, i.e., with smaller particles, samples fail at high (~80%) strain, but not catastrophically. The ultimate compressive strength per unit density (238 MPa/(g cm$^{-3}$), calculated from Table 2 for the 0.324 g cm$^{-3}$ samples) is within 10% equal to that of Kevlar® 49 (257 MPa/(g cm$^{-3}$) calculated from literature values of 370 MPa at 1.44 g cm$^{-3}$). The Young's modulus, E, (slope of the linear range at <3% strain, see FIG. 5, inset), is controlled by the amide interparticle bridges and is comparable to that of other isocyanate-derived organic aerogels of similar $\rho_o$, but is also significantly lower than that of polyurea-crosslinked silica and vanadium (233 and 206 MPa, at 0.55 and 0.44 g cm$^{-3}$ respectively), whose stiffness is controlled by the inorganic framework. The low values of the Young's modulus translate into open-air-like speed of sound waves (calculated using equation 4 below, see Table 2), rendering those materials suitable for acoustic insulation. The speed of sound was determined by the following equation 4:

$$\text{speed of sound} = (E/\rho_o)^{0.5} \qquad (4)$$

At the same time, however, the combination of high fail strains and high ultimate compressive strengths has yielded high integrated areas under the stress/strain curves. Thus, the specific energy absorption under compression (a measure of toughness) reaches 37 J g$^{-1}$, surpassing Kevlar® 49-epoxy composites (11 J g$^{-1}$), and renders polyamide aerogels appropriate for similar applications, for example as core for armor plates.

the exceptional mechanical strength and the acoustic insulation value of these materials.

For certain polymer aerogels, the polymers have exhibited a bulk density that is ≤0.4 g/cc, a porosity≥69%, a Young's modulus≤50 MPa, a specific energy absorption≤37 J/g, a speed of sound≥47 m/s, and a thermal conductivity≥0.028 W/m·K. In other polymer aerogels, the polymers have

TABLE 2

Selected mechanical characterization data of polyamide aerogel under uniaxial quasistatic compression at 23° C.

| Solids'[ % w/w | $\rho_o$ [g cm$^{-3}$] | Strain rate [s$^{-1}$] | Young's modulus [E, MPa] | Speed of sound [m s$^{-1}$]$^a$ | Ultimate strength [MPa] | Ultimate Strain'[%] | Specific energy [J g$^{-1}$] |
|---|---|---|---|---|---|---|---|
| 10 | 0.288 | 0.008 | 33 ± 4 | 338 | 71 ± 9 | 80 ± 2 | 37.03 |
| 15 | 0.324 | 0.006 | 46 ± 12 | 375 | 77 ± 10 | 74 ± 2 | 36.52 |
| 20 | 0.361 | 0.005 | 50 ± 0 | 372 | 23 ± 1 | 61 ± 3 | 14.64 |
| 25 | 0.399 | 0.006 | 0.9 ± 0.1 | 47 | 5.2 ± 1.7 | 21 ± 7 | 2.77 |

$^a$Calculated via equation 4.

Example 5

Thermal Conductivity

The thermal conductivity, λ, was calculated via equation 5.

$$\lambda = \rho_o \times C_p \times R \quad (5)$$

Figure 7:
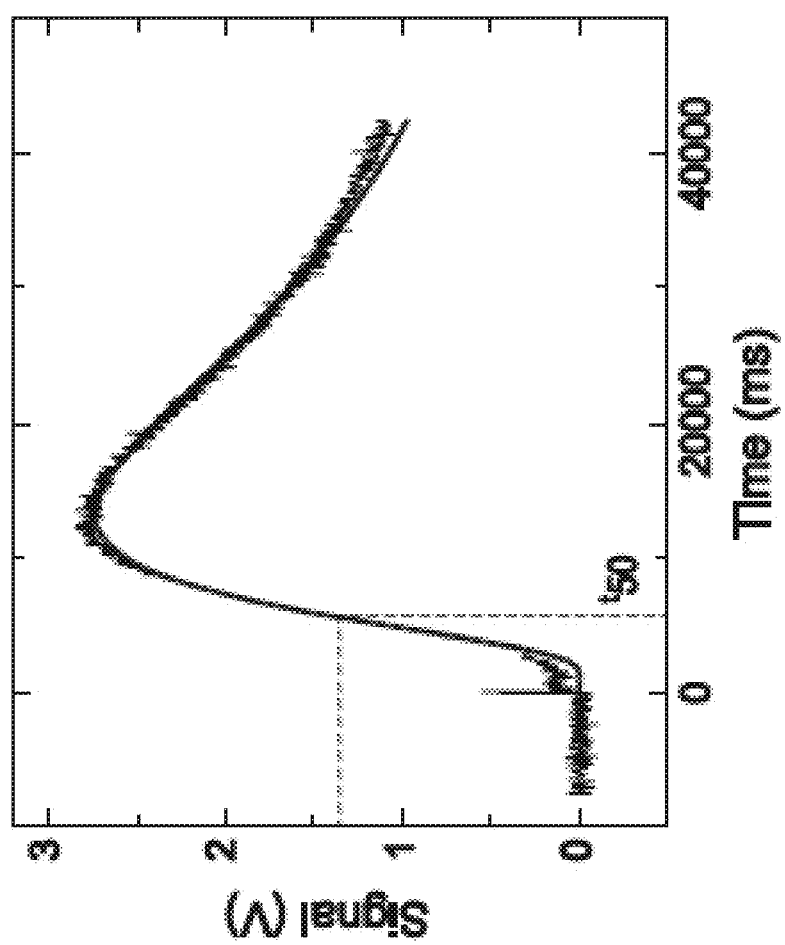
FIG. 7 provides a temperature curve of the back face of a polyamide aerogel disk (~1 cm in diameter, 2.53 mm thick, $\rho_o$=0.28 g cm$^{-3}$) coated with gold and carbon on both faces, following a heat pulse incident to the front face. Dashed reference lines indicate $t_{50}$, the time for the detector voltage (proportional to temperature) to reach half its maximum value. Data have been fitted to the pulse-corrected Cowan model.

These determinations involved measuring the bulk density, $\rho_o$, the thermal diffusivity, R, and the heat capacity, Cp. R was determined with a flash diffusivity method with disk samples ~1 cm in diameter, ~2.5 mm thick (the thickness of each sample was measured with 0.01 mm resolution and was entered as required by the data analysis software). Samples were coated with gold and carbon on both faces to minimize radiative heat transfer and ensure complete absorption of the heat pulse. Typical data are shown in FIG. 7. Dashed reference lines indicate $t_{50}$, the time for the detector voltage (which is proportional to temperature) to reach half its maximum value. Data have been fitted to the pulse-corrected Cowan model. Heat capacities, Cp, at 23° C. of powders of the same samples, were measured using Modulated Differential Scanning Calorimetry (MDSC) against several standards, as described in the Experimental Section. Relevant data for two polyamide aerogel samples at densities that yield the best mechanical properties in terms of Young's modulus, ultimate strength and energy absorption (Table 2), is summarized in Table 3.

exhibited at least two of these properties, and in other polymers, at least two of these properties have been exhibited.

(B) Polymeric Aerogels Comprising Ferrocenyl Carboxamide Groups.

Example 14

Materials

All reagents and solvents were used as received, unless noted otherwise. Ferrocene, aluminum chloride, acetyl chloride, lithium aluminum hydride, dichloromethane, hexane and anhydrous N,N-dimethylformamide (DMF) were purchased from Sigma Aldrich Chemical Co. Concentrated HCl (12.1 N) was purchased from Fisher. Deuterated DMSO (DMSO-d$_6$) was obtained from Cambridge Isotope Laboratories Inc. Tris(4-isocyanatophenylmethane) (TIPM) was donated from Bayer Corp. USA.

Example 15

Synthesis and Characterization of Ferrocene Monomer (1,1'-Ferrocene Dicarboxylic Acid (FDA))

The monomer (FDA) was synthesized in two steps in good yield (63%) according to literature procedures (Rosen-

TABLE 3

Thermal conductivity data for polyamide aerogels samples prepared by using the 10% w/w and the 15% w/w solids formulations at 23° C.

| Material | Bulk density, $\rho_o$ [g cm$^{-1}$] | Heat Capacity, Cp [J g$^{-1}$ K$^{-1}$] | Thermal diffusivity, R [mm$^2$ s$^{-1}$] | Thermal conductivity, λ [W m$^{-1}$ K$^{-1}$] |
|---|---|---|---|---|
| 10% w/w | 0.280 ± 0.009 | 0.913 ± 0.028 | 0.111 ± 0.005 | 0.028 ± 0.002 |
| 15% w/w | 0.310 ± 0.023 | 1.114 ± 0.034 | 0.112 ± 0.002 | 0.039 ± 0.003 |

Although the lowest thermal conductivity achieved (0.028 W m$^{-1}$K$^{-1}$) is above the record-low values reported for aerogels (<0.020 W m'l K'l), nevertheless it is noted that it is between those for Styrofoam (0.030 W m$^{-1}$ K$^{-1}$) and polyurethane foam (0.026 W m$^{-1}$ K$^{-1}$). This fact should be put in perspective together with the relatively low density, blum, M.; Woodward, R. B. J. Am. Chem. Soc. 1958, 80, 543; Knobloch, F.; Rauscher, W. J. Polym. Sci. 1961, 10, 651), by using Friedel-Crafts acylation reaction of ferrocene, which introduces an acyl group onto an aromatic ring followed by conversion to carboxylic acid group (Eq. FA-1). The product was characterized by elemental analysis, IR spectroscopy, $^1$H NMR, $^{13}$C NMR and thermo gravimetric analysis (TGA). Mp 250° C. (sublimed). $^1$H NMR (400 MHz, DMSO-d$_6$) δ 4.47 (d, 4H), 4.72 (d, 4H), 12.34 (s, 2H). $^{13}$C NMR (400 MHz, DMSO-d$_6$) δ 171, 73, 72, 71; IR (KBr) 3429, 1687, 1495, 1301, 514 cm$^{-1}$. Elemental Analysis, (CHN % w/w). Theoretical % for C$_{12}$H$_{10}$O$_4$Fe: C, 52.55; H, 4.38. Experimental: C, 51.83; H, 4.13. Elemental Analysis of ferrocene diacetyl intermediate, (CHN % w/w). Theoretical % for C$_{14}$H$_{14}$O$_2$Fe: C, 62.25; H, 5.18. Experimental: C, 62.22; H, 4.89.

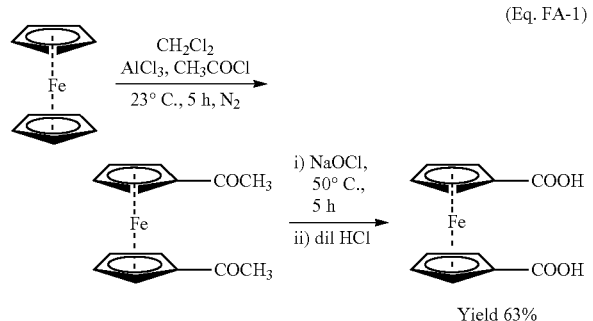

(Eq. FA-1)

Figure 8:
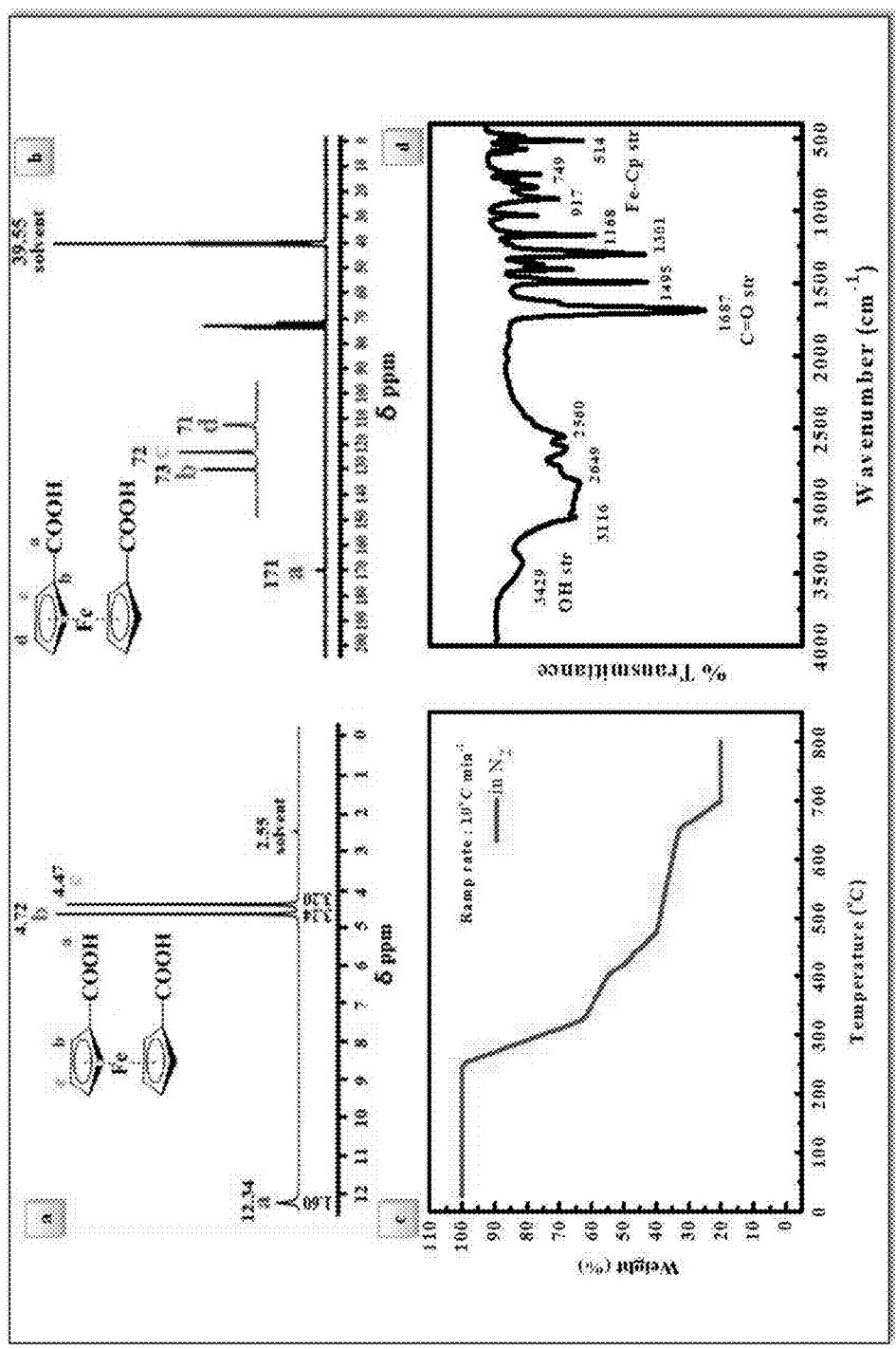
FIG. 8 provides spectroscopic and thermogravimetric (TGA) analysis data of 1,1'-ferrocene dicarboxylic acid (FDA): (A) $^1H$-NMR in DMSO-$d_6$; (B) $^{13}C$-NMR in DMSO-$d_6$; (C) TGA curve; (D) infrared (IR) spectra in KBr.

The IR spectrum of FDA (FIG. 8D) is dominated by the main IR bands of carbonyl stretching vibration (C=O) at 1687 cm$^{-1}$ while (O—H) stretching and bending vibration at 3429 and 917 cm$^{-1}$ respectively with combination bands in the range of 2640-2560 cm$^{-1}$. The IR band exhibited at 3116 cm$^{-1}$ is due to (C—H) stretching. The stretching vibrations of (C—C) bonds of rings in aromatic compounds are at 1168 and 1495 cm$^{-1}$ respectively. Absorption at 749 cm$^{-1}$ is because of deformations in (C—H) bonds. The absorption at 1301 cm$^{-1}$ is assigned to (C—O) stretching vibration, while the absorption at 514 cm$^{-1}$ is attributed to the (Fe-Cp) ring. In $^1$H NMR (FIG. 8A), all the protons show up at their subsequent shift values. In $^{13}$C NMR (FIG. 8B), all carbons of FDA monomer are resolved. No impurities are visible, which is consistent with the elemental analysis data. The resonance at 171 ppm is assigned to the carboxylic acid carbonyl, while the resonances at 71, 72, 73 ppm are assigned to the aromatic sp$^2$-carbons of the ferrocene moiety. The TGA curve (FIG. 8C) of FDA shows more than one stage of thermal degradation. Three degradation stages were observed at 298, 448 and 680° C. respectively.

Example 16

Synthesis of Ferrocene Polyamide Aerogels (Fc-PA) Via Reaction of TIPM and FDA

A solution of Desmodur RE as-received contains 27% w/w TIPM in anhydrous ethyl acetate. Typically, 13.6 g of that solution (3.67 g, 0.01 mol TIPM) and FDA (4.11 g, 0.015 mol) in variable amounts of anhydrous DMF was stirred at room temperature under N$_2$ for 1 h. Then the sol was poured into molds (Wheaton 4 mL Polypropylene Omni-Vials 1.04 cm in inner diameter, Fisher part No. 225402), which were sealed and heated at 90° C. for 2 h. Syneresis was observed during that period. Subsequently, gels were aged for 24 h at 90° C. in their molds, removed from the molds, washed with DMF (4×), acetone (4×, using 4× the volume of the gel for each wash) and dried with CO$_2$ taken out as a supercritical fluid (SCF).

Example 17

Synthesis and Characterization of Ferrocene Polyamide Aerogels (Fc-PA)

Figure 10:
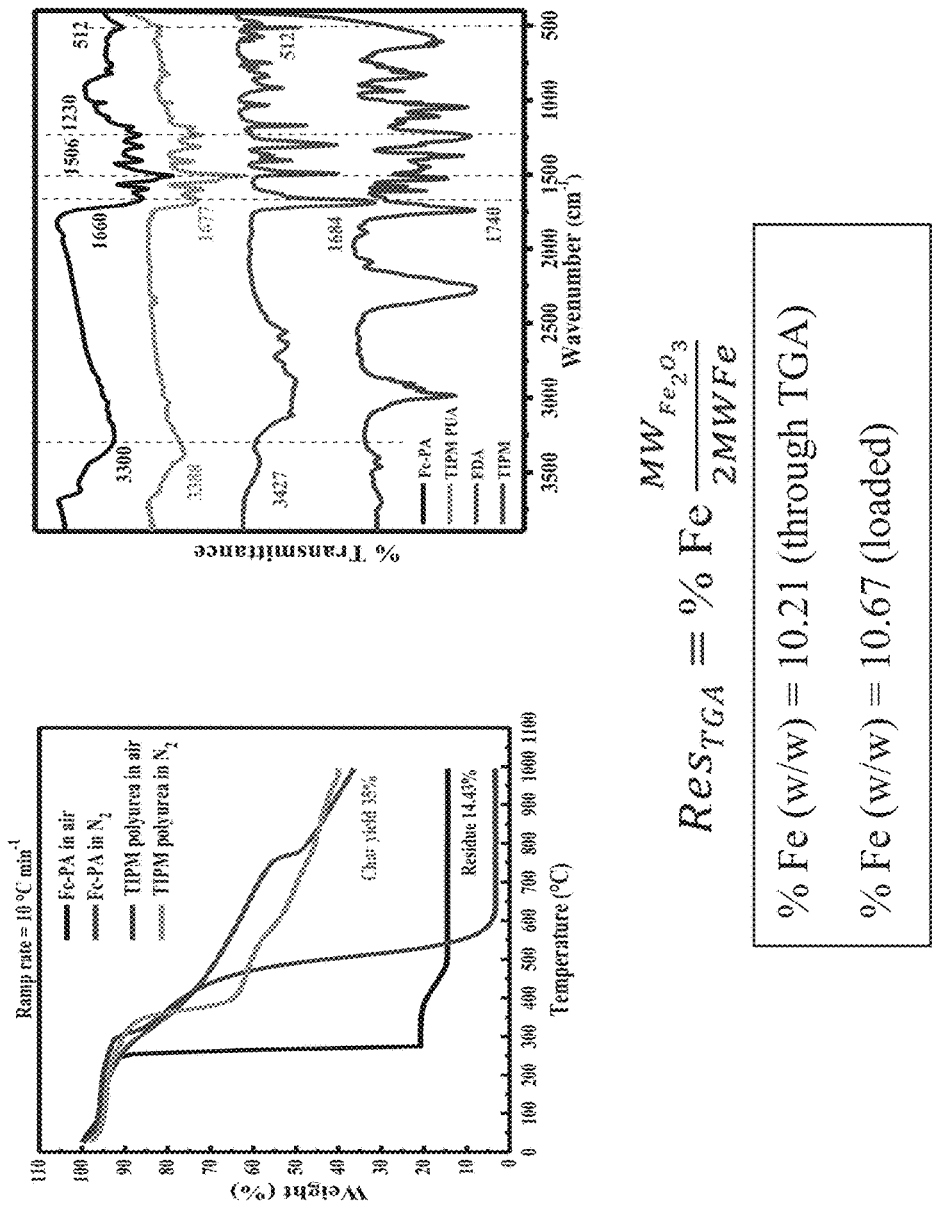
FIG. 10 displays the TGA of Fc-PA aerogels under $N_2$ and Air (left), and the IR spectra of Fc-PA in KBr (right).

Ferrocene polyamide (Fc-PA) was synthesized by a rather underutilized synthetic method for amides from carboxylic acids and isocyanates. This reaction was initiated by 1,1'-ferrocene dicarboxylic acid (FDA) and tris(4-isocyanatophenylmethane) (TIPM) (see Eq. FA-2). This is a room temperature reaction which involves carbamic-carboxylic anhydride as intermediate which yields amide either by losing the isocyanate sp carbon or bimolecularly through urea and anhydride. Formation of ferrocene polyamide aerogels (Fc-PA) is summarized in FIG. 30. Fc-PA monoliths of different densities were obtained by varying the monomer concentration. Elemental analysis results of Fc-PA aerogels are in good agreement with the calculations based on the number of atoms in the Fc-PA repeat unit. (CHN % w/w). Theoretical % C, 67.49; H, 4.08; N, 4.54. Experimental: C, 67.02; H, 3.91; N, 5.01. The IR spectrum (FIG. 10; right) exhibits NH stretching frequency at 3264 cm$^{-1}$, the amide carbonyl stretch at 1660 cm$^{-1}$, NH bending vibration at 1506 cm$^{-1}$. The absorption at 1230 cm$^{-1}$ and 512 cm$^{-1}$ assigned to (C—O) stretching and (Fe-Cp) stretching vibrations respectively. CPMAS $^{13}$C was employed which confirms the amide linkage by showing a peak around 163 ppm, nevertheless, the TIPM-derived polyurea was also detected at 154 ppm; but there is no change in the amount of TIPM-derived polyurea at ambient and elevated temperatures. The ferrocene moiety was also confirmed by the peak at 71 ppm while peaks at 119, 129, 136 ppm were attributed to TIPM sp$^2$ carbons (FIG. 9). By thermogravimetric analysis under N$_2$, Fc-PA aerogels (FIG. 10; left) are stable up to 250° C. with an initial minor weight loss due to the moisture present in the sample. Almost 55% weight loss was observed up to 750° C. as a major weight loss of Fc-PA aerogels due to the combined thermal degradation of Fc-PA polymer, further 6% weight loss is attributed to the nitrogen containing fragments, leaving char yield of 35% making them potential candidates for pyrolysis, while under oxygen, Fc-PA aerogels give 14.43% residue which corresponds to approximately 11% Fe metal loaded initially in the form of iron monomer.

(Eq. FA-2)

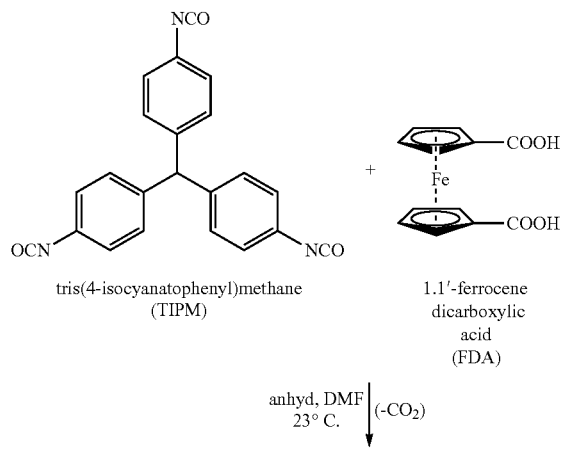

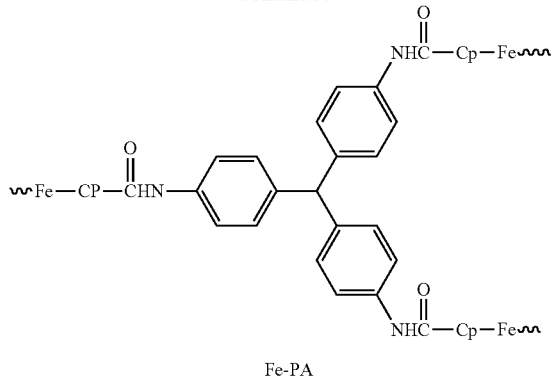

Fe-PA

Example 18

Conversion of Ferrocene Polyamide Aerogels (Fc-PA) to Iron Doped Carbon Aerogels (pFc-PA)

Fc-PA aerogels were transferred to MTI GSL1600X-80 tube furnace (tube made up of alumina 99.8% pure, 72 and 80 mm inner and outer diameters of the tube, 457 mm heating zone). The monoliths were heated at different temperatures ranging from 500 to 1400° C. under flowing $H_2$ gas (150 mL min$^{-1}$) for 5 h. The temperature of the furnace was slowly raised to desired temperature (500-1400° C.) at 5° C. min$^{-1}$. At the end the temperature of the furnace was programmed to lower down to room temperature at 5° C. min$^{-1}$ in $H_2$ atmosphere. As a control, samples were also treated at 800° C. under flowing Ar gas (150 mL min$^{-1}$) for 5 h.

Example 19

Acid Treatment of Carbon Supported Iron Aerogels (pFc-PA)

Carbon supported iron aerogels which were treated at 800° C. under hydrogen were further treated with 12.1 N concentrated HCl for 5 h while fresh HCl was replaced on hourly basis.

Example 20

Conversion of Iron Doped Carbon Aerogels to Graphitic Aerogels (gFc-PA)

Iron doped carbon aerogels produced at 800° C. as above were placed in a hot-zone graphite furnace (Thermal Technologies Inc., Model: 1000-3060-FP20) under inert atmosphere. The temperature was raised from room temperature to 400° C. at the rate of 40° C. min$^{-1}$ and then to 2300° C. at 10° C. min$^{-1}$. Monoliths were kept at that temperature for a period of 36 h. At the end, the power to the furnace switched off, and it was allowed to cool to room temperature at its normal rate (overnight).

Example 21

Methods

Pore-filling solvent exchange with liquid $CO_2$ was conducted in an autoclave (SPI-DRY Jumbo Supercritical Point Dryer, SPI Supplies, Inc. West Chester, Pa.). At the end, liquid $CO_2$ was taken out as a supercritical fluid (SCF). Liquid $^1H$ and $^{13}C$ NMR experiments were conducted with a 400 MHz Varian Unity Inova NMR instrument. Elemental analysis was conducted using a Perkin Elmer elemental analyzer (Model 2400 CHN). Chemical characterization of Fc-PA aerogels was conducted with infrared and solid-state $^{13}C$ NMR spectroscopy. Infrared (IR) spectra were obtained in KBr pellets, using a Nicolet-FTIR Model 750 Spectrometer. Solid-state $^{13}C$ NMR spectra were obtained with samples ground into fine powders on a Brucker Advance 300 Spectrometer with a carbon frequency of 75.475 MHz, using magic angle spinning (at 7 kHz) with broadband proton suppression and the CPMAS TOSS pulse sequence for spin sideband suppression. $^{13}C$ NMR spectra were referenced externally to glycine (carbonyl carbon at 176.03 ppm). Bulk densities of aerogels ($\rho_b$) were calculated, whenever possible, from the weight and the physical dimensions of the samples. Skeletal densities ($\rho_s$) were determined with helium pycnometry, using a Micrometrics AccuPyc II 1340 instrument. Porosities, Π, were determined from $\rho_b$ and $\rho_s$ via $\Pi=100\times[(\rho_s-\rho_b)/\rho_s]$. Surface areas and pore size distributions were measured by $N_2$ sorption porosimetry, using a Micrometrics ASAP 2020 surface area and porosity analyzer. Samples for surface area and skeletal density determination were outgassed for 24 h at 80° C. under vacuum before analysis. Average pore diameters were determined by the $4\times V_{Total}/\sigma$ method, where $V_{Total}$ is the total pore volume per gram of sample and $\sigma$, the surface area determined by the Brunauer-Emmett-Teller (BET) method. $V_{Total}$ was either taken from the highest volume of $N_2$ adsorbed along the adsorption isotherm, or it was calculated via $V_{Total}=(1/\rho_b)-(1/\rho_s)$. Scanning electron microscopy (SEM) was conducted with Au—Pd coated samples on a Hitachi Model S-4700 field-emission microscope. Thermogravimetric analysis (TGA) was conducted under air or $N_2$ with a TA Instruments model TGA Q50 thermogravimetric analyzer at a heating rate of 10° C. min$^{-1}$. The structure of the fundamental building blocks of the materials was probed with small-angle X-ray scattering (SAXS), using 2-3 mm-thick disks, 0.7-1.0 cm in diameter. SAXS was carried out with a PANalytical X'Pert Pro multipurpose diffractometer (MPD), configured for SAXS using Cu Kα radiation (λ=1.54 Å) and a 1/32° SAXS slit and a 1/16° anti-scatter slit on the incident beam side, and 0.1 mm anti-scatter slit and Ni 0.125 mm automatic beam attenuator on the diffracted beam side. The samples were placed in circular holders between thin Mylar™ sheets and scattering intensities were measured with a point detector in transmission geometry by 2 Theta scans ranging from −0.1 up to 5°. All scattering data are reported in arbitrary units as a function of Q, the momentum transferred during a scattering event. Data analysis was conducted according to the Beaucage's Unified Model, applied with the Irena SAS tool for modeling and analysis of small angle scattering within the commercial Igor Pro application (scientific graphing, image processing, and data analysis software from Wave Metrics, Portland, Oreg.). The crytallinity of the Fc-PA aerogels samples was determined X-ray diffraction (XRD) using a PANalytical X'Pert Pro diffractometer with Cu Kα radiation and a proportional counter detector equipped with a flat graphite monochromator. Transmission Electron Microscopy (TEM) was conducted with an FEI Tecnai F20 instrument employing a Schottky field emission filament operating at a 200 kV accelerating voltage. Raman spectroscopy of the carbon samples was conducted with a Jobin-Yvon micro-Raman spectrometer with a 632.8 nm He—Ne laser as the excitation source.

Example 22

Materials Characterization

Material Characterization data is summarized in Table FA-1. Monoliths shrink significantly within the range of 35% to 40% as an inverse function of monomer concentration. Interparticle covalent bonding gets more pronounced due to higher monomer concentration; therefore less shrinkage. Supercritical drying in $CO_2$ is solely responsible for all the shrinkage observed, no shrinkage observed during gelation and aging (syneresis) or even in solvent exchange. The linear increase in bulk density ($\rho_b$) from (0.123-0.490 g cm$^{-3}$) confirms that all the monomer is incorporated in the final Fc-PA aerogel. Skeletal densities ($\rho_s$) fall in range of 1.33-1.47 g cm$^{-3}$. Porosity (Π) values, which are calculated from ($\rho_b$) and ($\rho_s$), decreases from 92% to 63% as the bulk density increases (see Table FA-1). Irrespective of shrinkage all Fc-PA aerogels are highly porous.

pores which characterizes Fc-PA aerogels to be closely packed materials at higher densities. Low density Fc-PA aerogels adsorb substantial volume of $N_2$, attributed to their microporosity, which decreases as the density increases. The microporosity is not related to the empty spaces between closely packed primary particles but rather to an inherent property of the polymer itself, attributed to the molecular rigidity of structure of TIPM monomer (intrinsic microporosity).

The surface area (σ) of Fc-PA aerogels, determined by Brunauer-Emett-Teller (BET) analysis, yields high surface area (456 m$^2$ g$^{-1}$) for low density aerogel with only 47% σ attributed to micropores (via t-plot analysis by Harkins and Jura Model) while σ ultimately reduces to 258 m$^2$ g$^{-1}$ for high density samples with microporosity of about 17%. Quantitatively, the average pore diameter can be calculated using the relationship: $4 \times V_{Total}/\sigma$ either by using as $V_{Total}$ the maximum volume adsorbed from the isotherms taking in account only the mesopores or by $V_{Total}$ calculated by single point adsorption of the peak maxima capturing all pores by using the relationship, $V_{Total} = (1/\rho_b) - 1(1/\rho_s)$ (see Table FA-1). These quite different values progressively get closer as bulk density increases, as expected by closely packed spheres of dense materials.

TABLE FA-1

Materials characterization data for Fc-PA Aerogels.

| sample- % w/w solids | linear shrinkge (%)[a,b] | bulk density, $\rho_b$ (g cm$^{-3}$)[a] | skeletal density, $\rho_s$ (g cm$^{-3}$)[c] | porosity, Π (% v/v) | Specific pore volume (cm$^{-3}$ g$^{-1}$)[d] | | | BET surf. area, σ (m$^2$ g$^{-1}$) | av. pore diameter, (nm) | | particle diameter (nm)[g] |
|---|---|---|---|---|---|---|---|---|---|---|---|
| | | | | | $V_{Total}$ | $V_{1.7-300\,nm}$ | $V_{>300\,nm}$ | | $4 \times V_{Total}/\sigma$[e] | BJH[f] | |
| Fc-PA-5 | 41 ± 0.50 | 0.123 ± 0.006 | 1.472 ± 0.004 | 92 | 7.451 | 1.448 | 6.003 | 456 | 14(67) | 40[63] | 8.7 |
| Fc-PA-10 | 39 ± 0.09 | 0.202 ± 0.008 | 1.342 ± 0.006 | 85 | 4.205 | 2.360 | 1.845 | 381 | 25(45) | 32[14] | 11 |
| Fc-PA-15 | 38 ± 0.03 | 0.340 ± 0.004 | 1.333 ± 0.005 | 74 | 2.196 | 2.084 | 0.112 | 377 | 22(23) | 39[18] | 11 |
| Fc-PA-20 | 37 ± 0.70 | 0.401 ± 0.003 | 1.363 ± 0.003 | 70 | 1.760 | 0.829 | 0.931 | 276 | 12(26) | 16[4.8] | 15 |
| Fc-PA-25 | 35 ± 0.10 | 0.490 ± 0.007 | 1.341 ± 0.005 | 63 | 1.295 | 0.719 | 0.576 | 258 | 12(26) | 12[4.7] | 17 |

[a]Average of 4 samples.
[b]Shrinkage = 100 × (mold diameter − sample diameter)/(mold diameter).
[c]Single sample, average of 50 measurements.
[d]$V_{Total}$ was calculated via $V_{Total} = (1/\rho_b) - (1/\rho_s)$, $V_{1.7-300}$ nm from $N_2$-desorption volume. $V_{>300}$ nm = $V_{Total} - V_{1.7-300}$ nm.
[e]Average pore diameter is calculated by $4 \times V_{Total}/\sigma$ method, For first number, $V_{Total}$ was calculated by the single-point adsorption method; for the number in brackets, $V_{Total}$ was calculated via $V_{Total} = (1/\rho_b) - (1/\rho_s)$.
[f]From the BJH plots: first numbers are the peak maxima; numbers in brackets are widths at half maxima.
[g]Particle diameter = $6/(\rho_s \times \sigma)$.

Example 23

$N_2$ Sorption

Figure 11:
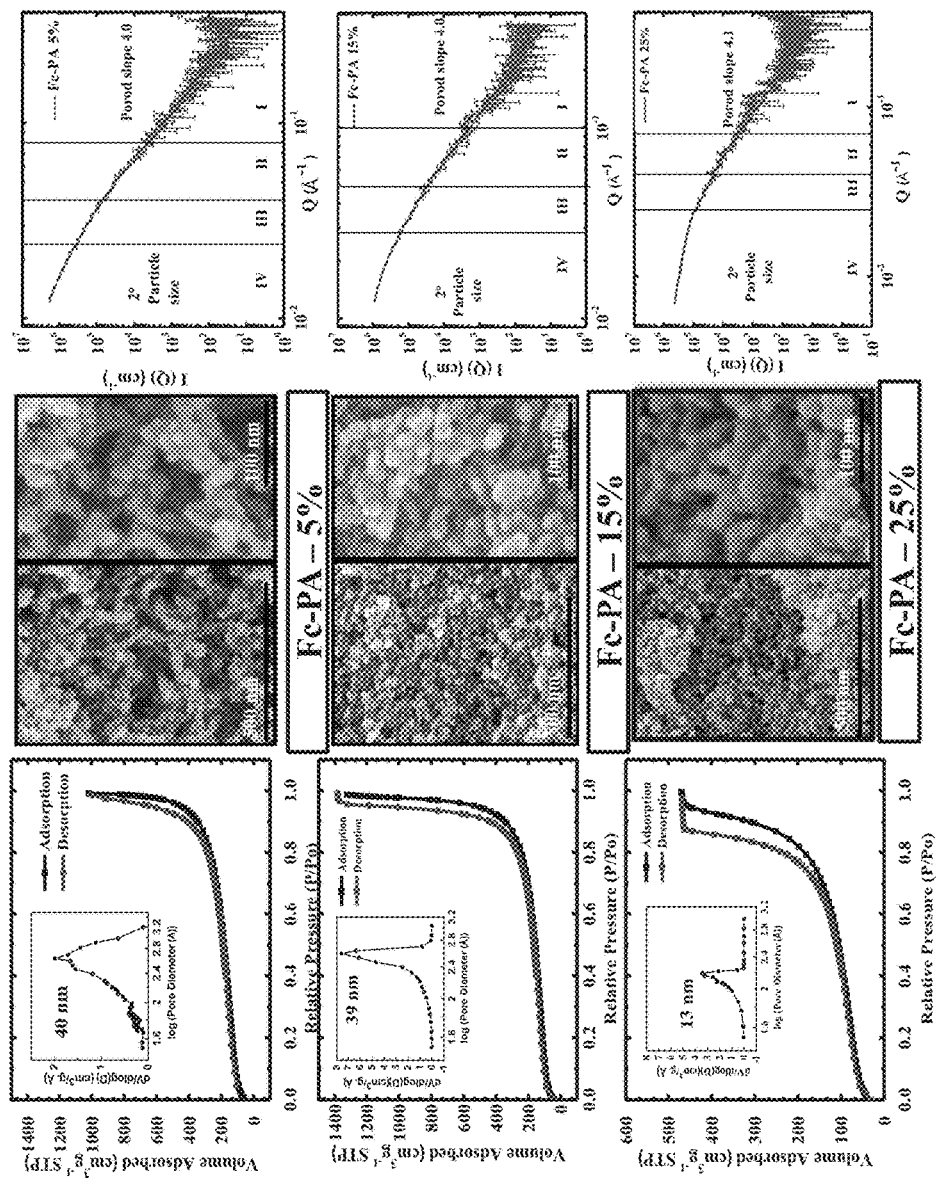
FIG. 11 displays the BET isotherms, SEM micrographs and SAXS plots for Fc-PA at 5%, 15% and 25%, respectively.

The pore size distribution of Fc-PA aerogels is evaluated semi-quantitatively by $N_2$ sorption porosimetery. Representative data is shown in FIG. 11. $N_2$-Sorption show type IV isotherms suggesting Fc-PA aerogels to be mesoporous materials. At lower densities (≤0.34 g cm$^{-3}$) the $N_2$ sorption isotherms show significant volume absorbed at relative pressure P/P$_o$=0.9 and do not reach a well-defined saturation plateau indicating a significant portion of porosity to be macroporous (Fc-PA (5%) with an average pore diameter>67 nm), while isotherms at higher densities (>0.34 g cm$^{-3}$) have a pronounced desorption hysteresis loop reaching saturation at P/P$_o$=0.9 indicating mesoporosity. Considering these two extremes, data signifies a macroporous-mesoporous transition as the monomer concentration increases. As the bulk density increases (>0.34 g cm$^{-3}$), the onset of the quick rise in the volume of $N_2$ adsorbed at lower P/P$_o$ values (P/P$_o$≈0.8), the isotherm reaches saturation and shows H2-type hysteresis loop. All of these may be consistent with mostly mesoporous materials and "ink-bottle"-type The BJH methods applied to the desorption branch shown in inset (see FIG. 11), show broad pore size distributions for Fc-PA aerogels of low density indicating macroporosity-mesoporosity, while high density aerogels yield narrow distributions indicating mesoporous materials. Fc-PA aerogels with high densities have isotherms that reach saturation. The average pore diameter determined by peak maxima of BJH pore size distribution agrees well with the values calculated by $4 \times V_{Total}/\sigma$ method. The particle diameter determined by BET and SEM and SAXS analysis are in well agreement, hence particle diameter calculated via d=$6/\rho_s\sigma$ represents diameter of primary particle. The σ of Fc-PA aerogels is greater as compared to polyamide aerogels without ferrocene moiety while (σ) decreases as the monomer concentration increases in Fc-PA aerogels.

Example 24

SEM

The structural morphology of Fc-PA aerogels was determined with scanning electron microscopy. All samples have same appearance with fused nanobead particles, coral like structures, showing that all the Fc-PA aerogels consist of primary particles that are agglomerating together to form larger clusters, as the monomer concentration increases with an ease to discern the primary and secondary particle structural hierarchy.

In Fc-PA aerogels, SAXS plots in FIG. 11 have two Guinier regimes buried in between two power law regimes on the basis of Beaucage's unified model analysis indicating the ease for identification of different structural levels. All Fc-PA have a power law region (referred to as region I) showing slope≥4.0 at high Q scattering values.

TABLE FA-2

SAXS analysis of Fc-PA aerogels.

| | Primary Particles | | | Secondary Particles | | |
|---|---|---|---|---|---|---|
| Sample | high-Q slope [a] | $R_{G(1)}$ [b] (nm) | R(1) [c] (nm) | high-Q slope [d] | $R_{G(2)}$ [e] (nm) | R(2) [c] (nm) |
| Fc-PA 5% | −4.00 ± 0.01 | 4.3 ± 0.1 | 11.32 ± 0.2 | 2.7 ± 0.6 | 17.2 ± 0.1 | 44.80 ± 0.1 |
| Fc-PA 10% | −4.20 ± 0.01 | 7.9 ± 0.2 | 20.54 ± 0.1 | 3.4 ± 0.7 | 20.9 ± 0.2 | 54.35 ± 0.1 |
| Fc-PA 15% | −4.00 ± 0.02 | 4.9 ± 0.4 | 12.90 ± 0.2 | 3.3 ± 0.1 | 11.6 ± 0.1 | 30.00 ± 0.1 |
| Fc-PA 20% | | | | | | |
| Fc-PA 25% | −4.10 ± 0.01 | 8.6 ± 0.2 | 22.60 ± 0.1 | 3.7 ± 0.5 | 13.8 ± 0.2 | 35.80 ± 0.1 |

[a.] Slopes < −4.0, signifying primary particles with density-gradient boundaries, Slopes ≥ −4.0 signifying primary particles with no density-gradient boundaries.
[b.] Radius of gyration of primary particles, $R_G$ (1), from first Guinier knee (see FIG. 11).
[c.] Particle radii = $R_G/0.77$.
[d.] Mass/Surface fractal dimension of secondary particles, low-Q power-law along the scattering profile.
[e.] Radius of gyration of secondary particles, $R_G(2)$, from second Guinier knee (see FIG. 11).

The size of these particles was strongly influenced by the monomer concentration of the sample. At higher magnification, Fc-PA aerogels consist of primary particles within the range of ~8-22 nm in diameter (FIG. 11) while these primary particles join together to make the secondary particles in the range of ~50-100 nm as the monomer concentration increases. The textural properties are related to the size of aerogel microparticles, the smaller microparticles of Fc-PA aerogels give rise to a pore network containing wide range of pore including meso and macropores. Certain Fc-PA aerogels exhibit bumpy texture instead of finer structure (smaller particles) and seems to be surface fractal as suggested by SAXS analysis (Table FA-2). The particle diameter observed by SEM is in agreement with SAXS analysis and particle diameter calculated through skeletal density and BET surface area (see Table FA-1 and Table FA-2).

Example 25

SAXS

Small angle scattering was used to examine and quantitatively measure the structural changes at the molecular-level of skeletal frame work of Fc-PA aerogels. In a typical SAXS experiment, the scattering intensity I(q) is plotted versus the scattering vector q (nm$^{-1}$). FIG. 11 shows plots of I(Q) as a function of Q. In SAXS plot the knee region is referred to as "Guinier knee", Guinier scattering indicating two length scales. The curvature in the Guinier regime defines a length scale (Guinier radius or radius-of-gyration, Rg, in the case of independent scatters). Each Guinier knee is followed by a quasi-power law regime. The Guinier plot yields a radius of gyration that characterizes the size of the scattering particles, while the Porod plot yields an exponent that suggests a sub-structural dimensionality from which the overall particle shape can be guessed. Porod exponents between 1 and 3 describe mass fractals, while exponents between 3 and 4 indicate surface fractal number. The curves were fit using Beaucage's Unified Model to extract Rg, the power-law exponents, P, and the Guinier prefactors, G, and power-law prefactor, B, associated with each length scale.

The region adjacent to region I is Guinier knee region (referred to as region II) in all Fc-PA aerogels, Guinier knee yields a radius of gyration of primary particles ($R_G(1)$), the radii is related to radius of gyration through following equation, $R_{G(1)}=0.77 \times R_{(1)}$ summarized in Table FA-2. At low Q scattering values, after the first Guinier knee (region II) comes the second power law region (referred as region III) followed by the second Guinier region (referred as region IV) in all Fc-PA aerogels with the slope approximately ≥3.0, indicating that primary particles form densely packed surface fractal secondary particles with the exception of Fc-PA (5%) (where slope is 2.7) fractal dimension. Radius of gyration for secondary particles ($R_G$ (2)) is obtained from Guinier knee of region IV which enables us to calculate the radii of the secondary particles via equation (see Table FA-2). The size of the particles increases with increasing the monomer concentration as shown in Table FA-2 because the size is related to $R_G$. In case where the particle size is small the surface area is large.

Example 26

Pyrolysis of Fc-PA Aerogels to Iron Doped Carbon Aerogels (pFc-PA)

Fc-PA aerogels were pyrolyzed from 500 to 800° C. for 5 hours under H$_2$ 150 mL/min, Samples (15% w/w) were selected for pyrolysis on basis of sturdiness of monoliths without sacrificing the BET surface area and porosity. The XRD pattern of 500-700° C. samples shows a broad peak of amorphous carbon (2θ 24.8°), while the covalently bonded ferrocene moieties were also reduced to Fe (2θ 44.7°) and Fe$_3$C (2θ 44.9°) as a result of the reducing environment during pyrolysis. The reduced iron particles are responsible for the partial graphitization of Fc-PA aerogels. The pFc-PA-800° C. aerogels exhibited a graphitic peak (2θ 26.2°) indicating low temperature graphitization. Graphitization is directly proportional to temperature, in the presence of iron catalytic particles. Further sample pyrolysis was conducted in the range of 800-1400° C. Resulting materials were compared with the original Fc-PA aerogels. Samples were not conductive until 800° C.

During pyrolysis in temperature range 800-1400° C., the pFc-PA aerogels undergo catalytic graphitization, where metal-containing precursors first reduced into metal nanoparticles, which then catalyze and aromatize carbonaceous materials into graphitic structures. During heat treatment, the carbon dissolves into the iron. When the carbon dissolution reaches saturation, carbon precipitates from the Fe—C solid and deposits on the surface of the iron nanoparticles and forms a graphitic shell. Yet another explanation is, as iron catalytic particles grow larger, more and more catalytically active surface area is created, and eventually a graphitic shell or other structures not associated with the growing nanotubes will begin to form from the iron particle. Eventually the iron particle will become covered with carbon, with no carbon nanotubes observed. The precipitation of the graphene layers is endothermic (40.5 kJ/mol) and the precipitated graphite shell could act as a thermal barrier, the local temperature will be decreased. The cooling further stimulates carbon to precipitate due to the reduced solubility of carbon in iron. The whole process of dissolution-precipitation would take place synchronously and continuously as long as the equilibrium is attained between heat loss from the carbon precipitation and heat supply from the surroundings. As a result, carbon encapsulated iron nanoparticles (CENP's) are formed. The resultant nanoparticles with well-ordered graphitic shells have a strong resistance to environmental degradation effects such as oxidation in air.

The formation of carbide depends upon the ratio of iron metal to carbon present in a material as predicted by phase diagram of iron systems. The carbides formed from three metals (Fe, Co and Ni) are of cementite phase ($Fe_3C$, $Co_3C$ and $Ni_3C$) and are thermodynamically metastable. The affinity of the metal toward carbon and the enthalpy of formation of carbides influences the formation as well as quantity of carbides. On the basis of order of enthalpy: Fe—C<Co—C<Ni—C, it may be concluded that it is easier for iron to form carbides as compared to Co and Ni.

suggesting developed mesoporosity characterized by large irregular mesopores as seen by SEM, instead of the narrow hysteresis loop observed in the parent Fc-PA aerogels. The adsorption branches rising above $P/P_o$=0.9 of pFc-PA aerogels at 800° C. and 1000° C. do not show a saturation plateau and are broad indicating irregular mesopores observed as flaky structures in SEM micrographs. The large $N_2$ adsorption uptake at $P/P_o$=0.9 is typical for nanosized materials, when adsorption for high relative pressures also occur on the outer surface of the nano particles. As the temperature increases, BET surface area decreases as a result of decreased microporosity in pFc-PA aerogels (Table FA-3). Iron particles induce graphitization in carbon and become crystalline (see XRD) at higher temperatures. The graphitized carbon thus increases the overall crystallinity of the samples, which is responsible for loss in microporosity and making them mesoporous materials with pore diameter less than 50 nm. (see Table FA-3). The pFc-PA aerogels shrink significantly within the range of 68-86% as temperature increases, but they retain a monolithic shape and morphology. The bulk density ($\rho_b$) of pFc-PA aerogels is less than the parent aerogels e.g., in the case of 800° C. owning to increased shrinkage due to mass loss during pyrolysis in the form of gases evolved. Consequently, the microporosity and skeletal density ($\rho_s$) along with BET surface area increases at 800° C. Skeletal densities first decrease as the treatment temperature increases, then increases for 1000-1400° C. (see Table FA-3). The broad range of $\rho_s$ covers 1.89 g $cm^{-3}$-2.0 g $cm^{-3}$ for amorphous carbon and 1.5 g $cm^{-3}$ for glassy carbon like materials. BET surface areas decreased dramatically mainly after heating at 1400° C., indicating a large shrinkage of the microporosity accessible to $N_2$. The release of volatile matter during carbonization generally produces an increase in larger mesopores volume and reduction in surface area suggesting that shrinkage of the porous texture of a carbon aerogel takes place mainly in the micropore range.

TABLE FA-3

Materials characterization data for pFc-PA aerogels.

| sample-% w/w solids | linear shrinkge | bulk density, | skeletal density, | porosity, Π | Specific pore volume ($cm^{-3}$ $g^{-1}$)[d] | | | BET surf. area, σ | av. pore diameter, (nm) | | particle diameter |
|---|---|---|---|---|---|---|---|---|---|---|---|
| pFc-PA-$H_2$ | (%)[a,b] | $\rho_b$ (g $cm^{-3}$)[a] | $\rho_s$ (g $cm^{-3}$)[c] | (% v/v) | $V_{Total}$ | $V_{1.7-300\ nm}$ | $V_{>300\ nm}$ | ($m^2$ $g^{-1}$) | 4 × $V_{Total}$/σ[e] | BJH[f] | (nm)[g] |
| 800 | 68 ± 0.50 | 0.286 ± 0.004 | 2.40 ± 0.004 | 88 | 3.086 | 0.705 | 2.381 | 369 | 9(33) | 18[9.48] | 7 |
| 1000 | 69 ± 0.02 | 0.812 ± 0.008 | 1.89 ± 0.006 | 53 | 0.702 | 0.238 | 0.464 | 235 | 5(10) | 4[0.28] | 13 |
| 1200 | 83 ± 0.50 | 0.720 ± 0.004 | 1.49 ± 0.005 | 51 | 0.718 | 0.562 | 0.156 | 234 | 10(13) | 16[1.88] | 17 |
| 1400 | 86 ± 0.50 | 0.981 ± 0.003 | 3.56 ± 0.003 | 72 | 0.740 | 0.227 | 0.513 | 84 | 11(35) | 13[2.63] | 20 |

[a] Average of 4 samples.
[b] Shrinkage = 100 × (mold diameter − sample diameter)/(mold diameter).
[c] Single sample, average of 50 measurements.
[d] $V_{Total}$ was calculated via $V_{Total}$ = (1/$\rho_b$) − (1/$\rho_s$), $V_{1.7-300\ nm}$ from $N_2$-desorption volume. $V_{>300\ nm}$ = $V_{Total}$ - $V_{1.7-300\ nm}$.
[e] Average pore diameter is calculated by 4 × $V_{Total}$/σ method, For first number, $V_{Total}$ was calculated by the single-point adsorption method; for the number in brackets, $V_{Total}$ was calculated via $V_{Total}$ = (1/$\rho_b$) − (1/$\rho_s$).
[f] From the BJH plots: first numbers are the peak maxima; numbers in brackets are widths at half maxima.
[g] Particle diameter = 6/($\rho_s$ × σ).

Example 27

$N_2$ Sorption

Figure 12:
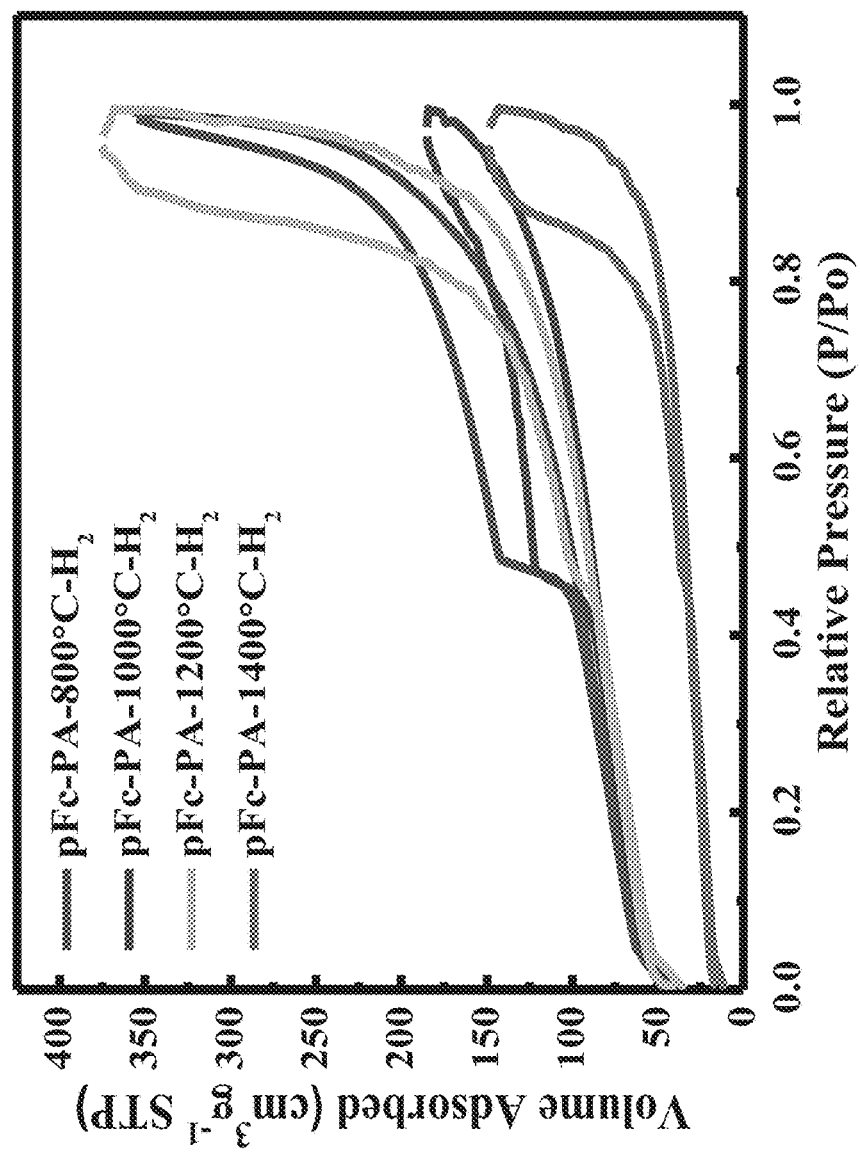
FIG. 12 displays the $N_2$ sorption curves of pyrolized Fc-PA (pFc-PA) aerogels at 800-1400° C.

The $N_2$ adsorption-desorption isotherm of pFc-PA aerogels within the temperature range of 800-1400° C. (see FIG. 12) show type IV adsorption isotherm with hysteresis loop H3 indicating capillary condensation within the mesopores. All samples have broad hysteresis loop with $P/P_o$~0.45-0.99

Example 28

TEM

Figure 13:
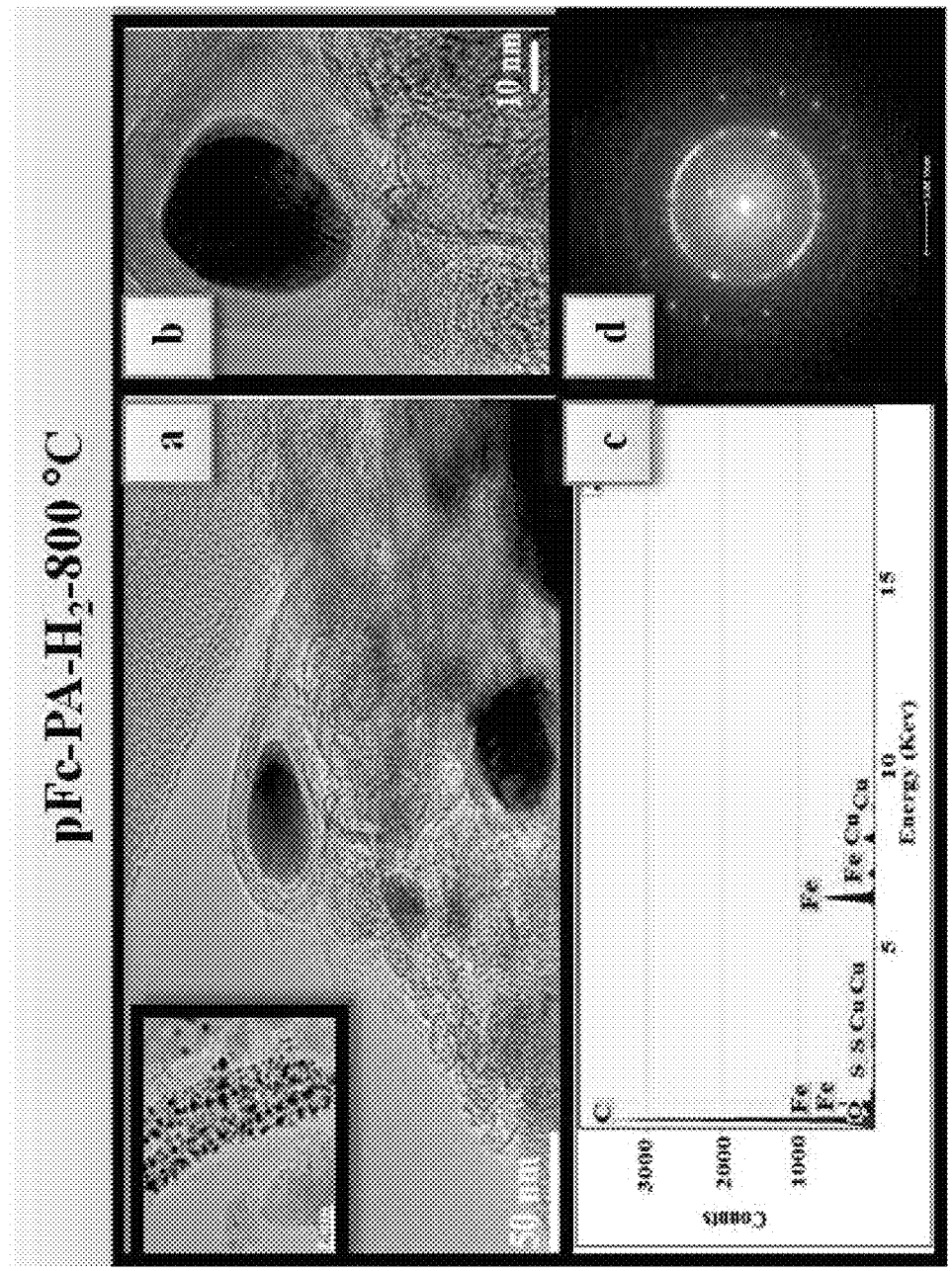
FIG. 13 displays the following: A) TEM of pFc-PA-800° C. exhibiting CENPs~25 nm in size embedded in amorphous carbon; inset showing homogeneous distribution of iron nano-particles; B) HRTEM of CENPs; C) EDX of CENPs; D) SAED pattern of nano-crystalline graphite.

TEM images of carbonaceous structures present in the temperature range 800-1400° C., are capsules and graphitic ribbons which are long, entangled and randomly bent (see FIG. 13). Carbon encapsulated iron nanoparticles (CENPs) predominate at 800-1400° C., ferromagnetic Fe particles making the core particles of diameter 20-25 nm encapsulated with a few graphene layers. The outer shell of CENPs average width, about 4-5 nm, varies from particle to particle. Along with CENPs nano graphitic ribbons are present at 1200-1400° C. Calculated La values indicate the thickness is only a few graphene layers. The number of graphene layers increases as the pyrolysis temperature increases (FIG. 13). The catalytic Fe particles are mostly spherical but some elliptical particles are also observed. The different curvatures of the graphitic ribbons is caused by the shape of the metallic particles formed during pyrolysis as suggested elsewhere by the published literature.

The high resolution transmission electron microscopy (HRTEM) is used to elucidate the microstructural changes in the morphologies of the pFc-PA aerogels with increasing temperature. HRTEM micrographs of pFc-PA aerogels in FIG. 13, suggests nanocapsules and nano ribbons are made up of multiwall graphene, at 800° C.~10 layers, at 1000° C.~16. CENPs do not undergo coalescence because of the graphitic shells, further supporting the homogenous distribution of iron particles throughout the aerogel. The SAED pattern confirms the crystalline structure of graphitic nanocrystals. The graphene layers are more ordered around the surface of the catalyst as compared to the outer disordered layers. Graphitic shell prevents sintering of iron and hinders the extent of catalytic graphitization. The $d_{002}$ spacing at 800-1400° C. indicates hexagonal graphitic structures (Table FA-4). The EDX analysis confirms the presence of an iron core of CENPs with XRD confirmation of the crystallinity of these ferromagnetic iron particles. (see XRD section).

Example 29

SEM

Figure 14:
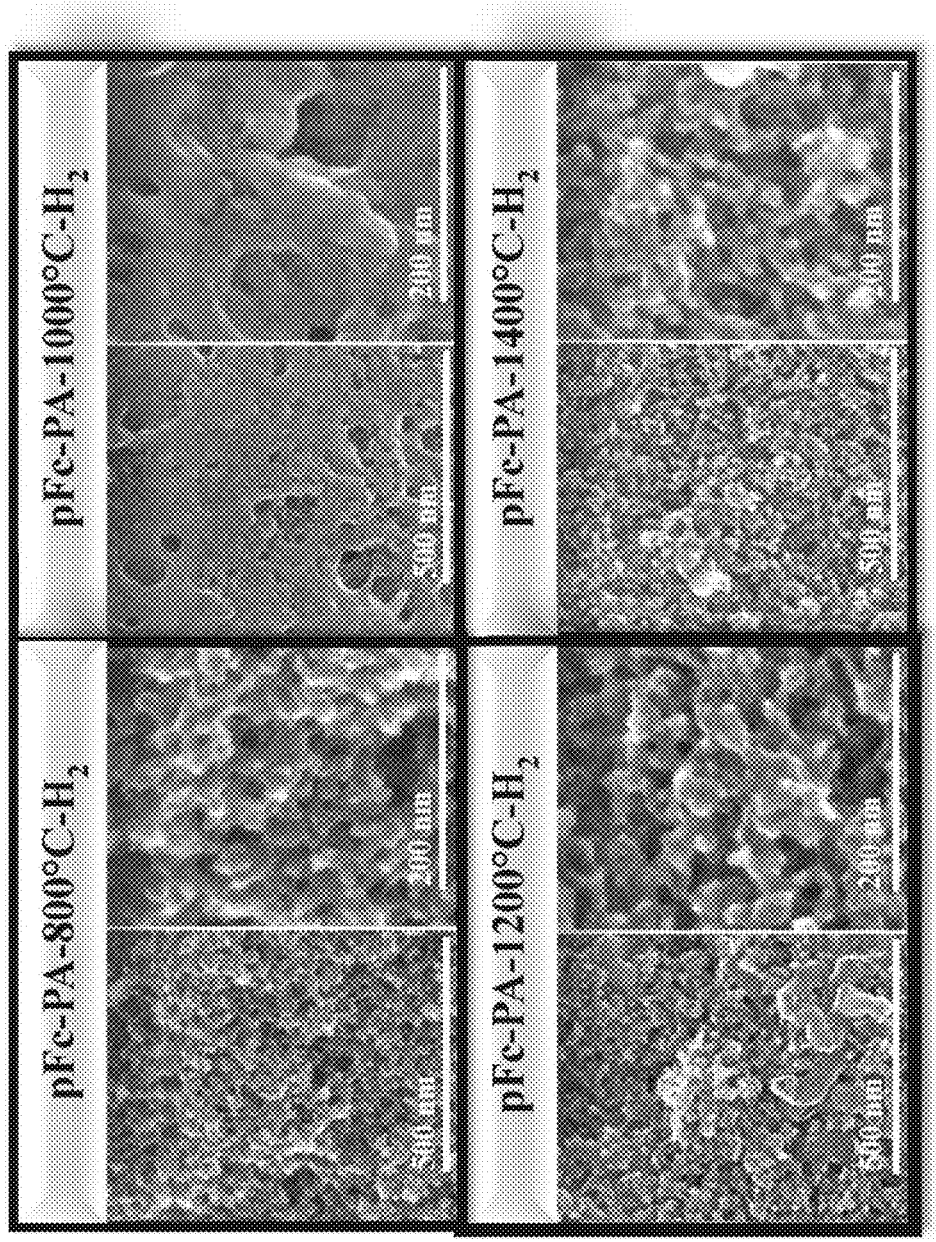
FIG. 14 displays SEM micrographs of internal pore structure of pFc-PA (800-1400° C.).

SEM micrographs of pFc-PA aerogels (FIG. 14) show all samples have same fused nano-bead, coral like structures. All the pFc-PA aerogels consist of primary particles agglomerating together to form larger clusters. Higher magnification SEM micrographs of pFc-PA aerogels reveal the effect of heat treatment by the change in morphology (particulate to flaky structures). BET surface area decreases with increasing pyrolysis temperature indicating a decrease in porosity due to coalescence of micropores, observed in SEM micrographs. Pyrolysis in this range of temperatures, shows annealing Fc-PA and reorganization of the carbon structures, as observed by the change in particle diameter and increase in the size of aggregates (FIG. 14).

Example 30

XRD

Figure 15:
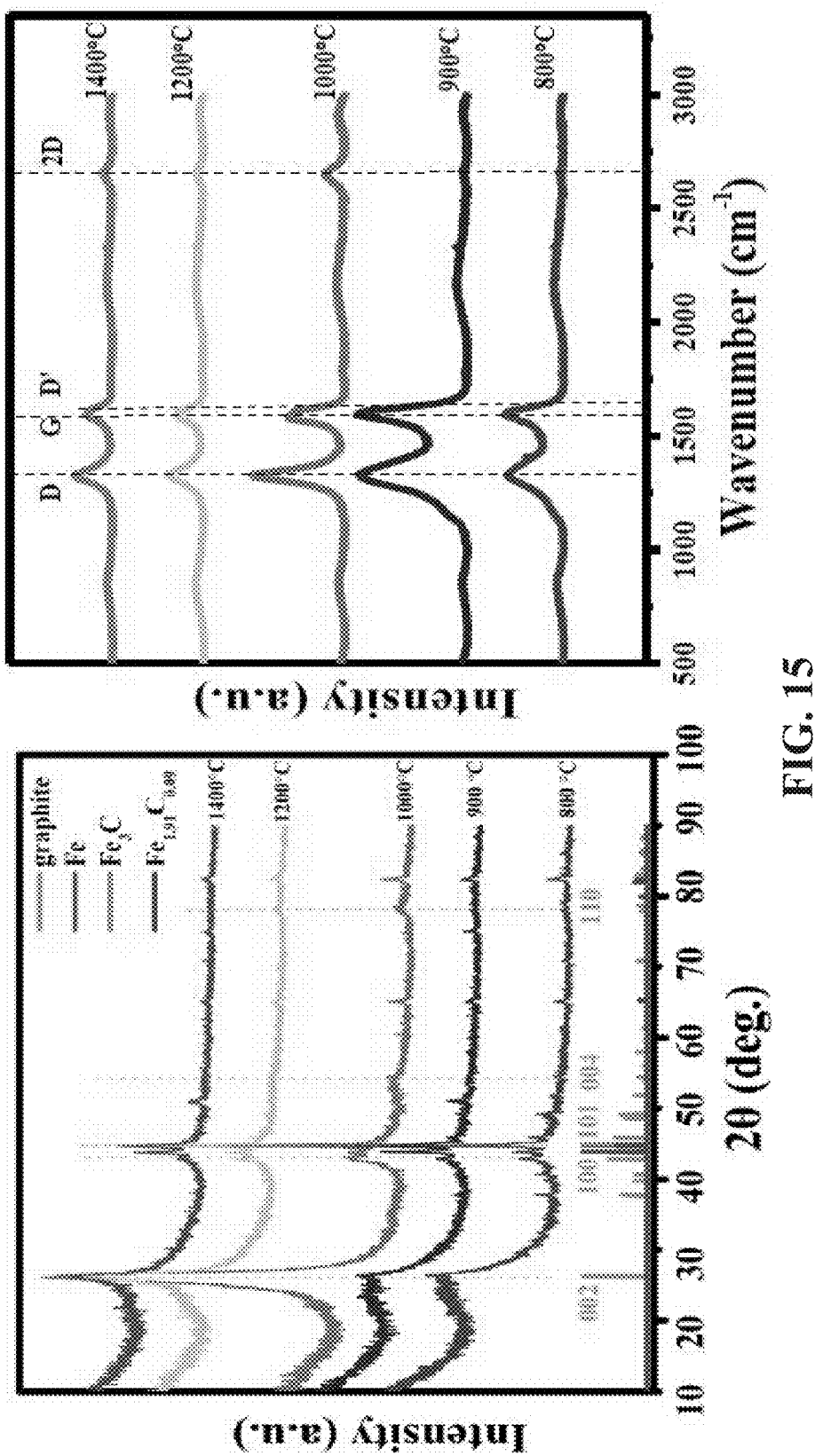
FIG. 15 displays the XRD pattern (left) and Raman spectra (right) of pFc-PA aerogels at 800-1400° C.
Figure 16:
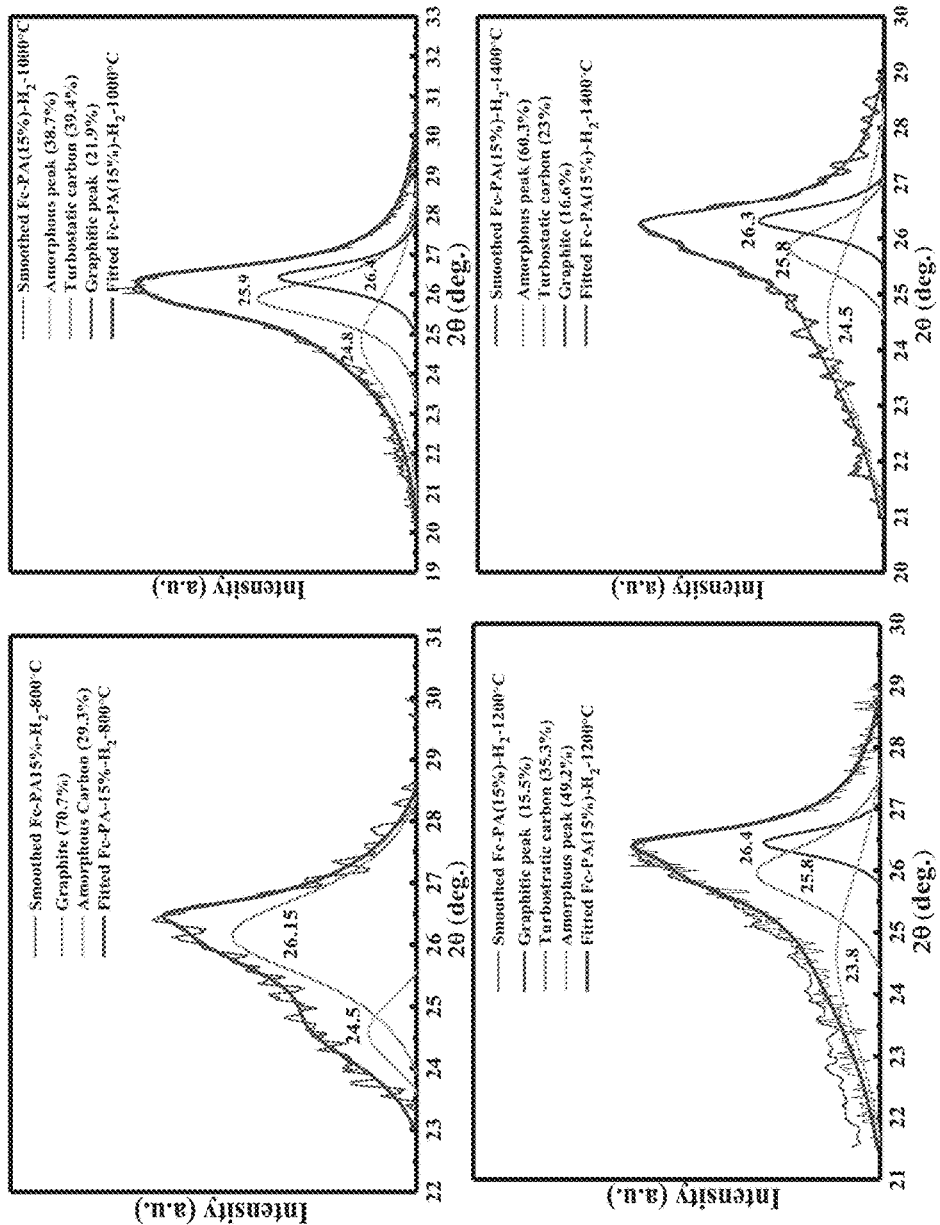
FIG. 16 displays the XRD peak fitting of pFc-PA aerogels at 800-1400° C.

XRD is employed for quantitative evaluation of temperature dependent structural changes in iron doped mesoporous aerogels with CENPs and to further verify the crystalline structure of CENPs. XRD profile of pFc-PA aerogels pyrolyzed in the range of 800-1400° C. are seen in FIG. 15. At low temperatures (500-700° C.) a broad peak centered at 2θ 24.8° is attributed to amorphous carbon. At high temperatures (700° C. to 800° C.), a peak at 2θ 26.24° indicates hexagonal planes of graphite. At 1000° C., the 002 reflection becomes sharp with increased intensity suggesting the well crystalline structure of CENPs which contains a significant amount of graphitic carbon. This evidence demonstrates the catalytic effect of metal on graphitization of carbon aerogels. The peak shift suggests the increasing alignment of a hexagonal layers in order with increasing pyrolysis temperature in the presence of iron catalyst. The diffractions at 2θ 41° and 46.6° are typical corresponding to cementite ($Fe_3C$) while 44.7°, 64.8° and 89.2° reflections fit well with diffractions of 110, 220 and 200 diffraction planes of cubic α-Fe. The results suggest no other iron phase is present.

At higher temperatures (1200-1400° C.), instead of the rise in the graphitic peak at 26.22°, it decreases in intensity and broadens indicating to smaller graphitic structures as suggested by crystallite size (see Table FA-4). It is attributed to the 86% shrinkage of the samples under $H_2$. In addition to metal and metal carbide peaks at 1400° C., another peak appears at 43.77° referring to a new phase, martensite ($Fe_{1.91}C_{0.09}$). Temperatures 1200-1400° C. induce early melting of iron nanoparticle instead of its iron's bulk melting temperature (1538° C.) and sintering of iron particles took place as observed in SEM. It hindered the graphitization process because the sintered particles were larger in size hence catalytic activity is decreased, which resulted in increased quantity of amorphous carbon.

Reduction in the full width at half maxima (FWHM) of 002 graphitic peak with increased temperature indicates an increase in crystallite size (Lc) of the graphite (Table FA-4), which indicates increase in crystalline order except at 1200-1400° C. In all cases, the 002 lattice fringe show a tail to the low angle side while peak tail of 101 diffraction towards high angle side. This data indicates the coexistence of crystalline graphite and less ordered carbon material, as observed in TEM and SEM. The interlayer spacing $d_{002}$ ($d_{002}$=1.54/2 sin θ) at all temperatures is shown in Table FA-4.

TABLE FA-4

XRD data analysis of pFc-PA Aerogels.

| pFc-PA-$H_2$ Sample | 2θ | $d_{002}$ (nm) | Lc (nm) | R-parameter | Amorphous Carbon (24°) | Turbostratic Graphite (25.5°) | Graphite (26.6°) |
|---|---|---|---|---|---|---|---|
| 800° C. | 26.24 | 0.339 | 5.3 | 2.22 | 29.3 | — | 70.7 |
| 1000° C. | 26.35 | 0.338 | 6.6 | 10.40 | 38.7 | 39.4 | 21.9 |
| 1200° C. | 26.41 | 0.337 | 4.2 | 10.04 | 49.2 | 35.3 | 15.5 |
| 1400° C. | 26.45 | 0.336 | 4.1 | 11.03 | 60.0 | 23.0 | 17.0 |

$d_{002}$ = 1.54/2sinθ and Lc is calculated by Scherer's equation by XRD instrument, R = B/A.

Metal precursors undergo a series of phase/state changes along with that of carbon precursor as a result mixture of Fe metal and $Fe_3C$ particles coexist in carbon matrix. Hydrogen reduces the iron to α-Fe at ~500° C. α-Fe reacts with the carbon to form cementite ($Fe_3C$), because hydrogen is a more powerful reducing agent than carbon. Black particles seen are α-Fe determined by EDX analysis. These samples show magnetic properties, they were attracted by a magnet at room temperature. This further asserts the dominance of metallic character of iron and iron carbide, but the ferromagnetic properties, were not observed until after 800° C. processing (see magnetization section). The catalytic effect of iron metal on graphitization of carbon aerogels is evident from the graphitization parameter R (fraction of graphite present as single layer) (see Table FA-4).

XRD patterns of pFc-PA-800° C. aerogels exhibit an asymmetric 002 Bragg peak as a combination of two or more reflections. This peak combination indicates the existence of more than two carbon phases. To determine the number of phases present, the 002 peak is fitted by Lorentzian peak fit at peaks 24°, 25.5° and 26.2° (amorphous, turbostratic and graphitic carbon respectively) (see Table FA-4). The samples pyrolyzed at different temperatures contain different concentration of phases present as the pyrolysis temperature increases. The sudden change in structure of Fc-PA aerogels at 1000° C. is attributed to the formation of new phase of carbon i.e. turbostratic graphite. The term turbostratic refers to the haphazard arrangement of the graphene sheets developed as a result of graphitization instead of their parallel stacking.

As the pyrolysis temperature increases, the width of 002 peak decreases indicating a decrease in crystallite size and the 101 band also splits into 100 and 101 peaks referring to the development of graphite stacking order.

Example 31

Raman

The Raman spectroscopy is an effective tool for determining the morphology of carbon nano structures as well as their crystalline state. Hydrogen flow rate 150 mL/min, and pyrolysis temperature between 800-1400° C., Fe particles responsible for carbon nanocapsules around Fe particles (for their structural details see FIG. 13). The Raman spectra of all pFc-PA aerogels in FIG. 15 show two main bands approximately around 1330 $cm^{-1}$ and 1590 $cm^{-1}$ characteristic of symmetry break down at the edge of graphene sheets. The band at 1590 $cm^{-1}$ is referred to as G-band characteristic of C—C bond stretching of Egg symmetry of graphite, the D-band at 1330 $cm^{-1}$ is assigned to breathing mode of $A_1g$ symmetry related to the disorder induced scattering resulting from imperfection or the loss of hexagonal symmetry of carbon nanostructures (measure of disorder in graphitic materials) and G' band at 2700 $cm^{-1}$ is attributed to the second order two phonon process, characteristic band in all graphitic materials. The D' peak at 1610 $cm^{-1}$ appears as shoulder peak of G-band is attributed to microcrystalline graphite. The D band is associated with vibrations of carbon atoms with dangling bonds in plane terminations of disordered graphite or glassy carbon. The D and G bands are present in various $sp^2$ materials and the frequency, strength, and line width of these bands is found to be a function of the degree of structural disorder. Shifts to lower frequency, as well as decrease in $I_D/I_G$ ratio, are frequently associated with the increase in degree of graphitization of carbonaceous materials. Only three broad peaks are visible in the Raman spectra from the 800° C.: sample 1326 $cm^{-1}$, 1592 $cm^{-1}$ and 2648 $cm^{-1}$ with almost equal $sp^2$ and $sp^3$ character. Disorder in carbonaceous material is due to tetrahedral carbon structures formed. The peak at 2648 $cm^{-1}$ is (2D) peak also referred to as G' peak, it is also related to the defects in the carbonaceous materials. The origin of G' peak assigned to a two phonon scattering process which connects two high symmetry points K and K' of the first Brillouin zone. The G-band of CENPs at 1590 $cm^{-1}$ exhibits a shift in peak as compare to the highly ordered pyrolytic graphite (HOPG) at 1580 $cm^{-1}$. The results are consistent with previous reports about Raman spectra of highly curved graphitic carbon capsules.

Figure 17:
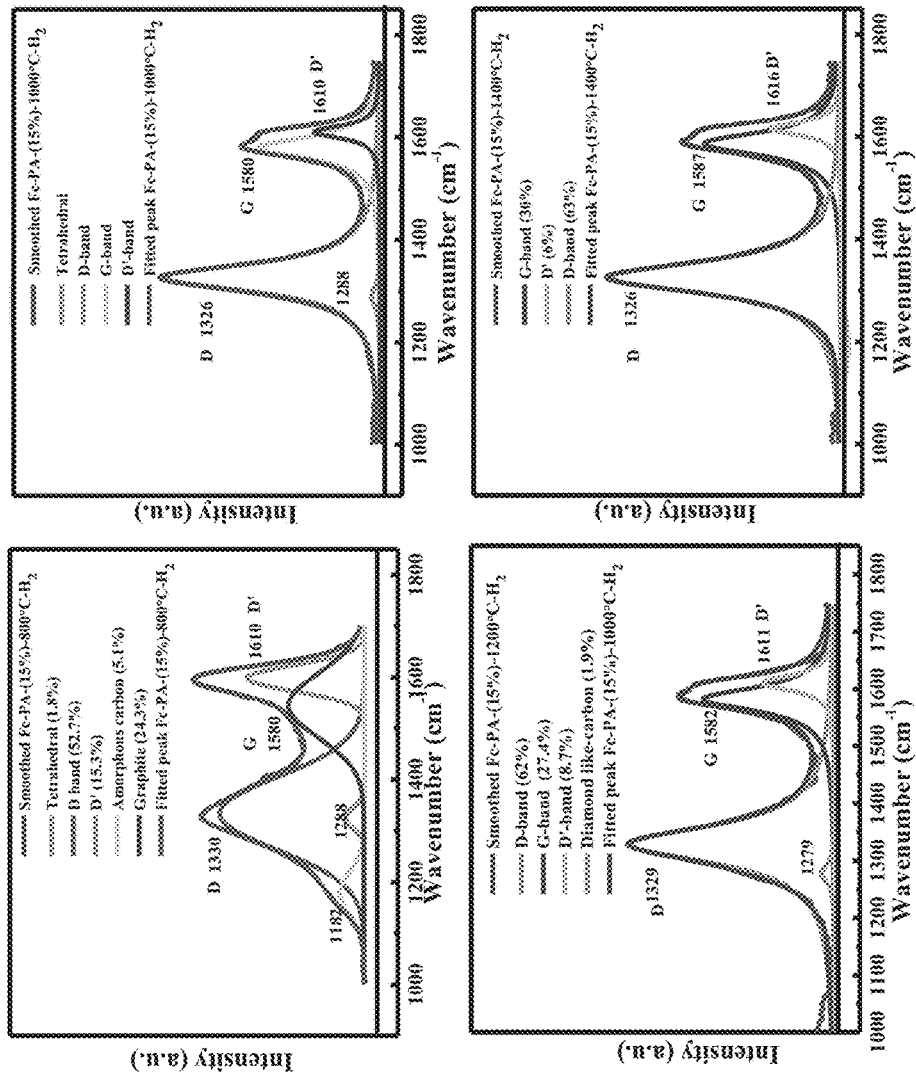
FIG. 17 displays the Lorentzian peak fitting of Raman D and G-bands of pFc-PA aerogels at 800-1400° C.

At 1000° C., there is a slight shift towards lower frequency with the D band at 1325 $cm^{-1}$ and G-band at 1588 $cm^{-1}$. A new peak appears as a shoulder of G-band at 1620 $cm^{-1}$ referred as D' band attributed to disorder while the peak at 2948 $cm^{-1}$ is referred as D+G band, overtone of D and G band. The Raman feature at about 2900 $cm^{-1}$ is associated with a D+G combination mode is also induced by disorder. The 2D band at 2648 $cm^{-1}$ does not resemble graphite or graphene instead it is more like turbostratic graphite. The increased intensity of D band is responsible for greater $sp^3$ character and reduction of $sp^2$ indicating more defects in the graphitic material. As the temperature increased the D peak intensity increases which confirms the increase in $sp^3$ character of the carbonaceous material. The second-order Raman mode (1800-2800 $cm^{-1}$) is an overtone of the D band and is characteristic of well graphitized carbon samples. The second order Raman spectra of carbonaceous materials have a peak at ~2600 $cm^{-1}$, the shape of which classifies the material as either graphite, graphene or turbostratic graphite. The relative intensity ratio, $I_D/I_G$ or relative area ratio, $A_D/A_G$ of D and G bands, is a measure of the degree of disorder in graphitic material. The greater the $I_D/I_G$ ratio the higher is the disorder. In pFc-PA aerogels the relative $A_D/A_G$ is measured by integrating the two bands with Lorentzian peak fitting (see FIG. 17) taking in to account the respective area of the peaks.

TABLE FA-5

Raman data analysis of pFc-PA Aerogels

| Sample | Peaks ($cm^{-1}$) | | | Calculated Parameters | |
|---|---|---|---|---|---|
| pFc-PA-$H_2$ | D | G | G' | $A_D/A_G$ | $L_a$ (nm) |
| 800° C. | 1326 | 1592 | — | 2.12 | 26.49 |
| 1000° C. | 1326 | 1594 | 2647 | 2.28 | 26.11 |
| 1200° C. | 1328 | 1590 | 2648 | 2.39 | 22.65 |
| 1400° C. | 1328 | 1590 | 2649 | 2.35 | 24.57 |

G, D and G' peaks represent respective peak heights,
$A_D/A_G$ is the ratio of area of G and D bands.
$L_a$ (nm) is the stack height of graphitic structures calculated by empirical Knights formula Example 32

Magnetization

The magnetic properties of pFc-PA aerogels were considered after they show attraction to magnet at room temperature. The iron is a fairly soft metal and becomes ferromagnetic at 770° C., the Curie point ($T_c$). As the iron passes through the Curie temperature there is no change in the crystalline structure, but there is a change in the magnetic properties as the magnetic domains begins to appear and may be aligned in the presence of external field.

Fc-PA aerogels show a paramagnetic behavior as demonstrated in FIG. 18. However, pFc-PA aerogels annealed at 800° C., termed as carbon encapsulated iron nanoparticles (CENPs), do show magnetic hysteresis loop (FIG. 18B). The calculated coercivity ($H_c$) is 436 Oe, which is much larger than that of bulk iron (~1 Oe). The substantial increase in $H_c$ as compared to the bulk Fe may be attributed to the size effect. It is well-known that when the size of the magnetic particle is reduced, the coercivity increases and becomes maximum when the size of the nanoparticles is comparable to the domain size.

Moreover, it is also reported that implantation of carbon and graphene also enhances the coercivity of Fe nanoparticles in the similar size range as exhibited by TEM images. pFc-PA-800° C.-$H_2$ show a core of alpha iron and iron carbide particles of diameter about 20-25 nm and a graphitic shell (4-5 nm thick) encapsulating the core particles. Hence it is very probable that some of the graphene may be set in the interstitial sites. Thus the enhanced coercivity of Fe nanoparticles was attributed to both the size as well as the incorporation of interstitial graphene.

The saturation magnetization (Ms) of pFc-PA-800° C. aerogel obtained from the hysteresis loop is approximately 6.20 emu/g which is far less than 224 emu/g for bulk iron metal. This is understandable as the samples herein contain both magnetic (Fe and $Fe_3C$) as well as nonmagnetic entities. Thus lowering the magnetization values. Furthermore, it is also well known that in case of small particles, the surface may contain a disordered structure and broken bonds that will form magnetically dead layers leading to lower magnetization values.

Example 33

Graphitization of Fc-PA Aerogels

Ferrocene polyamide aerogels (Fc-PA) were treated at 800° C. under $H_2$ (pFc-PA-$H_2$). These samples were selected for further investigations on the basis of higher surface area with well-developed porosity. pFc-PA-$H_2$ was treated with acid (pFc-PA-$H_2$-acid) aiming to get rid of iron nanoparticles to see structural differences among the two samples. Fc-PA aerogels were also treated under argon as a control at 800° C. (pFc-PA-Ar) to investigate the effect of pyrolysis environment on developing morphology. All of these samples show low temperature graphitization with different graphitic structures along with some percentage of amorphous phase as a function of their pyrolysis environment.

All of the pyrolyzed samples mentioned above were ultimately treated at 2300° C. at the rate of 10° C./min for 36 hours to assure complete graphitization (gFc-PA-$H_2$, gFc-PA-$H_2$-acid, gFc-PA-Ar). All the graphitized samples were compared for their extent of graphitization and structural morphology with a change in pyrolysis environment. The gFc-PA aerogels have graphitized regions along with turbostratic graphite. No amorphous carbon phase was observed in gFc-PA aerogels present in pFc-PA aerogels. The turbostratic graphite is generally regarded as a variant of hexagonal graphite. Both are stacked up by graphene layers with a regular spacing but different stacking ordering degree. Hexagonal graphite is an ordered AB stacking structure, but graphene layers of turbostratic graphite may randomly translate to each other and rotate about the normal of graphene layers. Since hexagonal graphite is a stable structure, the translation and rotation of graphene layers should change the interlayer spacing and shape of atomic layers. TEM, XRD and Raman are in well agreement with each other providing an evidence for low temperature graphitic structures transformation into well-developed hexagonal graphitic structures.

Example 34

TEM

TEM images of gFc-PA aerogels exhibit various graphitic features based on the pyrolysis atmosphere ($H_2$, $H_2$-acid and Ar). The nanocapsules dominating in pFc-PA-$H_2$ as shown in the FIG. 19C slowly transforms into graphitic nanoribbons in gFc-PA-$H_2$ (FIG. 19H) with increase in stack height (La) (Table FA-6). The CENPs are not stable at very high temperatures so in gFc-PA-$H_2$ they transformed into graphitic ribbons and iron core particles undergo melting, resulting into 2 nm sized nanoparticles seen in HRTEM (FIG. 19H) but below the detection limit of XRD (FIG. 22 (right)). The dominating graphitic features at gFc-PA-$H_2$ (FIG. 19(F,G,H)) are long entangled intertwined kinked graphitic ribbons (turbostratic graphite) along with few layered graphene sheets (FWLGS as graphitic carbon) as supported by R-parameter value from XRD (Table FA-8). HRTEM depicts the interlayer spacing distance ($d_{002}$) of approximately 0.334 nm in pFc-PA-$H_2$ and gFc-PA-$H_2$ corresponding to the (002) lattice fringe of graphite indicating well developed hexagonal lattices as supported by XRD and Raman. The selected area diffraction pattern (SAED) indicates the existence of crystalline material consistent with the XRD investigations of the sample, the degree of crystallinity is low at 800° C. and well developed indicating the hexagonal alignment of graphene sheets in a specific arrangement at 2300° C.

Figure 19:
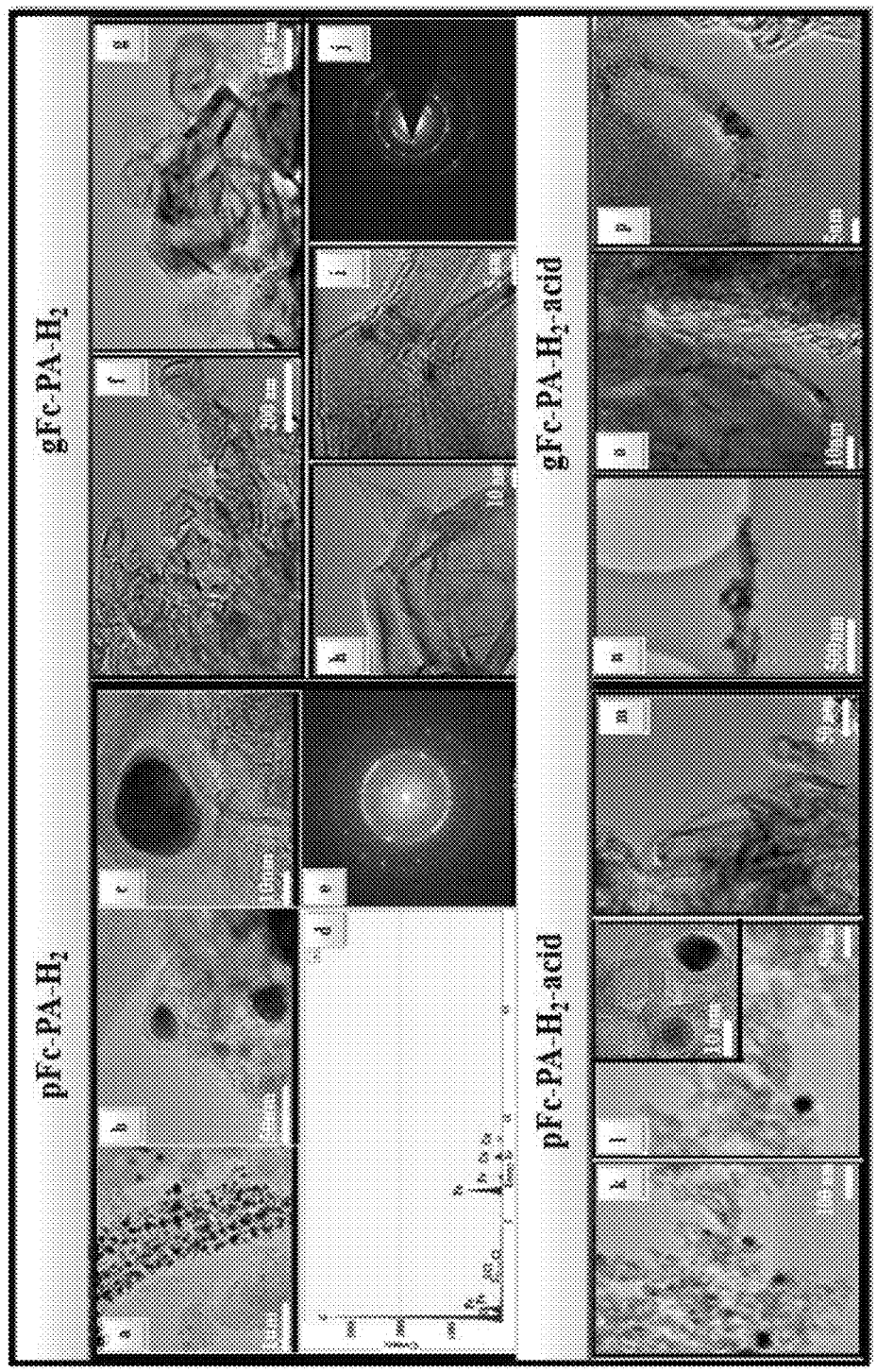
FIG. 19 displays the following: A) B) TEM images of pFc-PA-$H_2$ exhibiting CEMNPs along the edge with amorphous carbon~25 nm in size; C) HRTEM of CEMNPs; D) EDX of iron core of CEMNPs; E) SAED pattern of crystalline graphite; F) G) TEM images of gFc-PA-$H_2$; H) I) HRTEM of gFc-PA-$H_2$ with graphitic sheets and ribbons; J) SAED pattern of crystalline graphite; K) L) M) TEM images of pFc-PA-$H_2$-acid 1) inset shows hollow nano capsule and stable CEMNP; N) TEM image of gFc-PA-$H_2$-acid with DWNTs; O) P) HRTEM of graphitic ribbons with iron nanoparticles of 4-5 nm in size.

TEM images of pFc-PA-$H_2$-acid features hollow nanocapsules, graphitic nano ribbons along with stable CENPs (inset of FIG. 19L). This observation proves that the encapsulation was successful in pFc-PA-$H_2$. In other words, the carbon coating (a few nm in thickness) is impermeable and protects the encapsulated particles from acid leaching. The pFc-PA-$H_2$-acid contains empty carbon capsules, formed when the iron particles leaches from the metallic cores, which are encapsulated in the defected carbon coatings (turbostratic graphite). In case of gFc-PA-$H_2$-acid mixture of long straight and entangled CNTS (MWCNTS and DWCNTS as a special case of MWCNTS) were seen. Few iron nanoparticles of ~3 nm in size were trapped inside these tubes (FIG. 19(N,O,P)). Turbostratic graphitic ribbons were also observed in the sample.

Example 35

SEM

SEM micrographs of pFc-PA-$H_2$ aerogels (FIG. 20) features carbon fiber like material with some globular particles referred as spherical carbon on external surface of the monolith. The internal structure of pFc-PA-$H_2$ have coral like morphology indicating developed microporosity as supported by BET (Table FA-8). The gFc-PA-$H_2$ aerogels (FIG. 20) exhibit very different structures as compared to pFc-PA-$H_2$, where large graphitic sheets with hexagonal alignment and haphazardly scattered turbostratic graphene sheets can also be seen on the bare surface of aerogel, as demonstrated by TEM images. The internal structure of the graphitic aerogels shows flakey structure, indicating the development of sheet like material at high temperature. It is an evidence for loss of microporosity of gFc-PA-$H_2$ skeletal structure dominating at low temperature, indicating all the absorption is occurring at the external surface as supported by BET (Table FA-8).

In pFc-PA-$H_2$-acid, SEM micrographs (FIG. 20) contains fibers of limited length converse of pFc-PA-$H_2$ with long thread of carbon fibers and spherical carbon on the surface. The inner skeletal frame work of pFc-PA-$H_2$-acid exhibit large holes providing a concrete evidence of removal of iron particles after acid treatment. The SEM micrograph of external surface of gFc-PA-$H_2$-acid (FIG. 20) has larger graphene sheets with less turbostratic graphite as observed from R-parameter and Lorentzian peak fitting in XRD (Table FA-8). SEM micrograph of inner gFc-PA-$H_2$-acid also compliments the sheet like structures dominating on the surface. It also indicates a development of layered structure within the monolith. This suggests less iron to carbon ratio is required for development of few layered graphene sheets (FLGS).

Figure 20:
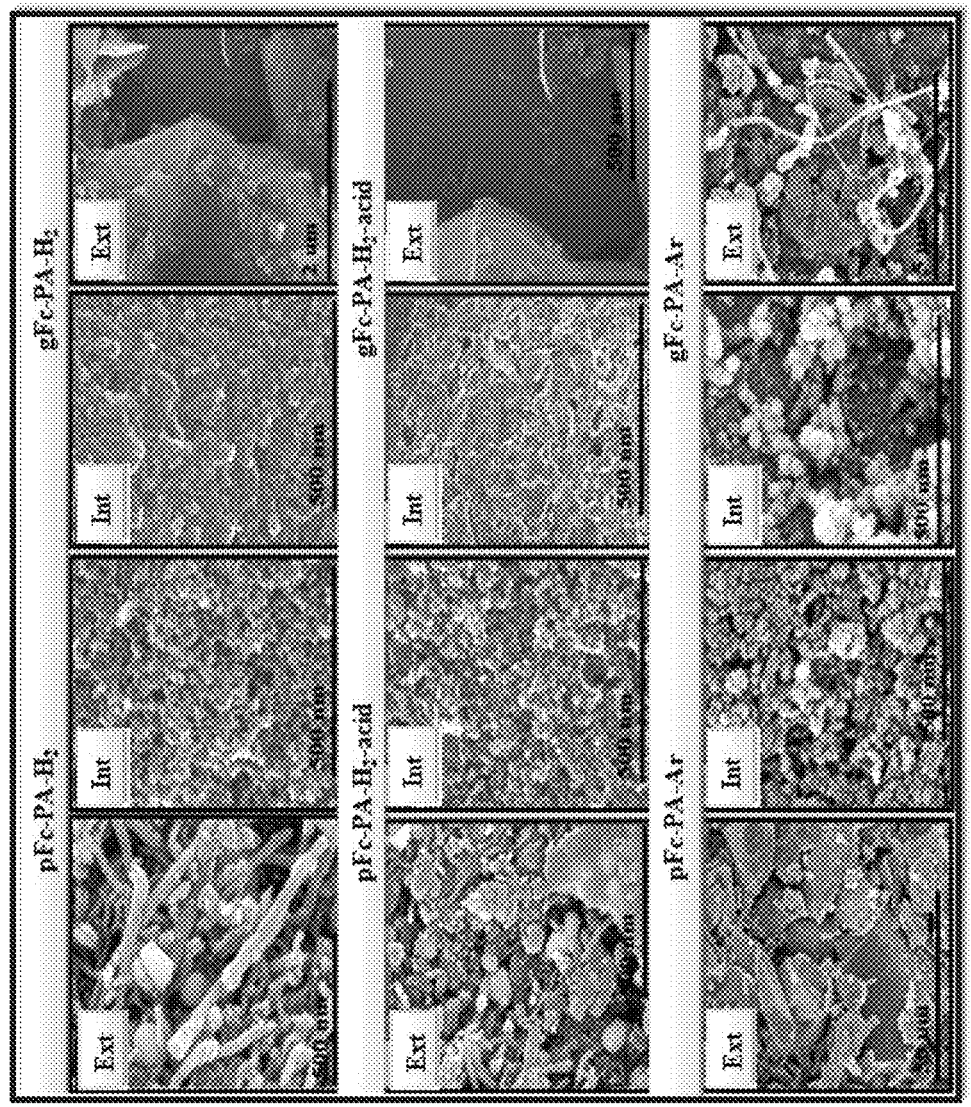
FIG. 20 displays SEM micrographs of pFc-PA and gFc-PA aerogels exhibiting surface graphitic structures and internal framework.

Bulk graphitic structures are clearly visible in SEM micrograph of pFc-PA-Ar on the external surface of monolith as supported by XRD analysis (Table FA-8) and Raman spectra. The internal structure of the monolith features developed porosity hence greater surface area. The gFc-PA-Ar show carbon nanotubes on the outer surface of aerogel which were not observed in case of pyrolyzed sample under $H_2$ (FIG. 20). The structural morphology is different on the basis of pyrolysis environment. In case of $H_2$ atmosphere, $H_2$ acts as a stronger reducing agent than carbon and is responsible for sheet like structures dominating the samples with some turbostratic graphite. In case of Ar carbon is the only reducing agent hence bulk graphitic structures with greater number of graphitic layers as supported by XRD and Raman.

Example 36

Raman

Raman spectroscopy is employed for evaluating the effect of pyrolysis conditions on the structural developments in pFc-PA aerogels when treated at high temperatures. All gFc-PA aerogels show three main peaks along with some nanostructural differences on the basis of environment provided (FIG. 21). The First order Raman spectra (1000-1800 $cm^{-1}$) show an asymmetric peak at 1588 $cm^{-1}$, referred to as G (graphitic band) responsible for Egg vibrational mode of hexagonal graphite (taking care of the vibrations of $sp^2$ hybridized carbon) atoms of graphitic layer. The second feature at 1330 $cm^{-1}$ referred to as D band is due to the $A_1g$ breathing mode of disordered $sp^2$ bonded carbon atoms, forbidden in pristine graphite, first observed and named by Tunistra and Koeing (J. Chem. Phys., 53:1126 (1970)). The 2D peak at 2600 $cm^{-1}$ is the most important feature of second order Raman spectra (1800-2900 $cm^{-1}$) and is characteristic of graphitic materials depending upon its shape and symmetry. The bands at ~850, 1360 and 1620 $cm^{-1}$ are due to disorder induced features arising from non-zero center phonons which contribute to the Raman spectrum because of finite crystalline size effects. These disorder induced features increase in intensity and broaden as the phonon coherence length decreases. The Raman feature at about 2900 $cm^{-1}$ is associated with a D+G combination mode, also induced by disorder.

The Raman analysis of all gFc-PA aerogels exhibits same features as pFc-PA (FIG. 21) except the peak widths and intensity. The red shift observed in D-band of all samples except pFc-PA-Ar from 1350 $cm^{-1}$ in graphitic materials to 1330 $cm^{-1}$ is attributed to more $sp^3$ bond formation. The high intensity of G band and reduction in full width half maxima (FWHM) indicates well developed 2D peak which plays an important role in characterizing all pFc-PA and gFc-PA aerogels. It indicates structural organization of $sp^2$ bonded carbon as well as conversion of amorphous carbon to graphitic carbon. The $A_D/A_G$ ratio data demonstrates a change in amorphization (Table FA-6) by following the amorphization trajectory described by A. C. Ferrari et. al and further supported by TEM and SEM.

Raman spectra of pFc-PA-$H_2$-acid shows the same pattern as observed in pFc-PA-$H_2$ aerogel indicating existence of G-band ($sp^2$) and D-band ($sp^3$) structures in equilibrium with each other. It suggests that the defects induced in both samples are due to partially developed graphitic structures. In case of gFc-PA-$H_2$-acid aerogel, the decrease in intensity as compare to gFc-PA-$H_2$, indicates the graphene like spectrum with broad symmetric 2D peak. It suggests the thin sheet like structures, also visible in SEM, with an evidence for existence of few layered graphene sheets. It is further confirmed by R-parameter from XRD (Table FA-8). Raman spectra do not resemble graphenes because mixture of carbon phases are present in the form of turbostratic graphite and entangled graphitic ribbons. The spectra of turbostratic graphite closely resemble to graphenes except the intensity of 2D peak is low as compared to the later one.

Raman spectra of gFc-PA-$H_2$ exhibit G-band at 1588 $cm^{-1}$ and D-band at 1330 $cm^{-1}$ along with symmetric 2D peak referring to Turbostratic graphite as seen in SEM, TEM and XRD. The high intensity of G band clearly indicates greater number of graphene layers stacked together, unlike gFc-PA-$H_2$-acid. The turbostratic graphite is responsible for inducing edge plane defects in gFc-PA-$H_2$ evident from high intensity of D band along with development of D' band as a shoulder of G-band. The D'-band is associated with the finite crystallite size and graphene edge defects. The other features seen at 850 $cm^{-1}$ and 2900 $cm^{-1}$ are also defect induced features.

pFc-PA-Ar aerogels show marked increase in intensity as compared to other pyrolyzed samples. The spectra resemble to that of glassy carbon like materials, where $sp^3$ (D-band intensity) character is dominating as compare to the $sp^2$ (G-band). The high intensity of D-band is attributed to the defects originated by tetrahedral structures formed, might be due to the turbostratic graphitic sheets which are prominent in their TEM and SEM hence well supported by Raman spectra as well. Raman spectra of g-Fc-PA-Ar feature a G-band at 1589 $cm^{-1}$ and D-band at 1335 $cm^{-1}$. In addition, a well-developed asymmetric 2D peak characteristic of bulk graphite was observed. The slight shift in G-band is due to the turbostratic graphitic ribbons and CNTs present in the sample.

TABLE FA-6

Raman analysis of pFc-PA and gFc-PA aerogels

| S/No | Sample | G band ($cm^{-1}$) [a] | $A_G$ | D band ($cm^{-1}$) [b] | $A_D$ | $A_D/A_G$ [c] | $L_a$ (nm) [d] |
|---|---|---|---|---|---|---|---|
| 1 | pFc-PA-$H_2$ | 1589 (69) | 27553 | 1332 (163) | 62762 | 2.27 | 16.90 |
| 2 | pFc-PA-$H_2$-acid | 1593 (68) | 20373 | 1330 (157) | 44636 | 2.19 | 17.50 |
| 3 | pFc-PA-Ar | 1588 (80) | 263189 | 1353 (166) | 713010 | 2.71 | 14.17 |
| 4 | gFc-PA-$H_2$ | 1588 (42) | 16296 | 1330 (52) | 27181 | 1.85 | 20.75 |
| 5 | gFc-PA-$H_2$-acid | 1594 (57) | 6627 | 1330 (48) | 7559 | 1.14 | 27.23 |
| 6 | gFc-PA-Ar | 1589 (52) | 7395 | 1335 (81) | 12600 | 1.70 | 22.58 |

G and D bands represents respective peak heights,
[a] numbers in parenthesis is FWHM of G-band,
[b] numbers in parenthesis is FWHM of D-band, $A_G$ and $A_D$ represents area after lorentzian peak fitting of Raman spectrum,
[c] $A_D/A_G$ is the ratio of area of G and D bands.
[d] $L_a$ is stack height of graphitic structures calculated by empirical Knights formula.

The $L_a$ (nm) is stack height of the graphitic material in other words it shows the number of layers stacked in graphite, can be calculated by XRD and Raman with Scherer's equation and Knight's formula respectively. As all pFc-PA samples show broad features instead of sharp peaks Scherer's equation cannot be applied. Instead Knight's formula to calculate $L_a$ (nm) was used as shown in Table FA-6. Further analysis of Raman spectra by Lorentzian peak fit determines the ratio of each graphitic phase present in the sample. The analysis shows a mixture of carbon phases in all pFc-PA aerogels while all gFc-PA aerogels transforms into single dominating phase. These results are in well in agreement with XRD Lorentzian peak fit of 002 Bragg peak.

Example 37

XRD

XRD pattern of all pFc-PA aerogels show band with 2θ at 26.24° for hexagonal planes of graphite (002) while 41°, 46.6° are typical corresponding to cementite ($Fe_3C$). The reflections 44.7°, 64.8° and 89.2° fit well with diffraction planes of 110, 220 and 200 of alpha iron (α-Fe). The asymmetric peak at 2θ~26.24° in pFc-PA aerogels, suggests superimposed reflections of more than one phases of carbon present in the samples. The XRD pattern suggests graphite, turbostratic graphite and amorphous carbon coexists in these samples.

XRD pattern of all gFc-PA aerogels features 2θ at 26°, 43°, 54° and 73° which are referred to as 002, 100/101, 004 and 110 diffractions planes respectively (FIG. 22, right). XRD pattern of all gFc-PA aerogels show 002 lattice fringe at 2θ~26.2° characteristic of hexagonal graphite. The structure of the material can be understood well by taking into account the 002 peak indicative of the stack height of the aromatic plane of carbon crystallite. The 100/101 reflection at 2θ~43°-44° and 110 lattice fringe at 78° indicate the hexagonal ring symmetry of the material. The 004 peak at 2θ~53°-54° is responsible for the 2D and 3D graphitic structures of gFc-PA aerogels absent in pFc-PA aerogels. The 002 and 004 reflections are attributed to the length of the c-axis perpendicular to the basal planes. The shape of the 002 and 004 peaks refers to the thickness of graphite sheets present in the sample as seen in gFc-PA-Ar. The broader and less intense 002 and 004 peaks indicate thin graphite sheets, in other words, only few layers are present as in pFc-PA-$H_2$-acid see TEM and SEM (FIGS. 19 and 20, respectively). The high intensity of 002 peak with broad peak base in gFc-PA-$H_2$ indicates greater number of graphene sheets which are stacked together in specific arrangement referring to graphite but a fraction of thin sheets are also present. The high intensity of 100 and 110 peaks around 42° and 79° indicate presence of small graphene sheets, as seen in case of gFc-PA-Ar.

The increased degree of graphitization can be indicated by sharpness and narrowness of full width half maxima (FWHM) values (Table FA-7) of 002 peak. The $L_c$ increases with increase in temperature as seen from pFc-PA to gFc-PA tabulated in Table FA-7. The 002 diffractions of all samples show a tail to low angle side, while peak of 100 diffraction plane have its tail towards high angle side, indicative of highly crystalline graphite with turbostratic graphitic material. The $d_{002}$ spacing of all gFc-PA show no specific change even after high temperature treatment indicates the hexagonal structures were developed at low temperatures. The little change observed is due to the mixture of different carbon phases present in samples, it varies with their amount present in the sample (values of different carbon phases present are tabulated in Table FA-7 after Lorentzian fit).

TABLE FA-7

XRD analysis data from Lorentzian peak fitting of 002 peak

| Sample | $d_{002}$ (nm) | Lc (nm) | R-parameter | Amorphous Carbon (24°) [a] | Turbostratic Graphite (25.5°) [b] | Graphite (26.2°) [c] | H-graphite (26.2°) [c] | R-graphite (26.6°) [d] |
|---|---|---|---|---|---|---|---|---|
| pFc-PA-$H_2$ | 0.336 | 4.3 | 2.22 | 29.3 | — | 70 | | — |
| pFc-PA-$H_2$-acid | 0.348 | 4.7 | 1.51 | 40 | 54 | 6 | | — |
| pFc-PA-Ar | 0.336 | 4.9 | 2.49 | — | 60 | 40 | | — |
| gFc-PA-$H_2$ | 0.338 | 6.2 | 11.24 | — | 34 | 45 | | 21 |
| gFc-PA-$H_2$-acid | 0.339 | 7.1 | 5.97 | — | 40 | 60 | | — |
| gFc-PA-Ar | 0.335 | 8.2 | 36.61 | — | 38 | 36 | | 26 |

$d_{002}$ = 1.54/2sinθ where θ = θ/2 and Lc is calculated by Scherer's equation by XRD instrument, R = B/A,
[a] Amorphous carbon
[b] Turbostratic graphite,
[c] Hexagonal graphite,
[d] Rhombohedral graphite, are the percentage of carbon phases present in the sample calculated by lorentzian peak fitting of 002 peak in XRD pattern.

Lorentzian fit of 002 reflection for graphite (26.2°) turbostratic graphite (25.5°) and amorphous carbon (24°) enables us to calculate the percentage of different phases of graphite (hexagonal & rhombohedral) and turbostratic graphite (Table FA-7).

To measure the number of graphitic sheets arranged as single layer in sample, an empirical parameter, R was used.

$$R=B/A \quad \text{(Equation FA-4)}$$

gFc-PA-Ar has a large number of single layers as compare to others indicating the carbon is behaving as soft carbon. Furthermore these single layers curl up into multi walled carbon nanotubes as confirmed by SEM and TEM. The shape of XRD pattern indicates percentage of single, double and triple layered fractions of graphenes.

Example 38

BET

Nitrogen sorption isotherm of all pFc-PA and gFc-PA aerogels (FIG. 23) show type IV adsorption isotherm, reach saturation and have well pronounced adsorption and desorption hysteresis loop of H1 and H2 type. The broad spreading of hysteresis loop in the range of $P/P_o$~0.45-0.99 suggests different type of pores, micro & mesopores in all pFc-PA while strictly mesoporous material in all gFc-PA aerogels. It is well in agreement with the graphitic nano structures developed at these temperatures as demonstrated by TEM and SEM. The type IV isotherm is associated with capillary condensation taking place in mesoporous materials limiting the uptake of $N_2$ at high pressures but substantial volume of $N_2$ adsorbed at relative low $P/P_o$ is owed to micropores, the % of micropores in the samples are calculated on the basis of t-plot micropore volume and total volume ($V_T$) from $N_2$-sorption analysis.

and Ar) aerogels graphitic structures and amorphous carbon are observed, while gFc-PA ($H_2$ and Ar) aerogels graphitic structures along with turbostratic graphite are present and no amorphous carbon. In turbostratic graphite graphene sheets are randomly arranged so there edges are exposed. They have greater reactivity towards functional groups as compare to graphite and hydroxyl groups can be easily attached

TABLE FA-8

Surface area and pore size analysis for pFc-PA and gFc-PA aerogels.

| Sample | BET surface area $\sigma$ ($m^2$ $g^{-1}$) | porosity, $\Pi$ (% void space) | External BET surface area $\sigma_{ext}$ ($m^2$ $g^{-1}$) | Internal BET surface area $\sigma_{int}$ ($m^2$ $g^{-1}$) | t-plot micropore area | Micropore (%) | Mesopore (%) |
|---|---|---|---|---|---|---|---|
| pFc-PA-$H_2$ | 369 | 88 | 194 | 175 | 175 | 11.0 | 88 |
| pFc-PA-$H_2$-acid | 282 | 69 | 168 | 114 | 113 | 8.0 | 92 |
| pFc-PA-Ar | 349 | 31 | 113 | 236 | 235 | 30 | 69 |
| gFc-PA-$H_2$ | 100 | 41 | 100 | 0 | 0.4 | 0.0 | 100 |
| gFc-PA-$H_2$-acid | 261 | 43 | 255 | 6 | 5.7 | 0.14 | 99 |
| gFc-PA-Ar | 49 | 33 | 48 | 1 | 1.2 | 1.13 | 99 |

All the pFc-PA aerogels show 68% shrinkage as comparable to parent gels while gFc-PA aerogels showed no shrinkage with respect to pFc-PA aerogels suggesting strong skeletal frame work in all samples. Only pFc-PA-$H_2$ sample show well developed graphitic structures with skeletal density comparable to graphite. In pFc-PA-$H_2$-acid the skeletal density is reduced because of removal of amorphous carbon during acid treatment. The higher surface area of pFc-PA-$H_2$ and pFc-PA-Ar is attributed to layered structure of graphitic materials formed, while these are absent in pFc-PA-$H_2$-acid. The porosity is highest in pFc-PA-$H_2$ due the well coral like internal morphology with micropores as well as mesopores.

to them even if a little moisture is present. The absorption band in the range of 1500-1600 $cm^{-1}$ are characteristic band for graphite. This band is also visible in Raman spectra as G-band with Raman active $E_{2g}$ (doubly degenerate in plane optical vibration) vibrations at 1500-1600 $cm^{-1}$. The $E_{1u}$ along with $A_{1u}$ are the translations of the plane which are IR active vibrations at 1582 $cm^{-1}$ and 868 $cm^{-1}$ respectively. The absorption features at 2800 $cm^{-1}$ and 3000 $cm^{-1}$ on IR-spectra are due to the CH and $CH_2$ bonding while the doublet in the region of 2500 $cm^{-1}$-2000 $cm^{-1}$ is attributed to existence of C=C bonds representative of the $sp^2$ character of the graphitic material.

TABLE FA-9

Materials characterization data for pFc-PA and gFc-PA aerogels

| Sample | linear shrinkge (%)[a,b] | bulk density, $\rho_b$ (g $cm^{-3}$)[a] | skeletal density, $\rho_s$ (g $cm^{-3}$)[c] | porosity, $\Pi$ (% v/v) | Specific pore volume ($cm^{-3}$ $g^{-1}$)[d] $V_{Total}$ | $V_{1.7-300\,nm}$ | $V_{>300\,nm}$ | BET surf. area, $\sigma$ ($m^2$ $g^{-1}$) | av. pore diameter, (nm) $4 \times V_{Total}/\sigma$[e] | BJH[f] | particle diameter (nm)[g] |
|---|---|---|---|---|---|---|---|---|---|---|---|
| pFc-PA-$H_2$ | 68 ± 0.050 | 0.286 ± 0.017 | 2.40 ± 0.004 | 88 | 3.086 | 0.705 | 2.381 | 369 | 9.0 (33) | 18[9.48] | 07 |
| pFc-PA-$H_2$-acid | 68 ± 0.006 | 0.701 ± 0.008 | 1.70 ± 0.006 | 59 | 0.838 | 0.769 | 0.069 | 282 | 9.0(12) | 32[8.80] | 12 |
| pFc-PA-Ar | 65 ± 0.030 | 1.045 ± 0.015 | 1.53 ± 0.005 | 32 | 0.303 | — | — | 349 | 5.0(23) | 39[2.60] | 11 |
| gFc-PA-$H_2$ | 0.0 ± 0.000 | 0.893 ± 0.030 | 1.52 ± 0.003 | 41 | 0.462 | 0.406 | 0.056 | 100 | 16(18) | 16[7.85] | 16 |
| gFc-PA-$H_2$-acid | 0.0 ± 0.000 | 0.871 ± 0.014 | 1.51 ± 0.005 | 42 | 0.486 | 0.984 | −0.498 | 261 | 15(04) | 12[6.68] | 15 |
| gFc-PA-Ar | 0.0 ± 0.000 | 0.985 ± 0.032 | 1.43 ± 0.005 | 33 | 0.316 | — | — | 049 | 16(19) | 12[0.73] | 08 |

[a]Average of 4 samples.
[b]Shrinkage = 100 × (mold diameter − sample diameter)/(mold diameter).
[c]Single sample, average of 50 measurements.
[d]$V_{Total}$ was calculated via $V_{Total} = (1/\rho_b) − (1/\rho_s)$, $V_{1.7-300\,nm}$ from $N_2$-desorption volume. $V_{>300\,nm} = V_{Total} − V_{1.7-300\,nm}$.
[e]Average pore diameter is calculated by $4 \times V_{Total}/\sigma$ method, For first number, $V_{Total}$ was calculated by the single-point adsorption method; for the number in brackets, $V_{Total}$ was calculated via $V_{Total} = (1/\rho_b) − (1/\rho_s)$.
[f]From the BJH plots: first numbers are the peak maxima; numbers in brackets are widths at half maxima.
[g]Particle diameter = $6/(\rho_s \times \sigma)$.

Example 39

FTIR

Figure 24:
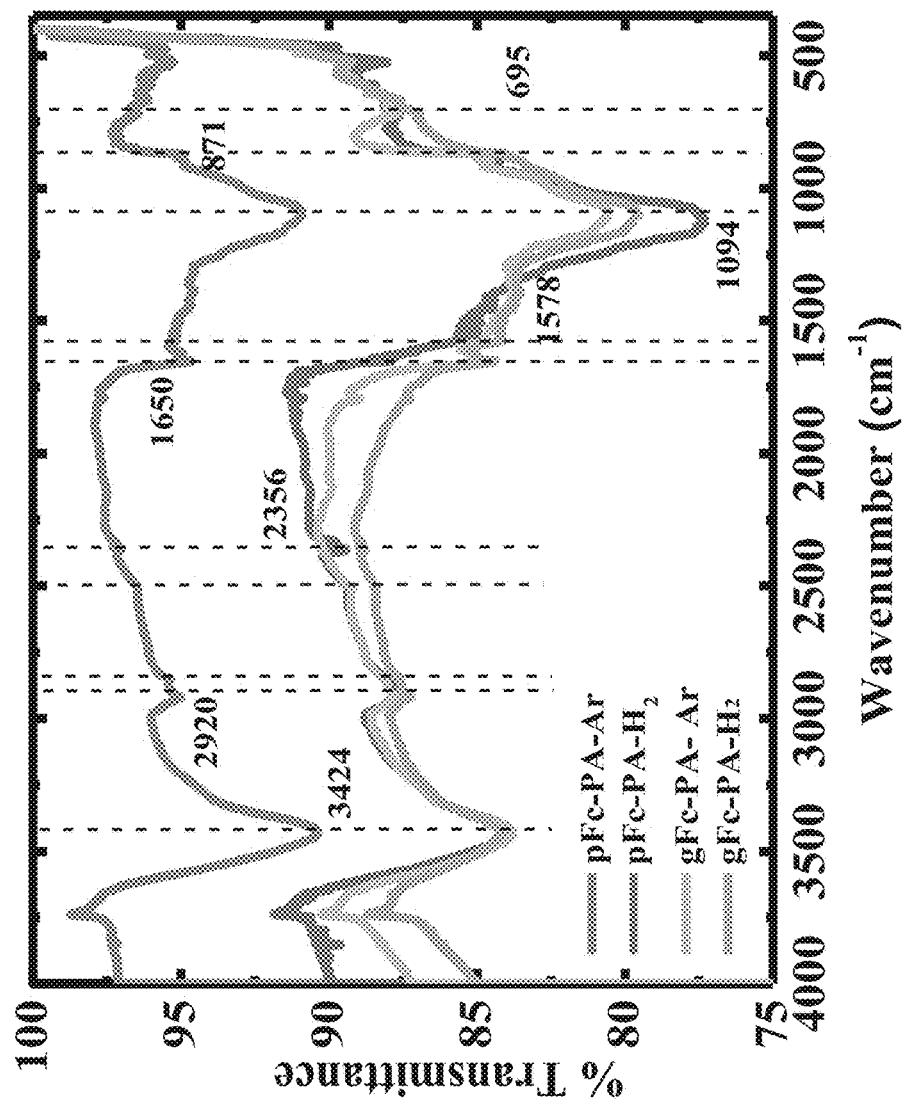
FIG. 24 displays FTIR spectra of pFc-PA and gFc-PA aerogels.

FTIR spectra of pFc-PA and gFc-PA aerogels ($H_2$ and Ar) (FTIR spectra, FIG. 24) exhibit characteristic features of graphitic materials. FTIR spectra of gFc-PA aerogels show an up shifted band in the region of stretching vibration of hydroxyl group (3600-3000 $cm^{-1}$) has an intense broad band referring to existence of hydroxyl groups on the surface of sample also common in graphitic materials. In pFc-PA ($H_2$ Example 40

Ferrocene is an organometallic compound highly volatile with decomposition temperature higher than 400° C. The ferrocene dicarboxylic acid used herein starts decomposing at 250° C. Ferrocene is a known iron precursor for the production of catalytic iron nano particles. On the basis of detailed analysis of Fc-PA aerogels, pyrolyzed within the temperature range of 500-1400° C. (pFc-PA-$H_2$ aerogels) and ultimately at 2300° C. in different environments (gFc-PA aerogels), by SEM, TEM, Raman, $N_2$-Sorption, FTIR and XRD, without being bound by theory, it can be assumed that the porous structure of monoliths and their degree of graphitization along with the graphitic nano structures developed are significantly affected by gaseous atmosphere and temperature during pyrolysis.

All pFc-PA aerogels undergo several structural changes during pyrolysis followed by graphitization (gFc-PA). It can be summarized in stages based on their analysis as follows: a) Carbonization of Fc-PA aerogels into amorphous carbon and its transformation into carbon network with iron precursors still attached; b) The reduction of covalently bonded iron within the ferrocene entity to metallic iron nano particles; c) The metallic iron nanoparticles act as catalyst and are responsible for inducing solid state transformations of amorphous carbon and carbon network to graphitic structures by dissolution precipitation method.

The concept was homogenous dispersion of the catalytic iron nanoparticles through iron precursor which is covalently bonded as ferrocene dicarboxylic in the Fc-PA polymer repeat units. The dispersion of iron nanoparticles is homogenous at low temperatures. As temperature increases the melting of iron nanoparticles starts instead of its bulk melting temperature of 1538° C. Sintering of iron nanoparticles results in increased size of catalytic nanoparticles, which is believed to be crucial for graphitization of Fc-PA aerogel's carbon matrix. The large catalytic particles are believed to be responsible for larger graphitic nano structures such as nano capsules of larger diameter due to the large iron core particles with thick graphitic walls effecting the mesoporosity of the pFc-PA-$H_2$ aerogels. The nanocapsules during pyrolysis are believed to be carbon encapsulated iron nano particles (CENP's).

The pyrolysis and graphitization of Fc-PA aerogels engender bi-phase materials, which are composed of mixture of graphitic and amorphous carbon and graphite and turbostratic graphite respectively. pFc-PA aerogels behave as amorphous carbon at 500-700° C. with metallic iron and it undergoes state changes along with the amorphous carbon and a new phase formed is iron carbide. As the temperature increases up to 800° C., graphitic carbon framework is formed and the aerogel becomes electrically conductive as well as magnetically active, hence low temperature graphitization is achieved as confirmed by XRD, Raman, FTIR, SEM and TEM.

By changing the pyrolysis temperature and atmosphere ($H_2$ and Ar) different graphitic nano structures were found. At 800° C. under $H_2$ carbon nano capsules were found, it is investigated that the nano melting of iron and sintering of nanoparticles may be responsible for them, when the same sample is treated at 2300° C. under inert atmosphere the sintered iron nano particles of larger diameter produces larger graphitic structures. The increase in degree of graphitization may indicate consecutive arrangement of 2D sheets into well graphitized nano structures. In $H_2$ atmosphere, hydrogen acts as a reducing agent; there is no liberation of gaseous materials leading to sheet like structures along with entangled turbostratic graphite. In case of pFc-PA-Ar and gFc-PA-Ar the atmosphere is inert and the liberation of gases are easy as traces of oxygen might be available. They produce hallow CNTs with the liberation of $CO_2$ as seen in the SEM and supported by the Raman spectra also.

The well-defined lattice fringes at 002 suggest high crystallinity of graphitic nanostructures, d-spacing ($d_{002}$) is close to 0.334 nm in all gFc-PA aerogels which is comparable to $d_{002}$ of graphite. The selected area electron diffraction pattern (SAED) shows that graphitic material is polycrystalline which is very different from the graphitic SAED pattern which shows regular hexagonal diffraction pattern. It may indicate that the nano sheets contain several sub-platelets, sheets are multi crystalline in nature, but in gFc-PA aerogels the graphitic carbonaceous structures become kinked intertwined graphitic ribbons with some graphene sheets. In gFc-PA aerogels the carbon structures visible are disordered graphene sheets and carbon nanotubes which are not present at 800-1400° C.

Example 41

Transmetalation

Aerogels are nanoscopic pore solid architectures with high surface area and continuous mesoporous network, believed to be ideal as catalyst supports. Without being bound by theory, it is believed that the three dimensional (3-D) continuous mesoporous network facilitates rapid diffusion of reactants to active sites in the aerogels, such that mass transport occurs on the order of open medium diffusion rates. As mass transport must be factored into the kinetics of any catalyst, the continuous mesoporous structure of aerogels will be critical to their performance as composite nanostructured catalysts.

Carbon aerogels are unique porous materials that exhibit numerous exceptional properties, including mechanical stability, continuous porosity, high surface area, and high electrical conductivity and, as such, are believed to be attractive platforms for incorporation of catalytic particles. The metals are induced in carbon aerogels with the goal of modifying structure and catalytic activity, due to homogenous distribution of metal nano particles in the 3-D network of carbon. Thus carbon supported metal aerogels may be potentially invaluable as they have the unique properties of metals as well as those of carbon aerogels. Conventionally, it has been reported that the loading of catalyst particles into carbon nanostructures can be performed by a variety of methods, including the impregnation, doping of metal salts and reduction of metal salts into a support structure or the electrochemical deposition of catalyst particles on the carbon material.

One of the challenges associated with the design of these catalytic materials is believed to have been the development of methods that can reduce the overall loading of the costly noble metal catalyst while retaining the high catalytic activity of the material. Nowadays, precipitation of gold from gold chloride solutions by activated carbon is of interest in catalysis, electronics and biotechnology. At the same time, recovery and concentration of gold by chloride leaching remains topical in technology of hydrometallurgical extraction as more environmentally friendly compared with conventionally used cyanide method. The aggregation of gold particles are known for decreasing the catalytic activity of gold catalyst significantly. To circumvent this drawback, Lucchesi et al. (Adv. Synth. Catal., 350:1996 (2008)), has incorporated carbon black whose partially graphitic structures enhanced the stability of gold nano clusters.

Traditionally, nitro group reductions are carried out using precious metal complexes as catalyst which are expensive as well as air and moisture sensitive. Thus, identifying new economical and practical alternative materials is desirable. Herein, an inexpensive heterogeneous carbon supported iron metal catalyst was used.

The Mizoroki-Heck reaction catalyzed by palladium on solid support has recently attracted a great deal of attention. This is an important synthetic C—C bond forming reaction, often used to functionalize aromatic rings. More recently some silica gels have been prepared as catalyst supports for the Heck reaction. However, in general it has been reported that carbon supports seem to give better results than silica.

The Oxidation of alcohols into aldehydes, ketones and carboxylic acids is believed to be one of the most crucial reactions in the fine chemical and pharmaceutical industries. Many oxidations of this type are traditionally carried out using stoichiometric oxygen donors such as chromate or permanganate, but these reagents are expensive and have serious toxicity issues associated with them. However, the stoichiometric oxidation process suffers from low atom efficiency and a large amount of waste production, leading to a severe environmental impact. Heterogeneously catalyzed liquid-phase oxidations using molecular oxygen ($O_2$) as the sole oxidant are attractive alternatives. Among the various catalysts exploited so far, platinum (Pt) supported on activated carbon (Pt/AC) has been studied extensively as a suitable candidate for alcohol oxidation because it works in water under atmospheric pressure of $O_2$. However, the major drawback of the use of Pt/AC is rapid deactivation due to by-product poisoning and over-oxidation of the Pt catalyst.

Endless formulations of composite materials are possible from the inclusion of metals for use as catalysts. However, the use of these remarkable materials has been hindered due to difficulties in their manufacture. Herein, heterogeneous catalysis by using carbon aerogels with metals (Fe, Au, Pt and Pd) is described. The metal doped carbon aerogels are synthesized by the isocyanate route. The metallic nanoparticles were formed by reduction of covalently bonded iron in ferrocene polyamide (Fc-PA) aerogels during pyrolysis under reducing atmosphere ($H_2$). The metallic nano particles were protected from agglomeration by using a different way than conventional route of synthesizing carbon supported metal aerogels. The process is termed as transmetalation, where the carbon supported iron aerogel undergoes a treatment with corresponding metal chloride solution. As a result, homogeneously dispersed iron particles are replaced by respective metal particles (Au, Pd, Pt).

Preparation and Characterization of Catalysts.

Figure 25:
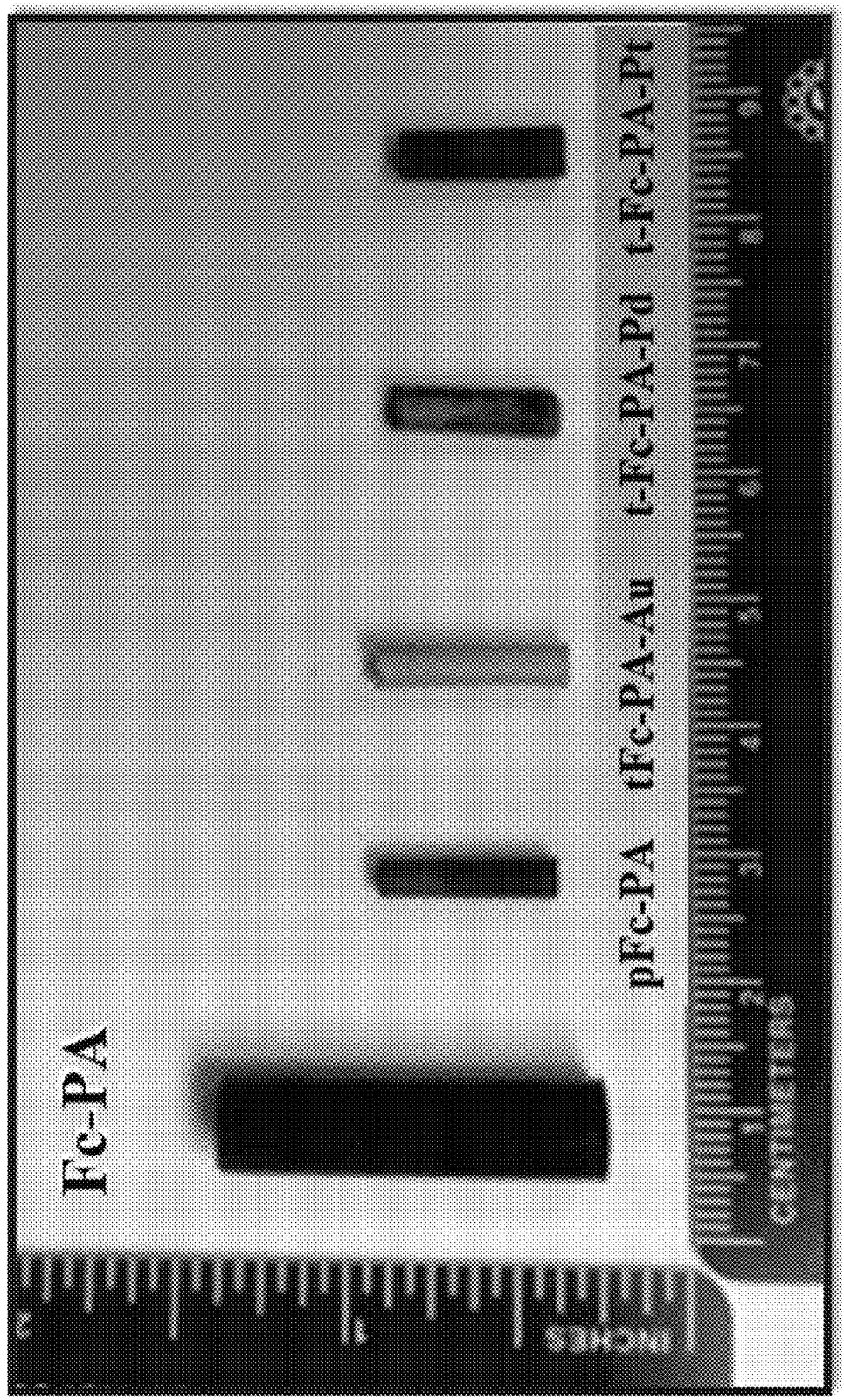
FIG. 25 displays Fc-PA (15%) aerogel, pFc-PA aerogel, tFc-PA-Au, tFc-PA-Pt, tFc-PA-Pd.

For the preparation of catalysts Fc-PA (15%) formulation was selected on the basis of their sturdiness without sacrificing their BET surface area and porosity. Monoliths were transferred to MTI GSL1600X-80 tube furnace (tube made up of alumina 99.8% pure, 72 and 80 mm inner and outer diameters of the tube, 457 mm heating zone). The monoliths were heated at 800° C. under flowing $H_2$ (150 mL min$^{-1}$) for 5 h. The temperature of the furnace was slowly raised to the desired temperature (800° C.) at 5° C. min$^{-1}$. At the end, the furnace temperature was programmed to room temperature at 5° C. min$^{-1}$ in $H_2$ atmosphere. Carbon supported iron aerogel monoliths pyrolyzed at 800° C. under $H_2$ (pFc-PA) were transmetalated with noble metals (Au, Pt, Pd) giving tFc-PA-Au/Pt/Pd aerogels. Samples were dipped in their corresponding chloride solutions for 24 h right after taking them out from the furnace. Washed couple of times with acetone and vacuum dried overnight (FIG. 25). The tFc-PA aerogels showed anchoring of noble metals, hence they were scraped before characterization to ensure the results are only due to the transmetalation instead of anchoring.

Figure 26:
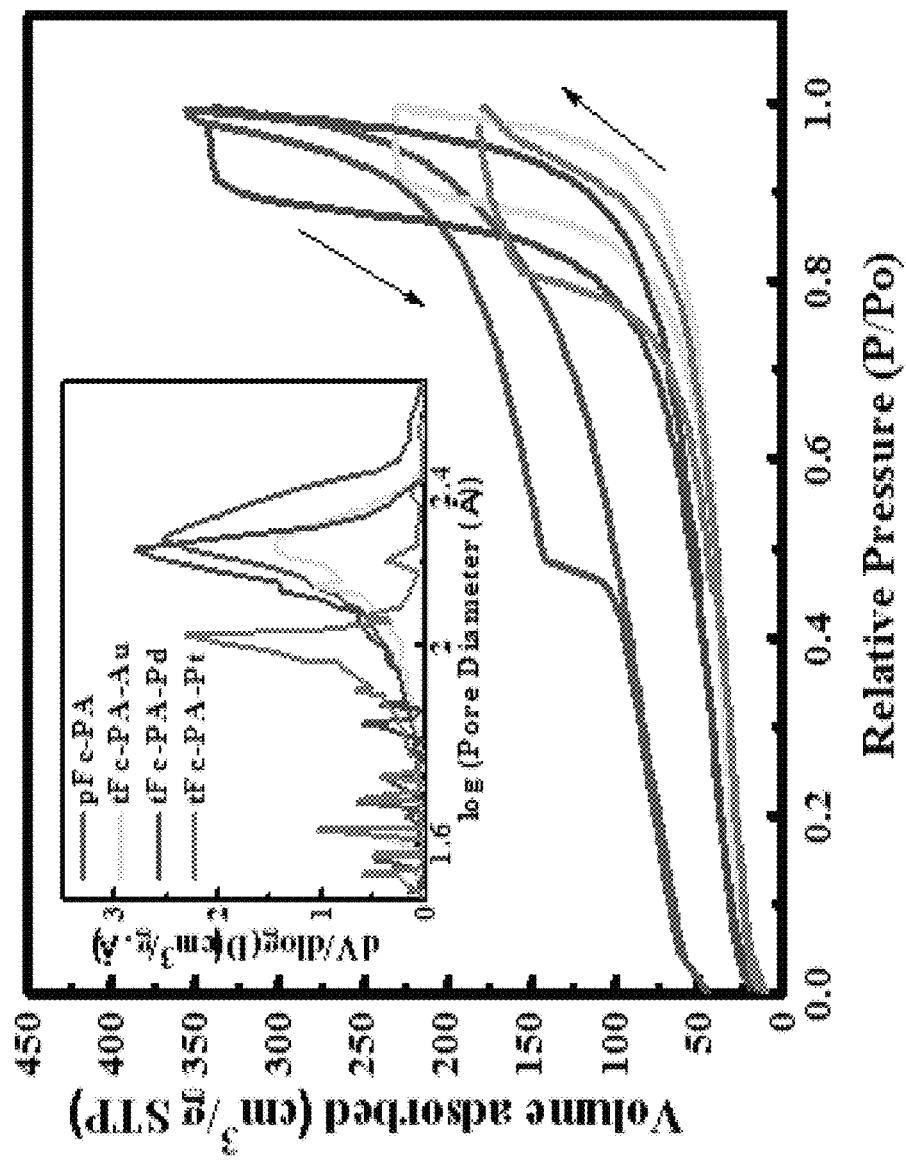
FIG. 26 displays $N_2$ sorption isotherms of pFc-PA and tFc-PA (Au, Pt, Pd) aerogels; inset shows pore size distribution.

It is not atypical that added metals or metal ions change the final morphology of the pyrolyzed aerogels often through inhibition of the higher surface area, amorphous phase, and crystallization. The BET isotherms of pFc-PA show type IV adsorption isotherm with hysteresis loop H3 indicating capillary condensation within the mesopores (FIG. 26). It has broad hysteresis loop with $P/P_o$~0.45-0.99 suggests developed mesoporosity characterized by slit like pores as seen by SEM. The transmetalated aerogels reach saturation with irregular large sized pores. In transmetalated aerogels (tFc-PA aerogels) lower BET surface area is observed without more shrinkage but at the expense of micropore area which almost reduces to 2 m$^2$ g$^{-1}$ in case of Pd as compared to 175 in pFc-PA.

TABLE FA-10

Materials characterization data for pFc-PA and tFc-PA aerogels.

| sample | linear shrinkge (%)[a,b] | bulk density, $\rho_b$ (g cm$^{-3}$)[a] | skeletal density, $\rho_s$ (g cm$^{-3}$)[c] | porosity, Π (% v/v) | Specific pore volume (cm$^{-3}$ g$^{-1}$)[d] $V_{Total}$ | $V_{1.7-300\ nm}$ | $V_{>300\ nm}$ | BET surf. area, σ (m$^2$ g$^{-1}$) | average pore diameter, (nm) $4 \times V_{Total}/\sigma_e$ | BJH[f] | particle diameter (nm)[g] |
|---|---|---|---|---|---|---|---|---|---|---|---|
| pFc-PA | 68 ± 0.50 | 0.286 ± 0.004 | 2.40 ± 0.004 | 88 | 3.086 | 0.705 | 2.381 | 369 | 9(33) | 18[9.48] | 7 |
| tFc-PA-Au | 69 ± 0.002 | 0.190 ± 0.003 | 1.96 ± 0.038 | 90 | 4.753 | 0.354 | 4.399 | 101 | 18(14) | 17[7.86] | 30 |
| tFc-PA-Pt | 70 ± 0.002 | 0.191 ± 0.004 | 1.87 ± 0.016 | 89 | 4.701 | 0.284 | 4.417 | 100 | 18(17) | 10[1.69] | 32 |
| tFc-PA-Pd | 70 ± 0.005 | 0.216 ± 0.008 | 1.98 ± 0.018 | 86 | 4.124 | 0.533 | 3.591 | 133 | 12(16) | 17[5.07] | 23 |

[a]Average of 4 samples.
[b]Shrinkage = 100 × (mold diameter − sample diameter)/(mold diameter).
[c]Single sample, average of 50 measurements.
[d]$V_{Total}$ was calculated via $V_{Total} = (1/\rho_b) - (1/\rho_s)$, $V_{1.7-300\ nm}$ from N$_2$-desorption volume. $V_{>300\ nm} = V_{Total} - V_{1.7-300\ nm}$.
[e]Average pore diameter is calculated by $4 \times V_{Total}/\sigma$ method, For first number, $V_{Total}$ was calculated by the single-point adsorption method; for the number in brackets, $V_{Total}$ was calculated via $V_{Total} = (1/\rho_b) - (1/\rho_s)$.
[f]From the BJH plots: first numbers are the peak maxima; numbers in brackets are widths at half maxima.
[g]Particle diameter = $6/(\rho_s \times \sigma)$.

The skeletal density of pFc-PA is (2.40 g cm$^{-3}$) which decreases to (1.87-1.98 g cm$^{-3}$) after transmetalation. It might be due to the removal of amorphous carbon present in the sample leaving behind the density of turbostratic graphite 1.9 g cm$^{-3}$. The skeletal structure of the material consists of interconnected nanometer-sized carbon ligaments that define a continuous mesoporous network. The average pore diameter of these samples remains almost the same while the particle diameter of the transmetalated aerogels increases 4-fold in comparison to un-transmetalated. This is evident from the SEM of these samples. Without being bound by theory, it is believed that the reason is replacement of iron metal with the larger particles of the corresponding metal.

Figure 27:
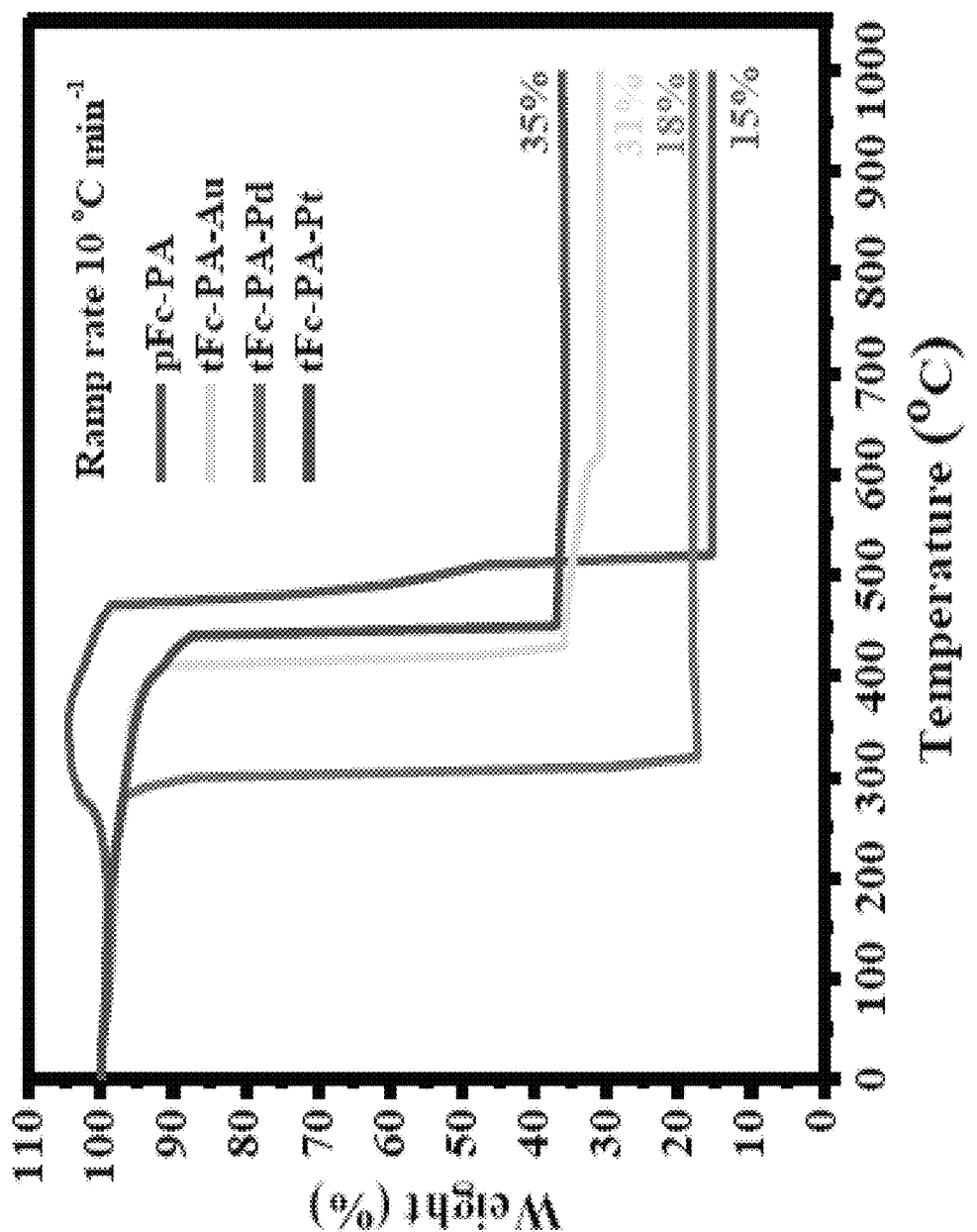
FIG. 27 displays thermogravimetric analysis of pFc-PA and tFc-PA (Au, Pt, Pd) aerogels under oxygen.

To quantify the metal content in pFc-PA and tFc-PA aerogels, thermogravimetric analysis under oxygen was employed (FIG. 27). The pFc-PA aerogels are stable up to 500° C., with an initial weight gain attributed to oxidation of iron and final loss in weight, leaving behind char yield of 15%. The quantity of metal determined by char yield corresponds to the original metal loading in the form of iron precursor in parent aerogel.

Platinum and gold transmetalated aerogels are also stable above 400° C. with a residue of 35% and 31% respectively, which is in well agreement with transmetalated iron in the corresponding aerogel, while in case of palladium, the aerogel is stable above 300° C., leaving solid content around 18%.

Figure 28:
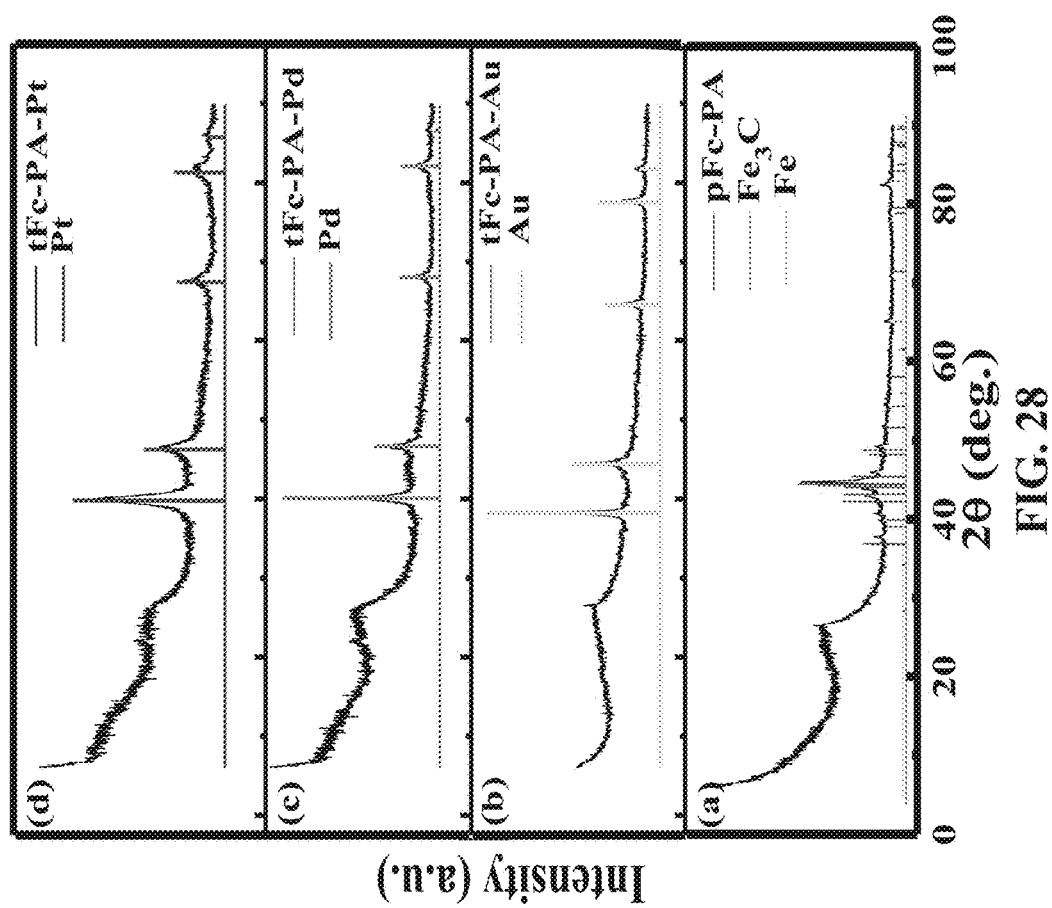
FIG. 28 displays the following: a) XRD diffraction pattern for pFc-PA aerogels; b) tFc-PA-Au aerogels; c) tFc-PA-Pd aerogels; d) tFc-PA-Pt aerogels.

The X-Ray diffraction pattern of pFc-PA and tFc-PA aerogels is markedly different as seen in (FIG. 28). The pFc-PA diffraction pattern exhibit low temperature graphitization by showing a peak at 2θ~26.2°. The crystalline phase of iron and iron carbide with their characteristic lattice fringes at 44°, 65° and 83° referring to 110, 200 and 211 diffraction planes of alpha iron, while the diffractions at 43.7°, 44.5°, 44.9° and 45.8° are attributed to 102, 220, 031 and 112 diffraction planes of iron carbide. After transmetalation, the corresponding XRD pattern have characteristic lattice fringes of face centered cubic (fcc) metallic particles of Au, Pt and Pd metals. Moreover, no diffractions related to iron are observed after transmetalation, supports transmetalation of iron. The iron carbide is also not visible. It might be possible that metal chloride solution reacts with iron carbide to give iron chloride as a byproduct while simultaneously the noble metal particles are reduced and precipitated. The noble metal particles after attaining zero valent state are deposited in place of iron hence in this way noble metals are exchanged with iron particles.

Figure 29:
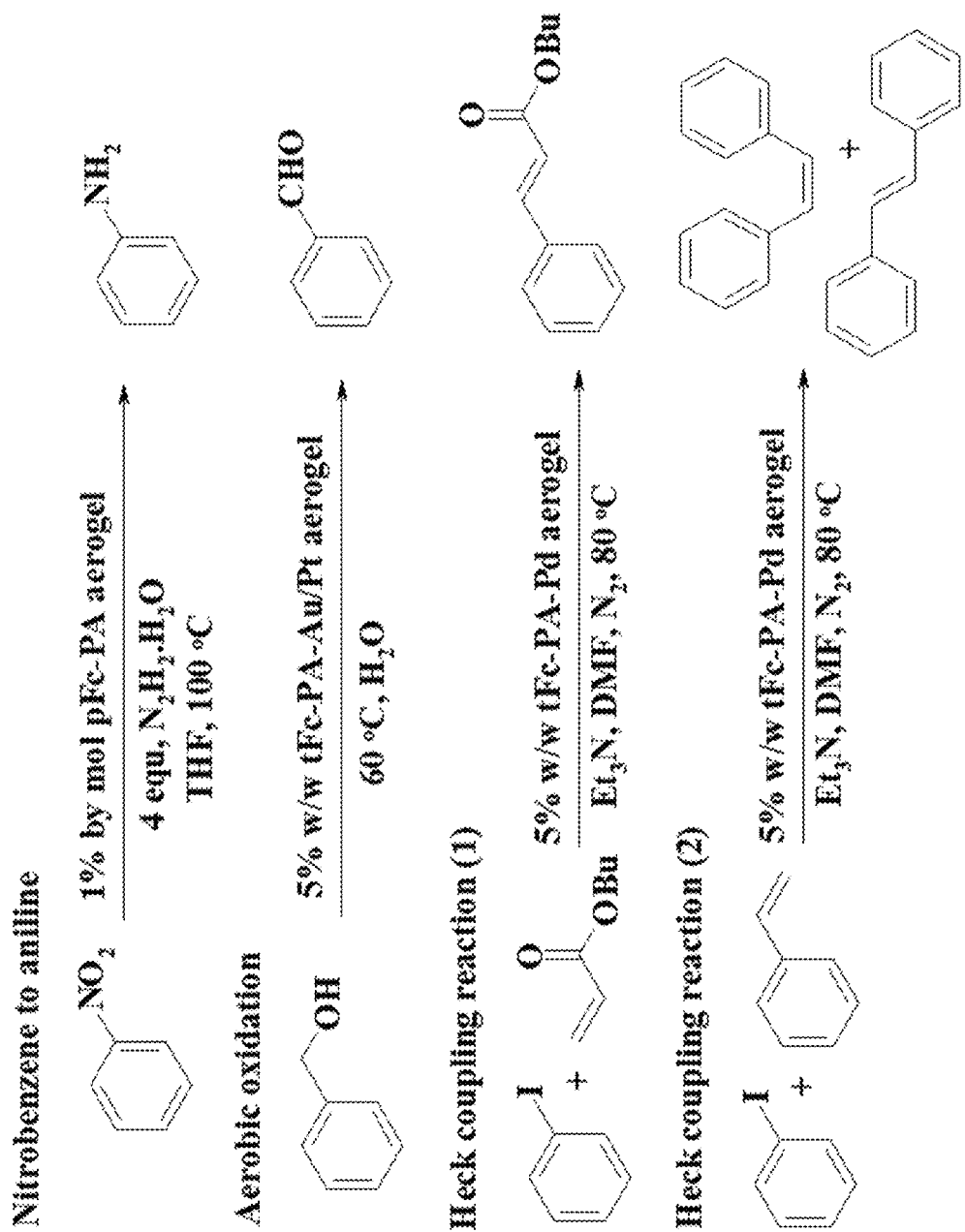
FIG. 29 displays catalytic reactions of pFc-PA and tFc-PA (Au, Pt, Pd) aerogels.

Catalysis.

pFc-PA aerogels were used as catalysts for conversion of nitrobenzene to aniline (FIG. 29) in the presence of hydrazine hydrate as a reducing agent, which is extensively used in organic synthesis because it only leaves nitrogen and water as by-products. The tFc-PA-Au and tFc-PA-Pt aerogels were employed for aerobic oxidation of alcohols in water. Oxidation of benzyl alcohol was carried out using tFc-PA-Au or tFc-PA-Pt catalytic monoliths under 1 atm of $O_2$ in water, as shown in FIG. 29. Both catalysts proved to be efficient for the oxidation of benzyl alcohol to give benzaldehyde.

The tFc-PA-Pd aerogels were selected for classical Heck coupling reaction. The Heck reaction is an important synthetic tool to facilitate C—C bond formation by a Pd mediated catalytic cycle, and is also used to functionalize aromatic rings. To accomplish this goal, butyl acrylate was treated with iodobenzene in DMF in the presence of tFc-PA-Pd monolithic catalyst (FIG. 29) to give butyl cinnamate as the only product. GC-MS showed 100% conversion of reactants to products in each catalytic reaction. The results are summarized in Table FA-11. Recycling and reusability of all the catalysts was tested on the model systems. All the catalytic aerogels were recycled and reused three times without any significant loss of catalytic activity.

Additional Embodiments and Examples

In the following are described additional embodiments and examples pertaining to the monolithic nanoporous carbon-supported Fe, Au, Pt, Pd, Co, Ni, Ru, and Rh catalysts disclosed herein, which are derived by pyrolysis and transmetalation via galvanic replacement of ferrocene-based polyamide aerogels. As previously described in the foregoing, the ideal heterogeneous catalyst is believed to consist of high surface-to-volume catalytic particles dispersed in an inert support. Particulate supports (e.g., activated carbon) are especially useful, because they provide high surface area for catalytic particles to latch on, while they ensure low mass transfer resistance to and from those active catalytic sites. In another embodiment in this context, additional benefits may be realized from the porous monolithic catalytic systems described herein that could be harvested out and re-used without costly filtrations. The utility of this platform would be further enhanced if multiple catalytic systems were to branch out from a single precursor. This is accomplished herein with carbonizable polyamide aerogels incorporating ferrocene in every repeat unit of their skeletal framework. Pyrolysis yields Fe(0) nanoparticles in graphitic pockets dispersed throughout the 3D matrix of monolithic nanoporous carbon. Those materials are active catalysts in their own right (e.g., in the reduction of nitrobenzene to aniline). Most importantly though, Fe(0) was replaced by precious metal nanoparticles, illustratively by Au, Pt, Pd, Co, Ni, Ru, and Rh, by dipping the Fe-doped C-monoliths in solutions of the respective ions. The new monoliths were catalytically active towards typical processes of the corresponding metals, such as oxidation of benzyl alcohol to benzaldehyde (Au or Pt), or the Heck coupling reaction of iodobenzene with styrene (Pd), as described in the additional examples below. In another embodiment, recyclability was demonstrated by pulling the catalytic monoliths out of the reaction mixtures and placing them in fresh solutions of the reactants. Each process was repeated up to five times without a significant compromise of the catalytic activity.

Thus, in one embodiment, described herein is a composition of matter comprising a carbonizable polymer incorporating ferrocene in every repeat unit. In one aspect, this carbonizable polymer includes a polyamide. In another aspect, this carbonizable polymer includes a mixture of polyamide and polyurea. This carbonizable polymer is obtained by a process that comprises the preparation steps described herein for generating ferrocene-based polyamide aerogels.

In another embodiment, disclosed herein is a process for carbonizing the carbonizable polymer that incorporates ferrocene. This process comprises the step of pyrolyzing said ferrocene-incorporating polymer as described herein, to yield a nanoporous product that includes Fe(0) nanoparticles in graphitic pockets dispersed throughout the 3D matrix of

TABLE FA-11

Catalytic reaction results for pFc-PA and tFc-PA(Au, Pt, Pd) aerogels.

| Catalyst | Reaction Type | Temperature (° C.) | Time (hrs) | Conversion (%) | Aerogel quantity |
|---|---|---|---|---|---|
| pFc-PA | Reduction of nitrobenzene | 100 | 3 | 100 | 1% by mol |
| tFc-PA-Au | Oxidation of alcohol | 60 | 5 | 100 | 5% w/w |
| tFc-PA-Pt | Oxidation of alcohol | 60 | 5 | 100 | 5% w/w |
| tFc-PA-Pd | Heck coupling reaction (1) | 80 | 3 | 100 | 5% w/w |
| tFc-PA-Pd | Heck coupling reaction (2) | 80 | 8 | 80 | 5% w/w | monolithic nanoporous carbon, alternatively referred to herein as Fe-doped C-monoliths or simply Fe@C. In a related embodiment, disclosed herein is a composition of matter comprising said Fe-doped C-monoliths.

In another embodiment, disclosed herein is a process for partial or complete transmetalation of said Fe-doped C-monoliths, to yield a monolithic nanoporous carbon product wherein the Fe(0) has been partially or completely replaced by another metal species M, said transmetalation product alternatively referred to herein as M-doped C-monoliths or simply as M@C or as tm-M@C; wherein M is selected from the group consisting of Fe, Au, Pt, Pd, Co, Ni, Ru, and Rh. In one aspect, said process comprises the step of dipping the Fe-doped carbon monoliths in solutions of the respective metal ions, as described herein. In another aspect, said process may include the use of galvanic conditions, as described herein.

In a related embodiment, disclosed herein are compositions of matter comprising said M-doped C-monoliths, wherein M is selected from the group consisting of Au, Pt, Pd, Co, Ni, Ru, and Rh. In one aspect, these compositions include at least 50% v/v porous materials consisting of at least 50% w/w of carbon, which in turn includes a substantial amount of disordered graphite, and contains in dispersed form nanoparticles of metal M, i.e., M-nanoparticles, in a w/w ratio of from about 1% to about 50%. It is to be understood that similar compositions of matter comprising metals other than those listed may also be generated by those skilled in the art using the process disclosed herein.

In another embodiment, disclosed herein is a method of catalyzing chemical reactions by using one or more of the M-doped C-monoliths described herein as catalysts. This method comprises the step of contacting a reaction mixture with a catalytic amount of one or more M-doped C-monoliths; wherein M is selected from the group consisting of Au, Pt, Pd, Co, Ni, Ru, and Rh.

Example 42

Ferrocene-based polyamide wet-gels were synthesized according to FIG. 31 from ferrocene dicarboxylic acid (Fc(COOH)$_2$) and an aromatic triisocyanate (TIPM). The latter is a known precursor of carbonizable polyureas, polyurethanes, polyimides and other polyamides. The primary reaction product of —N=C=O and —COOH is a mixed carbamic anhydride adduct, which may proceed to —NH(CO)— either via unimolecular rearrangement, or via a disproportionation to urea and acid anhydride that react further to the amide. This isocyanate route to the ferrocene-based polyamide was preferred over a more conventional synthesis that would involve acid chlorides and amines, because of the commercial availability of TIPM in bulk quantities and the fact that the side product was $CO_2$ rather than HCl that has to be captured. Wet-gels were washed with the gelation solvent (DMF), solvent-exchanged with acetone and were dried in an autoclave with liquid $CO_2$ taken out as a supercritical fluid. The resulting materials are referred to as FcPA-xx, whereas xx denotes the total monomer weight percent in the sol, and was varied in the range 5≤xx≤25 (for the exact formulations refer to Table FA-12 below).

TABLE FA-12

Formulations and gelation times of FcPA-xx aerogels.

| Sample [a] | FDA | | | | Desmodur RE | | TIPM | | | DMF | | gelation |
|---|---|---|---|---|---|---|---|---|---|---|---|---|
| | mass (g) | volume [b] (mL) | mmol | C (M) | volume (mL) | mass [c] (g) | mass [d] (g) | mmol | C (M) | mass (g) | volume (mL) | time 90° C. |
| Fc-PA-5  | 0.411 | 0.244 | 1.5 | 0.093 | 1.33 | 1.359 | 0.367 | 1.00 | 0.062 | 13.79 | 14.52 | ~3 h |
| Fc-PA-10 | 0.411 | 0.244 | 1.5 | 0.190 | 1.33 | 1.359 | 0.367 | 1.00 | 0.126 | 6.01 | 6.32 | 2 h 30 min |
| Fc-PA-15 | 0.411 | 0.244 | 1.5 | 0.289 | 1.33 | 1.359 | 0.367 | 1.00 | 0.193 | 3.41 | 3.60 | 2 h 15 min |
| Fc-PA-20 | 0.411 | 0.244 | 1.5 | 0.394 | 1.33 | 1.359 | 0.367 | 1.00 | 0.262 | 2.12 | 2.23 | ~2 h |
| Fc-PA-25 | 0.411 | 0.244 | 1.5 | 0.502 | 1.33 | 1.359 | 0.367 | 1.00 | 0.335 | 1.34 | 1.41 | 1 h 45 min |

[a] Numeral extensions in sample names designate the % w/w total monomer (FDA + TIPM) concentration in the sol.
[b] The volume of FDA was calculated based on its density measured by helium pycnometry (1.685 g cm$^{-3}$).
[c] The mass of commercial Desmodur RE was calculated based on its density as that was measured in our laboratory (1.022 g cm$^{-3}$).
[d] The mass of TIPM in Desmodur RE was calculated based on the 27% w/w concentration given by the manufacturer.

Figure 32:
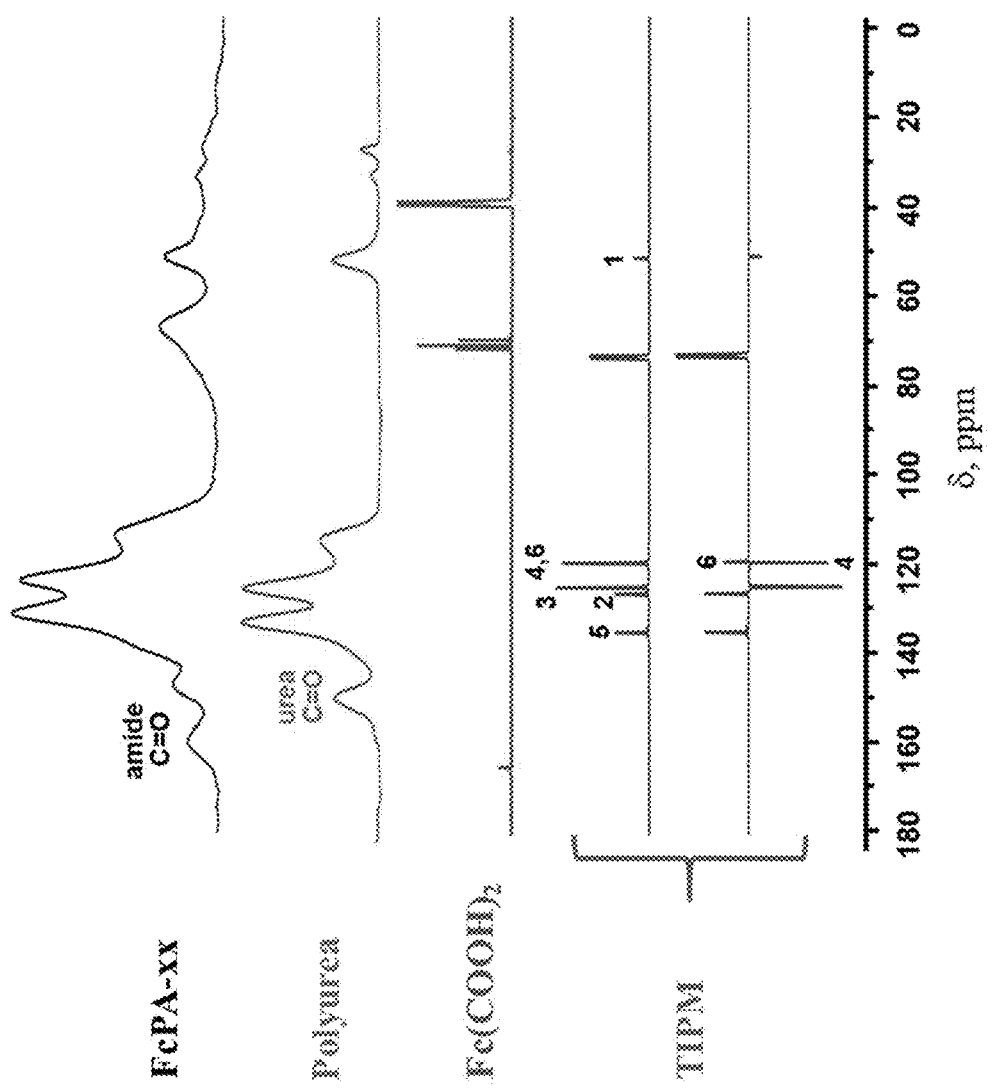
FIG. 32 displays solid-state CPMAS $^{13}$C NMR of FcPA-xx.

Solid-state CPMAS $^{13}$C NMR of FcPA-xx (FIG. 32) confirms incorporation of ferrocene into the polymer (refer to the cyclopentadienyl resonances at 70-75 ppm), and shows the expected resonance of the —NH($\underline{C}$O)— at 166.90 ppm. No residual —$\underline{C}$OOH was detectable, while the resonance at 153.61 ppm was assigned to TIPM-derived polyurea (by comparison with an authentic sample synthesized independently and included in FIG. 32). The ratio of the carbonyl resonances, COamide:COurea=67:33, translates to amide:urea=1.02:1.00 mol/mol. That leads to a theoretical elemental composition of (% w/w), C, 71.2; H, 4.7; N, 8.7; Fe, 8.7; which was considered in good agreement with the experimental values, C, 64.34; H, 4.86; N, 8.57; (via CHN analysis), and Fe: 9._5±1._1 (via TGA in $O_2$, average of 8 samples).

FcPA-xx shrunk 35-41% in linear dimensions relative to the molds and are characterized by typical aerogel material properties (refer to Table FA-13). Bulk densities ($\rho_b$) and open porosities (Π) varied from 0.12 g cm$^{-3}$ and 92% v/v, respectively (at xx=5) to 0.49 g cm$^{-3}$ and 63% v/v (at xx=25). All $N_2$-sorption isotherms showed hysteresis loops, becoming progressively broader at higher densities. Accordingly, lower-density FcPA-5 were dominated by larger macropores (volume ratio, $V_{>300\_nm}/V_{1.7-300\_nm}$=4.2), moving in favor of smaller macropores and mesopores as density increased (e.g., for FcPA-25, $V_{>300\_nm}/V_{1.7-300\_nm}$=0.8). BET surface areas were in the 460-260 m$^2$ g$^{-1}$ range, in descending order with $\rho_b$. All skeletal frameworks consisted of random assemblies of nanoparticles (FIG. 33A). There was a good order-of-magnitude agreement (4-9 nm) between particle radii calculated from $N_2$ sorption data and primary particle radii from small angle x-ray scattering (SAXS) data. According to the latter, primary particles aggregated into densely-packed secondary particles, 3-6× the size of the primary particles, as commonly observed with sol-gel derived polymers.

TABLE FA-13

Characterization of the FcPA-xx aerogels.

| FcPA-xx-xx | linear shrinkage (%) [a,b] | bulk density, $\rho_b$ (g cm$^{-3}$) [a] | skeletal density, $\rho_s$ (g cm$^{-3}$) [c] | Π (% v/v) [d] | specific pore volume (cm$^3$ g$^{-1}$) | | | BET surface area, σ (m$^2$ g$^{-1}$) | average pore diameter (nm) | | particles radius (nm) | | |
|---|---|---|---|---|---|---|---|---|---|---|---|---|---|
| | | | | | $V_{Total}$ [e] | $V_{1.7-300\_nm}$ [f] | $V_{>300\ nm}$ [g] | | 4 V/σ[h] method | BJH[i] method | $r_j$ | $R_1$[k] | $R_2$[l] |
| 5  | 41 ± 0.50 | 0.123 ± 0.006 | 1.472 ± 0.004 | 92 | 7.451 | 1.448 | 6.003 | 456 | 14[67] | 42[63] | 4.4 | 4.98 | 29.11 |
| 10 | 39 ± 0.09 | 0.202 ± 0.008 | 1.342 ± 0.006 | 85 | 4.205 | 2.360 | 1.845 | 381 | 25[45] | 32[14] | 5.8 | 6.57 | 25.03 |
| 15 | 38 ± 0.03 | 0.340 ± 0.004 | 1.333 ± 0.005 | 74 | 2.196 | 0.983 | 1.213 | 308 | 28[14] | 20[12] | 7.3 | 3.94 | 21.97 |
| 20 | 37 ± 0.70 | 0.401 ± 0.003 | 1.363 ± 0.003 | 70 | 1.760 | 0.829 | 0.931 | 276 | 12[26] | 16[4.8] | 7.9 | 2.85 | 19.13 |
| 25 | 35 ± 0.10 | 0.490 ± 0.007 | 1.341 ± 0.005 | 63 | 1.295 | 0.719 | 0.576 | 258 | 12[26] | 13[4.7] | 8.6 | 5.66 | 17.48 |

Pyrolysis was conducted under flowing $H_2$ at different temperatures with middle-density FcPA-15 aerogels. All samples kept their cylindrical shape and remained monolithic. Results are summarized in FIG. 34. In brief (FIG. 35), at 400/500° C. α-Fe(0) was the only crystalline phase. Small amounts of cementite ($Fe_3C$) were noted from 600° C. and above, while at 1400° C. pyrolysis yielded an additional minor carbide phase (martensite: $Fe_{1.91}C_{0.09}$). [Note: For comparison, pyrolysis at 800° C. under Ar yielded cementite as the only iron crystalline phase; Fe(0) started being produced together with $Fe_3C$ only at 1200° C.]. From 800° C. and above samples were electrically conducting and crystalline phases included graphite (note the (002) reflection at 2θ=26.44°), consistent with the fact that Fe(0) is a low-temperature graphitization catalyst.

Fe(0) produced below 800° C. was not chemically accessible: (a) it could not be removed with acid (aqueous HCl); (b) did not show any catalytic activity associated with Fe(0); and, (c) could not be transmetalated with solutions of precious metal ions (see below). Those properties were recovered after soaking those samples in THF, pointing to iron covered and protected by tarry products from the degradation of the polymer. Thus, the minimum temperature at which samples were immediately ready for further processing appears to be 800° C. (coinciding with the appearance of graphitic carbon in XRD and the onset of electrical conductivity). Those samples are referred to as Fe@C and comprised the basis for further study. Table FA-14 summarizes relative material properties as a function of pyrolysis temperature.

FA-14). Combination of shrinkage and mass loss yielded Fe@C samples less dense (0.286±0.004 g cm$^{-3}$) than their parent monoliths (0.340±0.004 g cm$^{-3}$). The iron content in Fe@C (11.5±2.1% w/w, via TGA in $O_2$), was 40-50% w/w of what was expected (25.4%) had all iron in FePA-15 (9.5±1.1% w/w—see above) been retained. Without being bound by theory, it is speculated that during pyrolysis under $H_2$ a certain amount of the ferrocene-based caps of the polyamide component of the polymer cleave and get volatilized below their oxidation point during TGA under $O_2$. The skeletal density of Fe@C (2.4 g cm$^{-3}$) is the weighted average of iron (7.86 g cm$^{-3}$ at 11% w/w) and carbon (1.7 g cm$^{-3}$ at 89% w/w). That density for skeletal carbon was confirmed by removing Fe(0) with HCl (see below) and is at the low-end for sp$^2$-rich amorphous carbon (1.8-2.0 g cm$^{-3}$), despite some graphitization as noted in XRD (FIG. 35), suggesting the presence of some closed porosity. The total open porosity of Fe@C was calculated from the bulk and skeletal densities and was found equal to 88% v/v (vs 74% v/v of the parent FcPA-15), while the balance of pore sizes had shifted to larger macropores ($V_{>300\_nm}/V_{1.7-300\_nm}$=3.4, vs. 1.2 in FcPA-15). The BET surface area of Fe@C (369 m$^2$ g$^{-1}$) was higher than that of FcPA-15 (308 m$^2$ g$^{-1}$) with a significant portion (176 m$^2$ g$^{-1}$, 48% v/v) assigned to newly formed (open) micropores.

Microscopically, the skeletal framework of Fe@C consisted of nanoparticles on the same order as those in the parent FcPA-15 (FIG. 33B). The apparent particle radius calculated from $N_2$-sorption data (3.5 nm) was similar to the primary particle radius of FcPA-15 (7.3 nm). In TEM, Fe(0)

TABLE FA-14

Characterization of the product from pyrolysis of FcPA-15 at different temperatures.

| Pyrolisis temperature of FcPA-15 (° C.) | linear shrinkage (%) [a,b] | bulk density, $\rho_b$ (g cm$^{-3}$) [a] | skeletal density, $\rho_a$ (g cm$^{-3}$) [c] | Π (% v/v) [d] | specific pore volume (cm$^3$ g$^{-1}$) | | | BET surface area, σ (m$^2$ g$^{-1}$) | average pore diameter (nm) | | particle radius (nm) [r] |
|---|---|---|---|---|---|---|---|---|---|---|---|
| | | | | | $V_{Total}$ [e] | $V_{1.7-300\_nm}$ [f,g] | $V_{>300}$ | | 4V/σ[h] method | BJH[i] method | |
| 800 (Fe@C) | 68 ± 0.50 | 0.286 ± 0.004 | 2.40 ± 0.004 | 88 | 3.086 | 0.705 | 2.381 | 369 | 9[33] | 18[10] | 3.5 |
| Fe@C HCl treated | 68 ± 0.16 | 0.263 ± 0.010 | 1.70 ± 0.006 | 85 | 3.221 | 0.769 | 2.452 | 282 | 9[45] | 16[9.5] | 6.1 |
| 1000 | 69 ± 0.02 | 0.812 ± 0.008 | 1.89 ± 0.006 | 53 | 0.702 | 0.238 | 0.464 | 235 | 5[10] | 4[0.28] | 6.75 |
| 1200 | 83 ± 0.50 | 0.720 ± 0.004 | 1.49 ± 0.005 | 51 | 0.718 | 0.562 | 0.156 | 234 | 10[13] | 16[1.88] | 8.60 |
| 1400 | 86 ± 0.50 | 0.981 ± 0.003 | 3.56 ± 0.003 | 72 | 0.740 | 0.227 | 0.513 | 84 | 11[35] | 13[2.63] | 10.03 |

Figure 36:
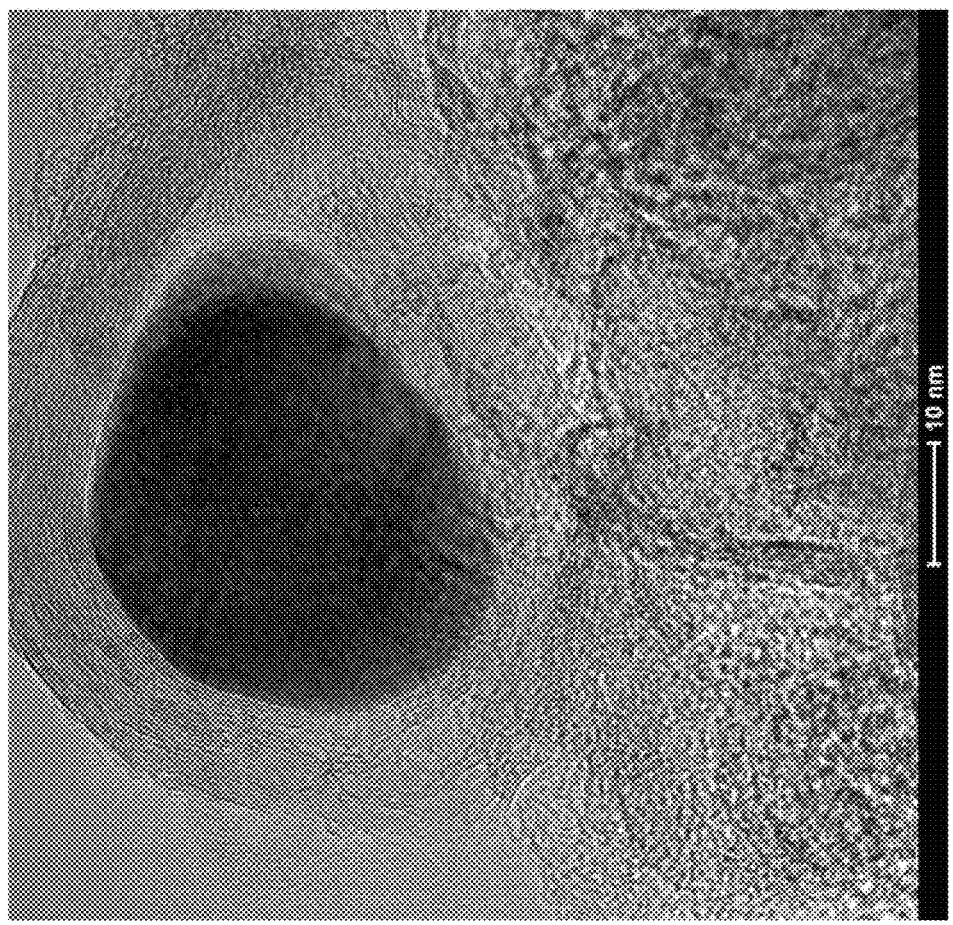
FIG. 36 displays TEM data of Fe@C. (A) TEM of Fe@C and Fe particle size distribution. (B) High resolution TEM of Fe@C. (C) High resolution TEM of Fe@C-acid.
Figure 36:
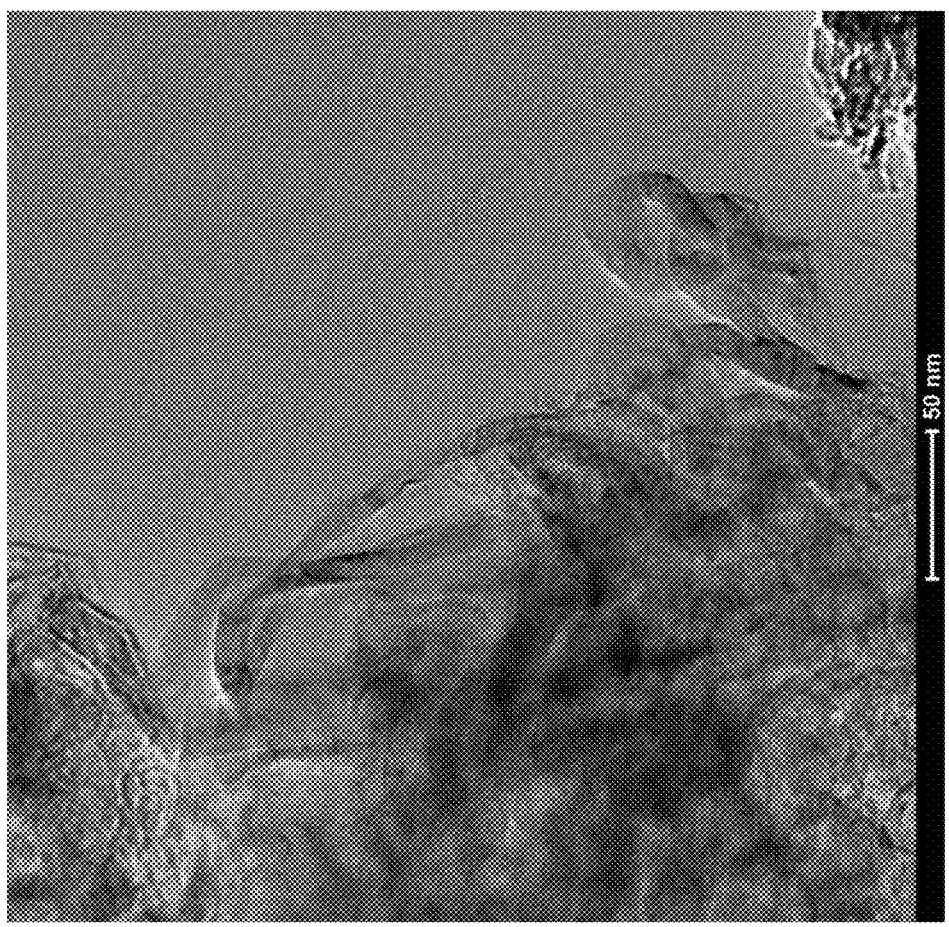

Upon pyrolysis at 800° C./$H_2$, FcPA-15 lost about 60% of their mass (char yield 37.3±1.9% w/w) and shrunk an additional 56% for a total linear shrinkage of 68% relative to the original molds. (Pyrolysis at even higher temperatures caused more shrinkage, e.g., 86% at 1400° C.—Table particles were distributed fairly evenly throughout the carbon network (FIG. 36A). The maximum of the particle distribution (FIG. 36A-Inset) was at 76.3 nm, however the average particle size calculated from that distribution (52±1 nm) matched the crystallite size of Fe(0) calculated via the Scherrer equation from the (111) reflection in XRD (52±1 nm). Under higher magnification, Fe(0) particles were shrouded in graphitic ribbons (FIG. 36B), which extended beyond the immediate vicinity of the iron particles and formed an entangled network fading away in the surrounding matrix, presumably amorphous carbon. The ribbon around the particle of FIG. 36B consists of about 28 graphene layers and is 9.48 nm thick. The interlayer spacing (3.39 Å) is longer than that of graphite (3.35 Å), consistent with Raman data showing the characteristic D and G bands of disordered graphite. The graphene layer stuck height (La) that was calculated via Knight's formula using the ratio of the areas of the D and G bands ($I_D/I_G$=2.27) was 16.9 nm, that is on the same order as the thickness of the ribbon in FIG. 36B. Importantly, iron nanoparticles were chemically accessible throughout that structure, and they could be removed by treating with concentrated HCl, leaving behind empty graphitic pockets (FIG. 36C). In addition to the skeletal densities of those samples (1.7 g cm$^{-3}$), which, as mentioned above, agree with those of Fe@C after correction for the Fe(0) content, macroscopically no further shrinkage was observed by HCl-treatment and the $N_2$-sorption isotherms of the two materials were quite similar. BET surface areas after HCl-treatment were somewhat compromised (282 m$^2$ g$^{-1}$ vs 369 m$^2$ g$^{-1}$ before HCl-treatment), yet 40% of that area (113 m$^2$ g$^{-1}$) was still assigned to micropores (vs. 48% before acid treatment).

Figure 34:
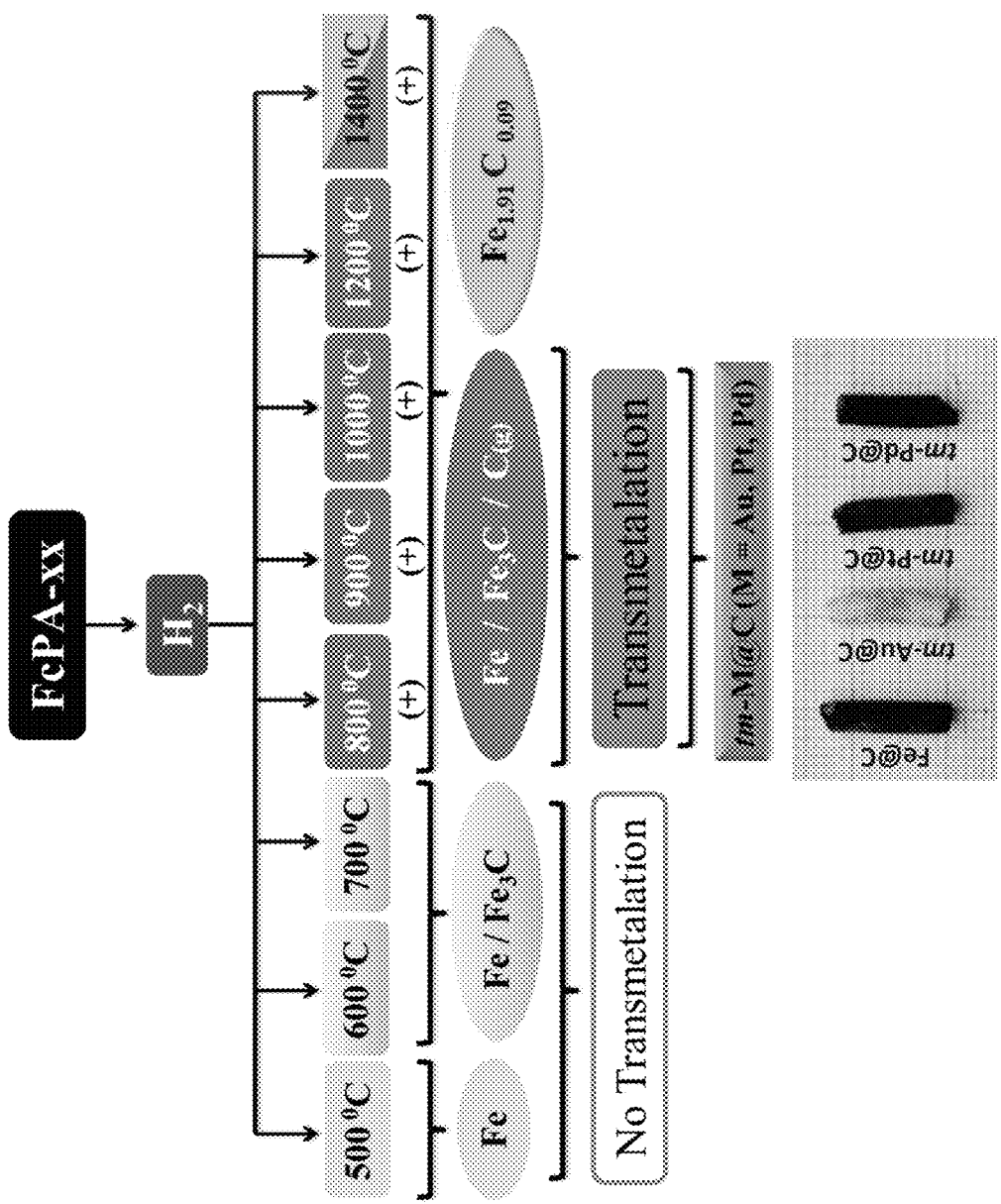
FIG. 34 displays pyrolysis and transmetalation summary results.
Figure 35:
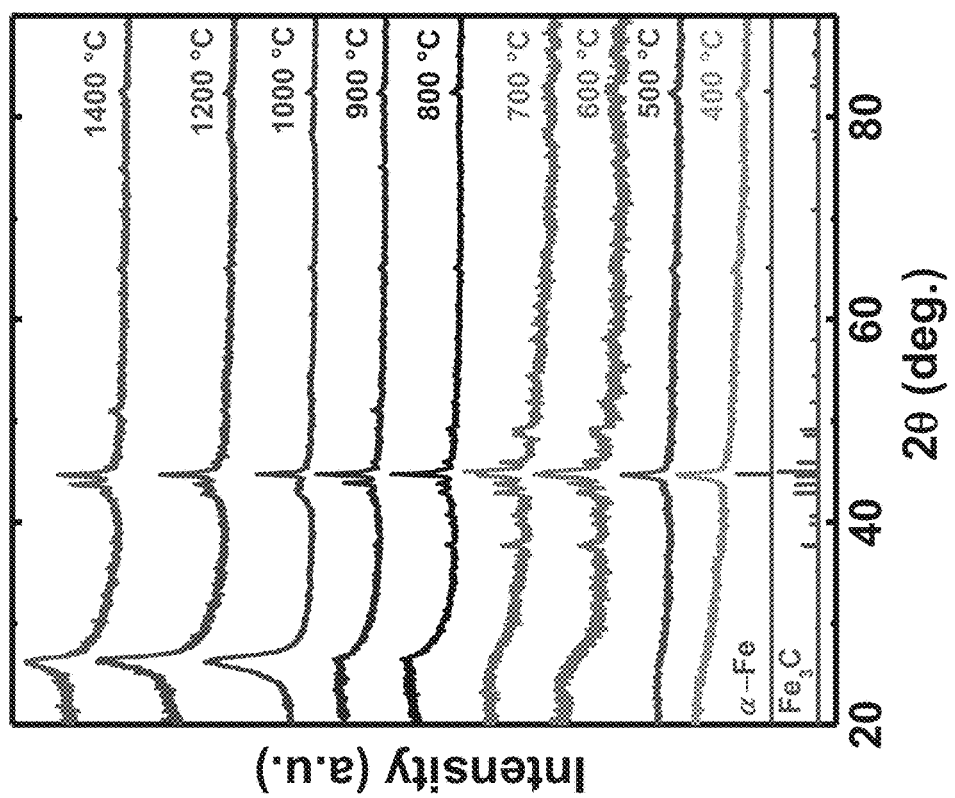
FIG. 35 displays XRD data from 400-1400° C.
Figure 37:
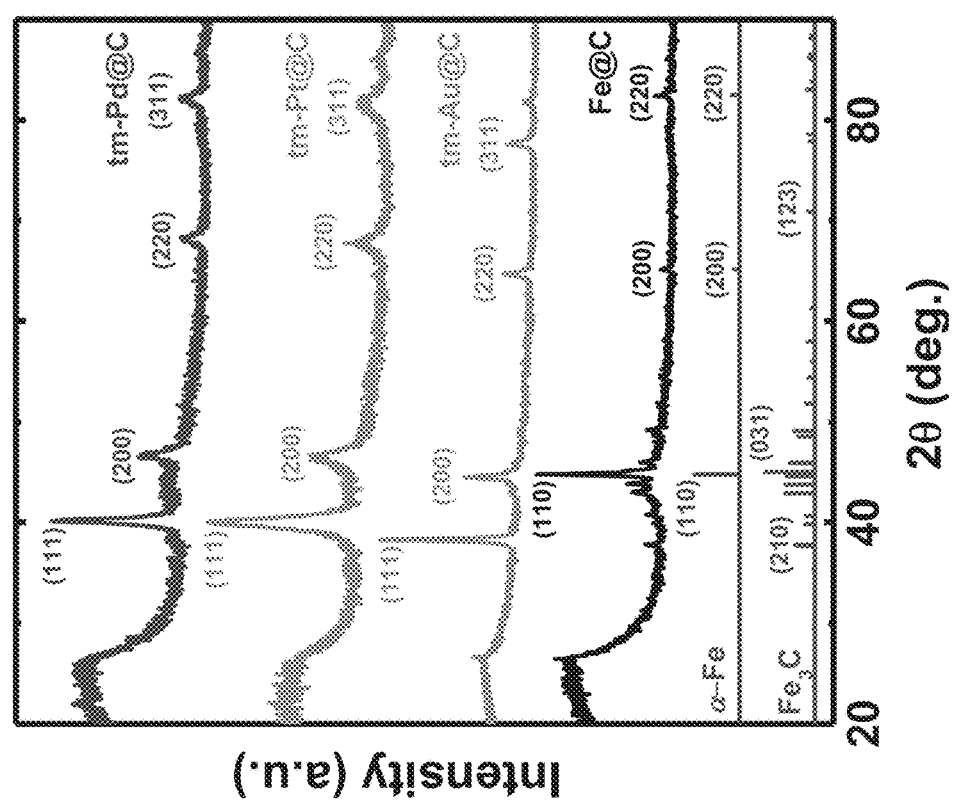
FIG. 37 displays XRD of transmetalated aerogels.
Figure 38:
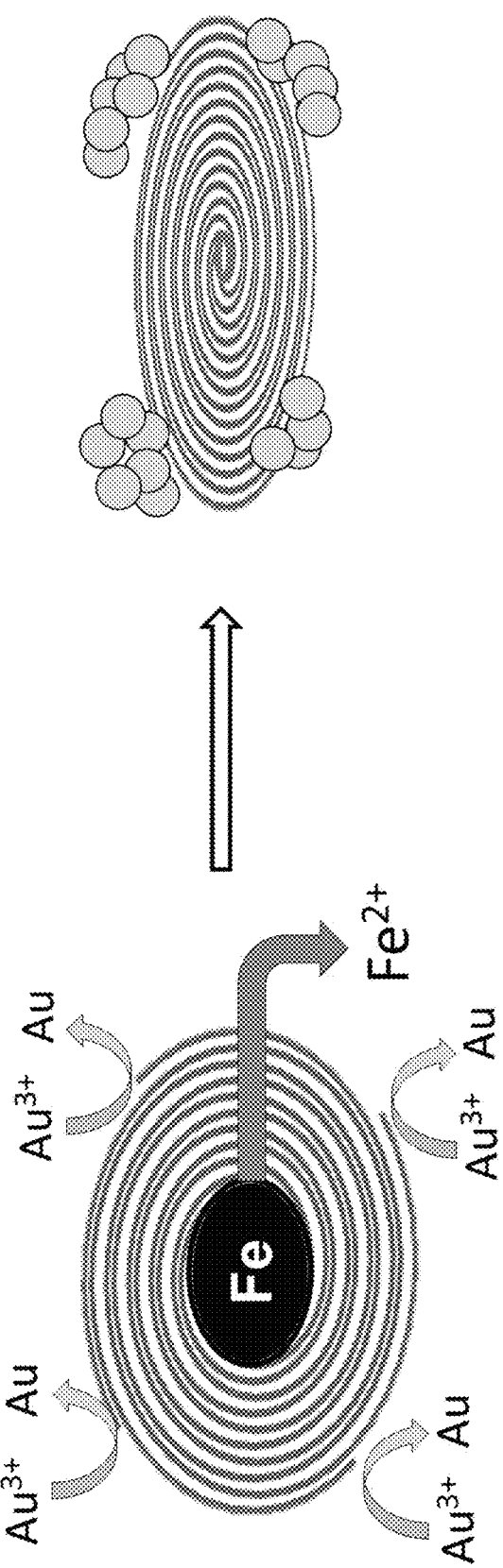
FIG. 38 displays a mechanistic scheme of galvanic transmetalation.

That chemical accessibility of the embedded iron nanoparticles was utilized in order to replace Fe(0) with Au, Pt or Pd (M) via reaction with ions of the corresponding elements, $M^{n+}$, according to: n Fe(0)+2 $M^{n+}$→n $Fe^{2+}$+2 M(0). All three reactions are highly exothermic with redox potentials over 1.0 V. Fe@C monoliths were infiltrated by capillary action under reduced pressure with aqueous solutions of $M^{n+}$. Transmetalated (tm-) monoliths (referred to as tm-M@C) were washed with water, then acetone and were dried under ambient pressure with retention of the size and shape of the original Fe@C samples (FIG. 34). Porosities remained the same (86-90% v/v) as in the parent Fe@C (88% v/v). The XRD spectra of tm-M@C were dominated by the corresponding metals (FIG. 37); minor residual reflections were identified with Fe$_3$C. Data from TGA-in-O$_2$ were in line with quantitative replacement of Fe(0) (at 11.5% w/w) by the precious metal (M % w/w, expected/found: Au, 31.4±4.4/33.6±8.8; Pt, 31.2±4.4/34.5±0.8, Pd, 19.9±2.1/19.8±1.8). Applying the Scherrer equation to the (111) reflections in XRD gave significantly smaller average crystallite sizes (Au, 15.2±0.5 nm; Pt, 20.9±0.7 nm; Pd, 21.4±0.7 nm) than those found for Fe(0) in Fe@C (52±1 nm). According to TEM those precious metal crystallites formed clusters unrelated to the graphitic pockets shrouding the parent iron particles in Fe@C. In fact, no graphitic pockets could be identified at all, consistent with a nanoscopic collapse of the network. The latter is supported (Table FA-15) by an increase of $V_{>300\_nm}/V_{1.7-300\_nm}$ from 3.4 in Fe@C to 12.4 (tm-Au@C), 15.6 (tm-Pt@C) and 6.7 (tm-Pd@C) and a reduction of the BET surface area from 369 m$^2$ g$^{-1}$ in Fe@C to 100-133 m$^2$ g$^{-1}$ in tm-M@C (Table FA-15). The nanoscopic collapse that is inferred from these data is not related to the surface tension forces exerted on the network by the evaporating solvent; had that been the case, tm-M@C would had shrank microscopically. In fact, and without being bound by theory, these data may suggest that the mechanism of removing Fe(0) by $M^{n+}$ was different from that by H$^+$. At this point it is noted that bulk iron dipped in gold platting solutions is passivated by a layer of metallic gold and further dissolution stops. The complete consumption of Fe(0) nanoparticles, rather than formation of Fe-core/Au-shell particles, points to a galvanic process akin to bulk corrosion whereas, in this case, electrically conducting graphitic ribbons played the role of a conduit that spatially separated the anode [metallic Fe(0)] from the cathode—any tip of the ribbons along their network (FIG. 38). According to this model, initial reduction of precious metal ions is favored at the points of least resistance, which become the de facto points of nucleation and growth. Since there is a large number of such points for every Fe(0) particle, we ended up with clusters of smaller crystallites of Au, Pt or Pd than the parent iron particles. This is particularly advantageous for applications in catalysis, because, for example, Au demonstrates catalytic activity only at nanoscopic sizes.

TABLE FA-15

Characterization of the transmetalation products from Fe@C.

| tm-M@C | linear shrinkage (%)[a,b] | bulk density, $\rho_b$ (g cm$^{-3}$)[a] | skeletal density, $\rho_s$ (g cm$^{-3}$)[c] | Π % (v/v)[d] | specific pore volume (cm$^3$ g$^{-1}$)[c] | | | BET surface area, σ (m$^2$ g$^{-1}$) | average pore diameter (nm) | | particle radius (nm) |
|---|---|---|---|---|---|---|---|---|---|---|---|
| M | | | | | $V_{Total}$[e] | $V_{1.7-300\_nm}$[f] | $V_{>300}$[g] | | 4V/σ[h] | BJH[i] | r[j] |
| Au | 69 ± 0.02 | 0.190 ± 0.003 | 1.96 ± 0.038 | 90 | 4.753 | 0.354 | 4.399 | 101 | 18[14] | 17[7.86] | 15.15 |
| Pt | 70 ± 0.02 | 0.191 ± 0.004 | 1.87 ± 0.016 | 89 | 4.701 | 0.284 | 4.417 | 100 | 18[17] | 10[1.69] | 16.04 |
| Pd | 70 ± 0.05 | 0.216 ± 0.008 | 1.98 ± 0.018 | 86 | 7.124 | 0.533 | 3.591 | 133 | 12[16] | 17[5.07] | 11.39 |

[a]Average of 3 samples.
[b]Linear shrinkage = 100 × (mold diameter − sample diameter)/(mold diameter).
[c]Single sample, average of 50 measurements.
[d]Porosity, Π = 100 × ($\rho_s - \rho_b$)/$\rho_s$.
[e]Calculated via $V_{Total} = (1/\rho_b) - (1/\rho_s)$.
[f]Cumulative volume of pores between 1.7 nm and 300 nm from $N_2$-sorption data and the BJH desorption method.
[g]$V_{>300\_nm} = V_{Total} - V_{1.7-300\_nm}$.
[h]For the first number, V was taken equal to $V_{Total} = (1/\rho_b) - (1/\rho_s)$; for the number in [brackets], V was set equal to the maximum volume of $N_2$ absorbed along the isotherm as P/Po→1.0.
[i]From the BJH plots: first numbers are peak maxima; numbers in (parentheses) are full widths at half maxima.
[j]Particle radius, r = 3/($\rho_s$ ×σ);
[k]R$_1$: radius of primary particles from SAXS;
[l]R$_2$: radius of secondary particles from SAXS.

Figure 39:
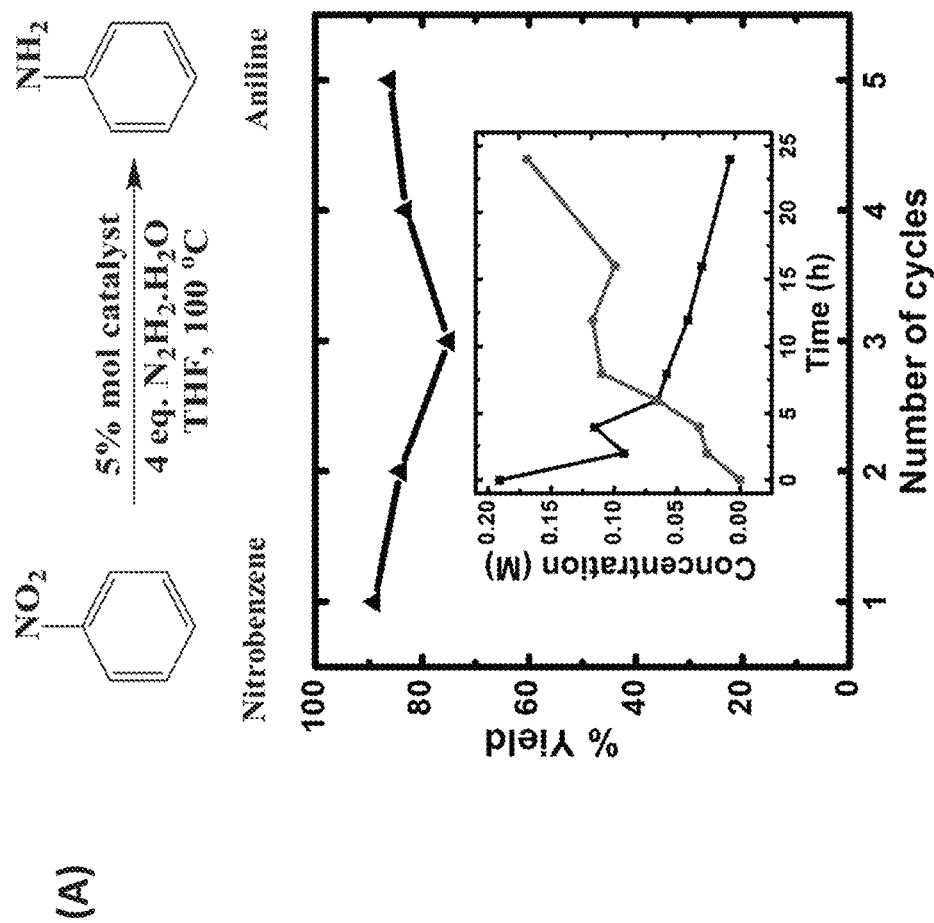
FIG. 39 displays various catalysis data. (A) Reduction of nitrobenzene to aniline using Fe@C. (B) Oxidation of benzyl alcohol to benzaldehyde using tm-Au@C. (C) Oxidation of benzyl alcohol to benzaldehyde using tm-Pt@C. (D) Iodobenzene/butyl acrylate Heck coupling using tm-Pd@C. (E) Iodobenzene/styrene Heck coupling using tm-Pd@C.
Figure 39:
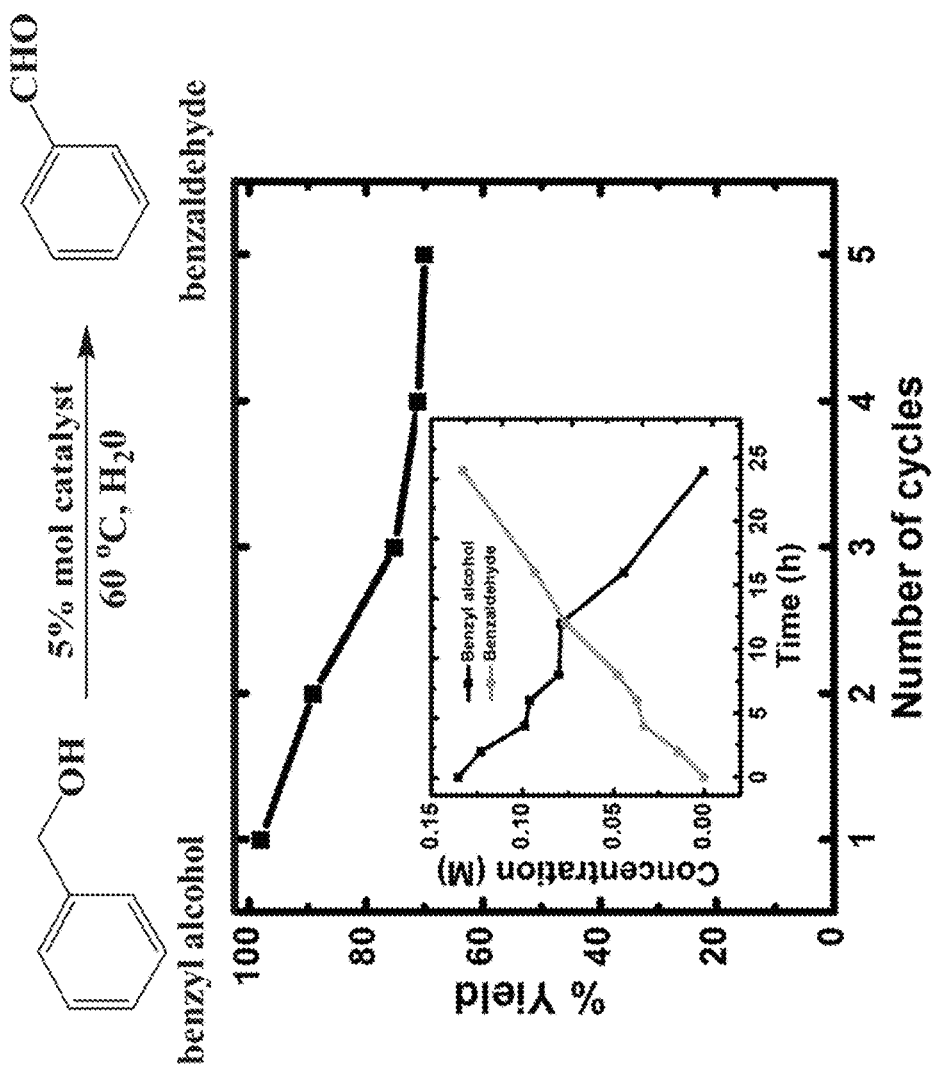
Figure 39:
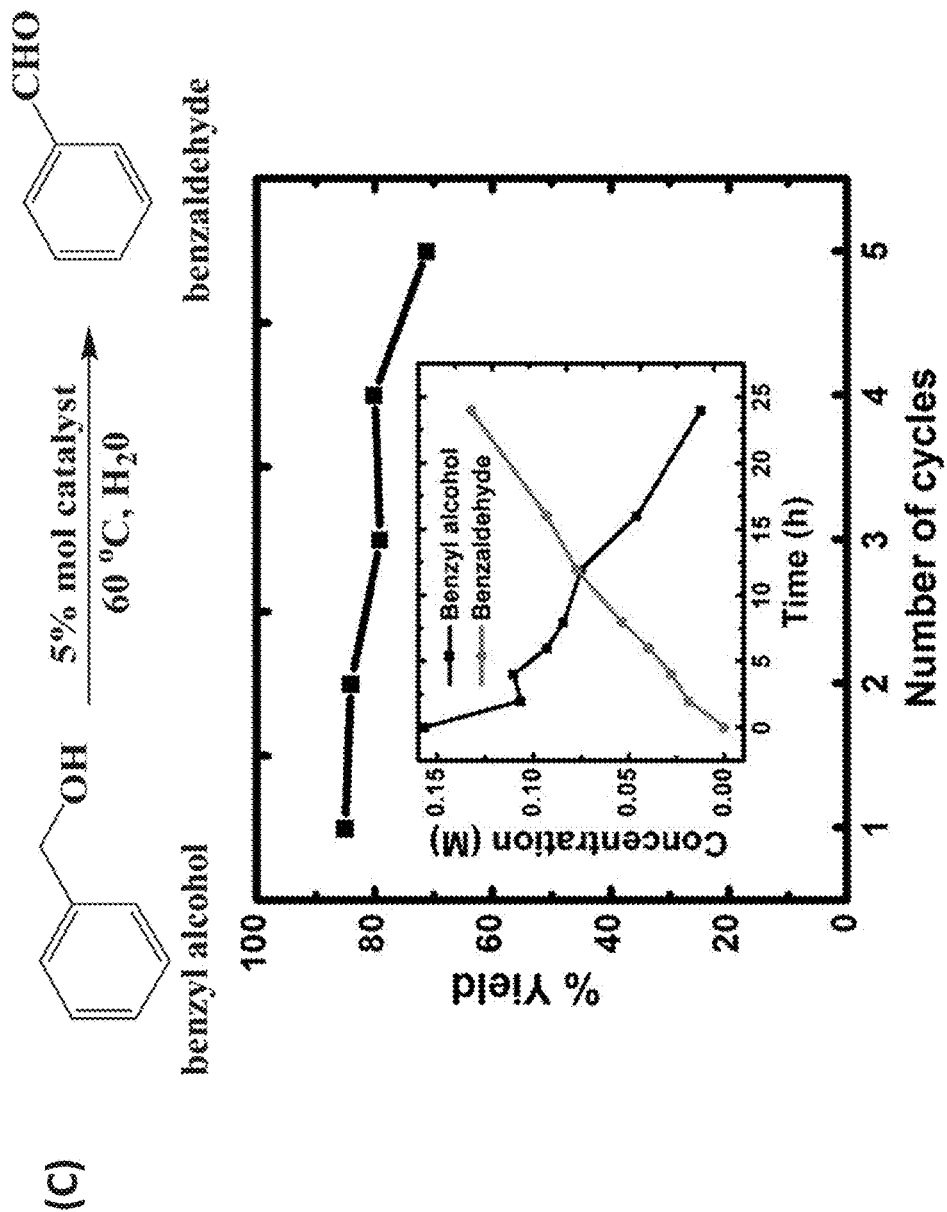
Figure 39:
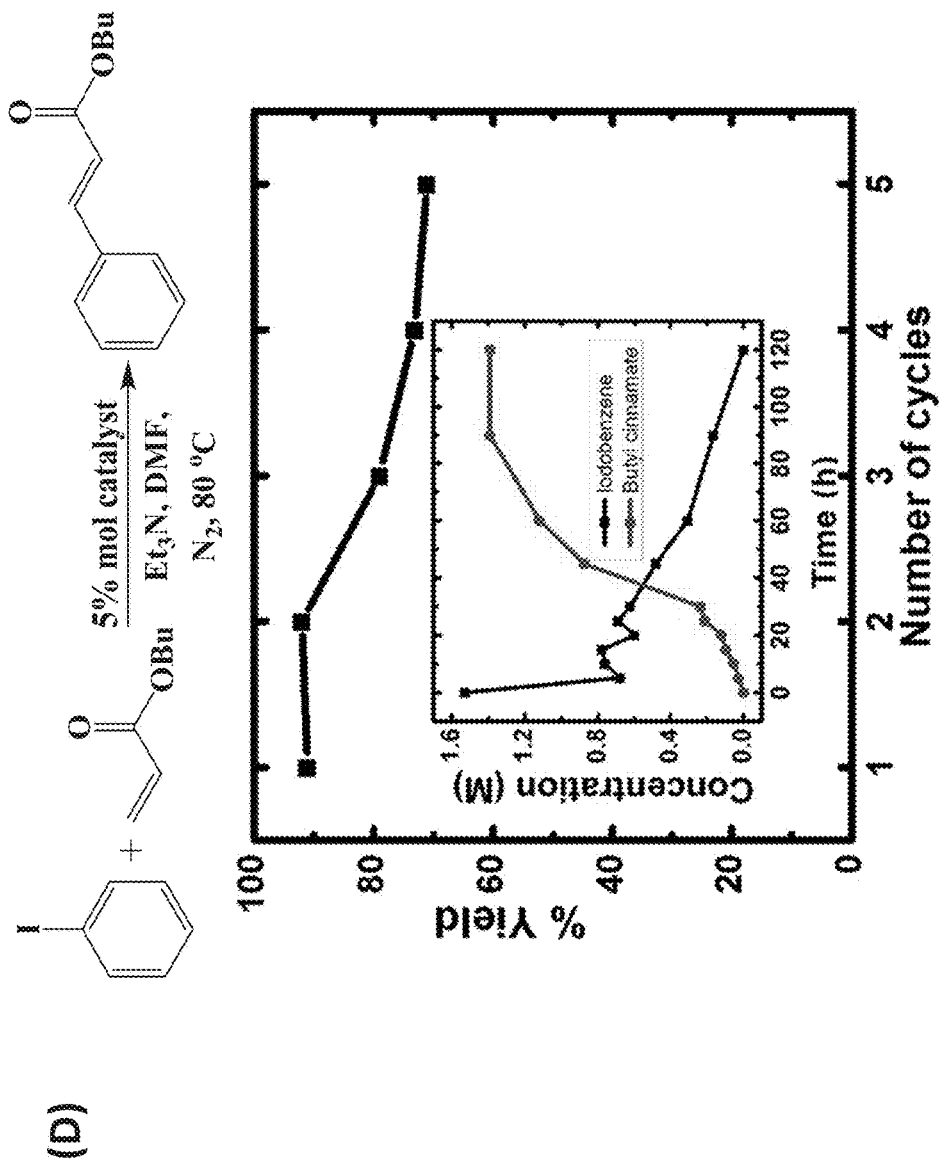
Figure 39:
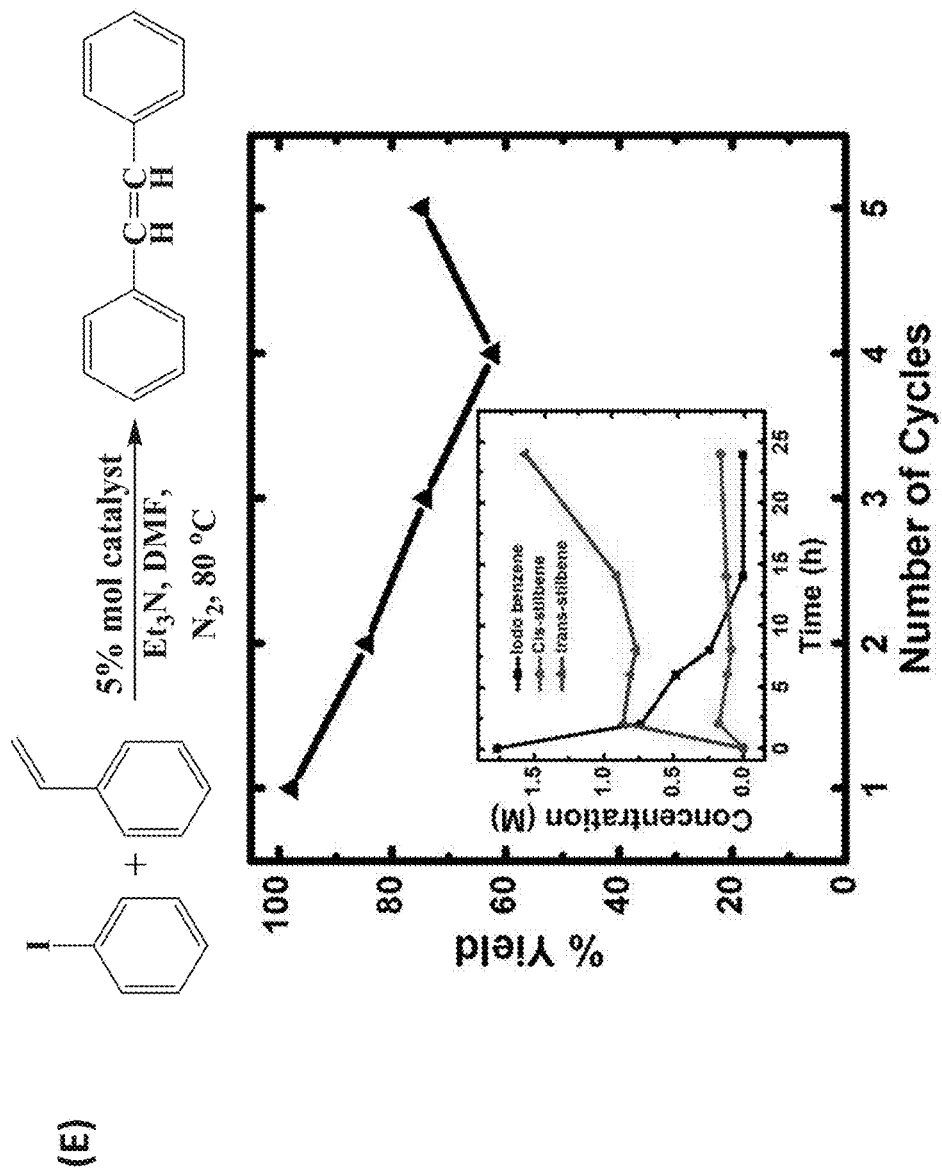

The catalytic activity of Fe@C and tm-M@C was investigated with standard solution-phase reactions of the corresponding metals. The catalytic monoliths were dipped in dilute solutions of the corresponding reaction mixtures for 24 h under vigorous magnetic stirring and bubbling of $N_2$ or $O_2$, depending on the reaction. The amount of the limiting reagent was adjusted based on the weight of the monolith and the amount of the metal (Fe, Au, Pt or Pd) in it, so that the latter was always at 5% mol/mol of the limiting reagent. The amount of solvent was adjusted, and catalytic reactions were run with both high (0.9 M) and low (0.1 M) concentrations of the limiting reagents. Aliquots were taken in regular intervals and were analyzed chromatographically. Typical results are shown in FIG. 39. At the end of the 24 h period, each catalytic monolith was removed from the reaction mixture with a pair of tweezers, rinsed briefly with the reaction solvent and was transferred into a new reaction mixture. The procedure was repeated five times with each catalyst, and final yields are summarized in Table FA-16. All catalytic monoliths were robust, and survived the prolonged 5-day "beating" by the magnetic stirrer. Control experiments used Fe@C monoliths whereas Fe had been removed with HCl. Control experiments with tm-M@C included use of pre-transmetalation monoliths (Fe@C), while in the case of tm-Au@C catalysis was also attempted with a 2 in² gold foil put in the reaction mixture for a few days. No product was observed in any of the controls. Overall, 24 h yields with all catalysts started from somewhat higher values in the first two cycles. The rate of losing catalytic activity after the third cycle was slower for all catalysts, and all 24 h yields after the fifth cycle were always higher than 70%. Along those lines it is noteworthy that catalysis of the oxidation of benzyl alcohol to benzaldehyde with tm-Au@C gave essentially identical results with tm-Pt@C, pointing to the effectiveness of our procedure in terms of furnishing well-dispersed catalytic Au nanoparticles.

lower, and therefore a higher portion of the thermodynamic potential would become available for reduction. Indeed, preliminary results showed that FcPA-15 samples processed at 1,200° C. were successfully transmetalated with all four Co, Ni, Ru, Rh.

Example 43

Additional Materials: All reagents and solvents were used as received, unless noted otherwise. Ferrocene, aluminum chloride, acetyl chloride, lithium aluminum hydride, sodium hydroxide, dichloromethane, hexane, anhydrous N,N-dimethylformamide (DMF), butyl acrylate, styrene (inhibitor was removed by extraction with 5 M solution of NaOH followed by drying with anhydrous sodium sulphate), acetophenone, hexadecane, benzaldehyde, iodobenzene, benzyl alcohol, butyl cinnamate, trietyl amine, cis- and trans-stilbene, chloroplatinic acid hydrate, palladium chloride and concentrated HCl (12.1 N) were purchased from Sigma Aldrich Chemical Co. Gold plating solution were purchased from Alfa Aesar (catalog number: 42307), Deuterated DMSO (DMSO-$d_6$) was obtained from Cambridge Isotope Laboratories Inc. Tris(4-isocyanatophenyl)methane (TIPM) was donated from Bayer Corp. USA as a 27% w/w solution in dry ethylacetate under the trade name of Desmodur RE. Argon (99.99999%), $H_2$ (99.999%) were purchased from Ozark Gas (Rolla, Mo.).

Example 44

1,1'-Ferrocene dicarboxylic acid (Fc(COOH)$_2$) was prepared in two steps from ferrocene following literature procedures, as shown in Eq. FA-1 above. Yield: 63%; mp 250° C. (sublimed). $^1$H NMR (400 MHz, DMSO-$d_6$) δ 4.47 (d,

TABLE FA-16

Reaction yields by recycling the catalysts as indicated.

| | | 24 h Yield % mol/mol | | | | |
|---|---|---|---|---|---|---|
| Catalyst | Reaction | 1$^{st}$ cycle | 2$^{nd}$ cycle | 3$^{rd}$ cycle | 4$^{th}$ cycle | 5$^{th}$ cycle |
| Fe@C | nitrobenzene + hydrazine ---> aniline | 89 | 84 | 75 | 83 | 86 |
| tm-Au@C | benzyl alcohol + O$_2$ ---> benzaldehyde | 98 | 89 | 75 | 71 | 70 |
| tm-Pt@C | benzyl alcohol + O$_2$ ---> benzaldehyde | 85 | 84 | 79 | 80 | 71 |
| | Heck Couplings: | | | | | |
| tm-Pd@C | iodobenzene + styrene ---> cis- + trans-stilbene | 98 | 84 | 74 | 62 | 75 |
| tm-Pd@C | iodobenzene + butyl acrylate ---> butyl cinnamate | 91 | 92 | 79 | 73 | 71 |

Thus, in an embodiment of the invention herein, ferrocene-based polyamide aerogels have served as the point of departure for the synthesis of robust monolithic macroporous carbon-supported nanosized precious metal catalysts, whose great attribute is their convenient recyclability.

In another embodiment, the ferrocene-based unifying platform herein has been expanded to other supported catalysts in addition to Au, Pt, Pd. However, initial transmetalation attempts of Fe@C with Co$^{3+}$, Ni$^{2+}$, Ru$^{3+}$, Rh$^{3+}$ were not successful, despite that the corresponding redox processes with Fe(0) are thermodynamically favorable. Without being bound by theory, it was thought that the galvanic-replacement mechanism of transmetalation points to kinetic limitations by the ohmic resistance of the carbon network as a possible reason for that. Thereby, again without being bound by theory, it was hypothesized that samples obtained at higher temperatures, with higher graphite content should be more conducting, their internal ohmic drop should be 4H), 4.72 (d, 4H), 12.34 (s, 2H). $^{13}$C NMR (400 MHz, DMSO-$d_6$) δ 171, 73, 72, 71; IR (KBr) 3429, 1687, 1495, 1301, 514 cm$^{-1}$. Elemental Analysis, (CHN). Theoretical % w/w for $C_{12}H_{10}O_4Fe$: C, 52.55; H, 4.38. Found: C, 51.83; H, 4.13.

Example 45

Figure 40:
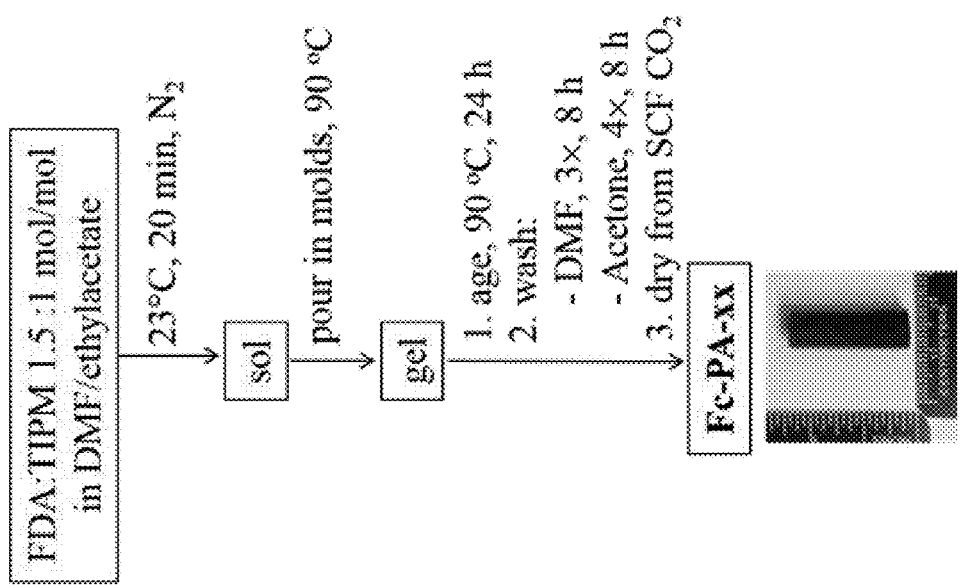
FIG. 40 displays a schematic synthesis of ferrocene polyamide aerogels (FcPA-xx).

Synthesis of ferrocene polyamide aerogels (FcPA-xx). In a typical procedure (FIG. 40), Fc(COOH)$_2$ (4.11 g, 0.015 mol) was dissolved in anhydrous DMF and the solution was added to 13.6 g of Desmodur RE (containing 3.67 g, 0.01 mol of TIPM). The resulting sol was stirred at room temperature under $N_2$ for 20 min, and was poured in molds (Wheaton 4 mL Polypropylene Omni-Vials 1.04 cm in inner diameter, Fisher part No. 225402), which were then sealed and left for gelation at 90° C. The total weight percent of monomers (TIPM+Fc(COOH)$_2$) in the sol was varied by varying the amount of solvent (DMF), and is denoted by extension -xx in the sample names. All formulations and gelation times are summarized in Table FA-12. Gels were aged for 24 h at 90° C. in their molds. Subsequently, wet gels were removed from their molds, washed with DMF (3×, 8 h each time), acetone (4×, 8 h each time using, 4× the volume of the gel for each wash) and were dried with liquid $CO_2$ in an autoclave taken out at the end as a supercritical fluid (SCF).

Example 46

Preparation of Fe(0)-doped carbon aerogels (Fe@C). FcPA-xx aerogel monoliths were transferred into a MTI GSL1600X-80 tube furnace (alumina 99.8% pure, 72/80 mm inner/outer diameters, 457 mm heating zone). The temperature of the furnace was raised to the desired temperature (500-1400° C.) at 5° C. mint under flowing $H_2$ (150 mL min$^{-1}$) for 5 h. Samples were heated at those temperatures for 5 h. At the end of the heating period the temperature was returned to room temperature at 5° C. mint under constant flow of $H_2$. In particular, samples prepared at 800° C. are referred to as Fc@C. For control purposes, samples were also treated at 800° C. and 1200° C. under flowing Ar gas (150 mL min$^{-1}$) for 5 h.

Example 47

Transmetalation of Fe@C aerogels to noble-metal (M)-doped carbon aerogels (tm-M@C). Fe@C monoliths were transmetalated with noble metals (tm-M@C, M: Au, Pt, Pd) by dipping in the corresponding metal ion solutions. ([Au ions]=0.018; [$H_2PtCl_6$]=0.035 M; [$PdCl_2$]=0.035 M) under reduced pressure, right after they came out of the furnace. The volume of the precious metal solutions were adjusted based on the amount of expected Fe in the Fe@C monoliths, but in general the (volume of solution):(volume of the Fe@C monolith) was about 80. After 5 h in the respective transmetalation bath, monoliths were placed in water bath and were heated at around 50° C. for 5 h still under reduced pressure. Subsequently, they were washed (2×) with water followed by acetone (2×) and were vacuum-dried overnight at 80° C.

Example 48

Methods

Drying of wet-gels with supercritical fluid (SCF) $CO_2$ was carried out following standard procedure using an autoclave (SPIDRY Jumbo Supercritical Point Dryer, SPI Supplies, Inc. West Chester, Pa. or a Spe-edSFE system, Applied Separations, Allentown, Pa.).

Example 49

Physical Characterization

Bulk densities ($\rho_b$) were calculated from the weight and the physical dimensions of the samples. Skeletal densities ($\rho_s$) were determined with helium pycnometry using a Micromeritics AccuPyc II 1340 instrument.

Example 50

Chemical Characterization

Elemental analysis (CHN) was conducted with a PerkinElmer elemental analyzer (Model 2400 CHN). Infrared (IR) spectra were obtained in KBr pellets, using a Nicolet-FTIR Model 750 spectrometer. Raman spectroscopy of carbon samples was conducted with a Jobin-Yvon micro-Raman spectrometer with a 632.8 nm He—Ne laser as the excitation source. Gas chromatography (GC) was conducted with Hewlett Packard, 5890 Series II, with a DB-5 capillary column (30 m/0.25 mm) and Flame ionization detector (FID). Liquid $^1H$ and $^{13}C$-NMR spectra were recorded in deuterated solvents using a 400 MHz Varian Unity Inova NMR instrument (100 MHz carbon frequency). Solid-state $^{13}C$-NMR spectra were obtained with samples ground into fine powders on a Bruker Avance III 400 MHz spectrometer with a carbon frequency of 100 MHz, using magic-angle spinning (at 5 kHz) with broadband proton suppression and the CPMAS TOSS pulse sequence for spin sideband suppression. Solid-state $^{13}C$ NMR spectra were referenced externally to glycine (carbonyl carbon at 176.03 ppm).

Example 51

Structural Characterization

BET surface areas and pore size distributions for pore sizes in the 1.7-300 nm range were determined with $N_2$-sorption porosimetry at 77 K using a Micromeritics ASAP 2020 surface area and porosity analyzer. Scanning electron microscopy (SEM) was conducted with Au-coated samples on a Hitachi Model S-4700 field-emission microscope.

Transmission Electron Microscopy (TEM) was conducted with an FEI Tecnai F20 instrument employing a Schottky field emission filament operating at a 200 kV accelerating voltage. The samples were finely ground by hand in a mortar with a pestle and was mixed with isopropanol in 5 mL glass vials. The vials were ultrasonicated for 20 min to disperse the small particles in the solvent. After removing from the ultrasonic bath and just before particle settling was complete, a single drop was taken and placed on a 200 mesh copper grid bearing a lacey Formvar/carbon film. Grid was allowed to air-dry over night before microscopy. At least 6 different areas/particles were examined to ensure that the results were uniform over the entire sample.

Powder X-ray diffraction (XRD) was conducted with a PANalytical X'Pert Pro multipurpose diffractometer (MPD) with Cu Kα radiation (λ=1.54 Å) and a proportional counter detector equipped with a flat graphite monochromator. Phase composition was estimated via Rietveld refinement of the x-ray diffraction patterns utilizing RIQAS software (Materials Data, Inc., version 4.0.0.26). Structural information for crystalline phases was obtained from the ICSD database version 2.01. Crystallite sizes were calculated utilizing the Scherrer equation and the FWHM of the lowest-angle diffractions. A Gaussian correction for instrumental broadening was applied utilizing NIST SRM 660a $LaB_6$ to determine the instrumental broadening.

The fundamental building blocks of all aerogels were probed with small angle X-ray scattering (SAXS), using ~2 mm thick disks cut with a diamond saw. SAXS was conducted with the same PANalytical X'Pert Pro multipurpose diffractometer (MPD) configured for SAXS, using a ⅟₃₂° SAXS slit, a ⅟₁₆° antiscatter slit on the incident beam side, and a 0.1 mm antiscatter slit together with a Ni 0.125 mm automatic beam attenuator on the diffracted beam side. Samples were placed in circular holders between thin Mylar sheets, and scattering intensities were measured by running 2θ scans from −0.1° to 5° with a point detector in the transmission geometry. All scattering data were reported in arbitrary units as a function of Q, the momentum transferred during a scattering event. Data analysis was conducted using the Beaucage Unified Model applied with the Irena SAS tool for modeling and analysis of small angle scattering within the Igor Pro application (a commercial scientific graphing, image processing, and data analysis software from Wave Metrics, Portland, Oreg.).

Example 52

Thermal Characterization

Thermogravimetric analysis (TGA) was conducted under $N_2$ or $O_2$ with a TA Instruments Model TGA Q50 thermogravimetric analyzer, using a heating rate of 5° C. $min^{-1}$.

Example 53

Catalysis

Reduction of nitrobenzene was catalyzed with Fe@C Nitrobenzene (0.984 g, 8 mmol) was dissolved in THF (50 mL) using a thick jacketed round bottom pressure flask with Teflon screw-cap. Reducing agent hydrazine hydrate (0.641 g, 20 mmol), and internal standard hexadecane (1000 µL, 3 mmol) were added. The flask was sealed and the reaction mixture was stirred for 24 h at 100° C. Aliquots (100 µL) were taken every after 2 h by cooling the flask temporarily to 40° C., and were analyzed immediately with GC. After 24 h the reaction mixture was cooled down to room temperature, the Fe@C monolith was harvested out, rinsed with THF two times and was transferred to new reaction mixture for the next cycle. The whole catalytic process was repeated five times.

Oxidation of benzyl alcohol was catalyzed either with tm-Au@C or tm-Pt@C catalysts. Benzyl alcohol (0.864 g, 8 mmol) was dissolved in distilled water (50 mL), and acetophenone (1000 µL, 8 mmol) was added as an internal standard. The reaction mixture was heated with an oil bath at 60° C. under constant bubbling of oxygen and magnetic stirring. Aliquots (100 µL) were taken every 2 h, extracted with diethyl ether and were analyzed immediately with GC. After 24 h the reaction mixture was cooled down to room temperature, the tm-Au@C and tm-Pt@C monoliths were harvested out, rinsed with water two times and were transferred to new reaction mixture for the next cycle.

Heck coupling reactions were catalyzed with tm-Pd@C. These reactions were conducted under $N_2$ in DMF (5 mL) using iodobenzene (1.632 g, 8 mmol), trietyl amine (0.809 g, 8 mmol), butyl acrylate (1.28 g, 10 mmol) or styrene (1.04 g, 10 mmol) and hexadecane as internal standard (1000 µL, 3 mmol). The reactions were carried out at 80° C. while stirring with magnetic stirrer. The same protocol as above was observed for GC analysis and recycling of the catalyst.

All catalysts (Fe@C, tm-Au@C, tm-Pt@C, tm-Pd@C) were used at 5% mol/mol relative to reagent in the corresponding reaction mixtures. Quantifications was conducted using internal standards and response factors was calculated via calibration curves that were constructed with a series of samples containing known concentrations of the reactants and products. All catalytic reactions were repeated five times.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. In addition, all publications cited herein are indicative of the level of skill in the art and are hereby incorporated by reference in their entirety as if each had been individually incorporated by reference and fully set forth.

What is claimed is:

1. A composition of matter comprising a carbonizable polymeric aerogel incorporating ferrocene in every repeating unit, wherein said polymeric aerogel comprises the following repeating units:

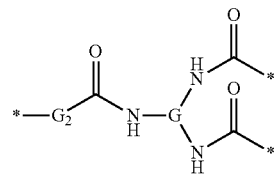

wherein:
G represents a group selected from aryl, (aryl)-R-(aryl), and (aryl)-R-(aryl)$_2$; where each aryl independently represents an optionally substituted aromatic ring; and where R is a bond or a $C_1$-$C_6$ straight chain or branched chain alkyl group;
$G_2$ represents a ferrocenyl moiety;
(*) denotes a linkage point; and
wherein the polymeric aerogel includes a mixture of polyamide and polyurea.

2. The polymeric aerogel of claim 1 wherein G is a triphenylmethane group of the following formula:

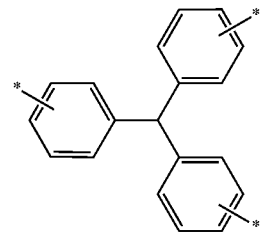

where the (*)s denote the linkage points on the linking bonds; and
where the linking bonds may be independently attached on their respective phenyl rings at the 2-position, 3-position or 4-position.

3. A process for carbonizing a carbonizable polymeric aerogel incorporating ferrocene in every repeating unit, wherein said polymeric aerogel comprises the following repeating units:

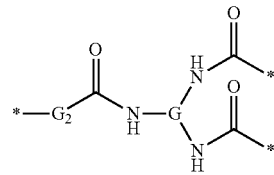

wherein:
G represents a group selected from awl, (aryl)-R-(aryl), and (aryl)-R-(aryl)$_2$; where each aryl independently represents an optionally substituted aromatic ring; and where R is a bond or a $C_1$-$C_6$ straight chain or branched chain alkyl group;

$G_2$ represents a ferrocenyl moiety;

(*) denotes a linkage point; and, wherein the polymeric aerogel includes a mixture of polyamide and polyurea;

said process comprising the step of pyrolizing the polymeric aerogel at temperatures in the range 500-2300° C. to yield a nanoporous product that includes iron-doped carbon-monoliths containing Fe(0) nanoparticles in graphitic pockets dispersed throughout the 3D matrix of monolithic nanoporous carbon.

4. A process for partially or completely transmetalating the iron-doped carbon-monoliths of claim 3 to produce M-doped carbon monoliths, wherein M is one or more metals selected from the group of metals consisting of Fe, Au, Pt, Pd, Co, Ni, Ru, and Rh, said process comprising the step of dipping the iron-doped carbon monoliths in solutions of the respective metal ions.

5. The process of claim 4, further including the step of subjecting the solutions of the respective metal ions to galvanic conditions.

6. A composition of matter comprising M-doped carbon monoliths obtained by the following process steps:
(a) carbonizing a polymeric aerogel incorporating ferrocene in every repeating unit by pyrolizing said polymeric aerogel at temperatures in the range 500-2300° C. to yield a nanoporous product that includes iron-doped carbon-monoliths containing Fe(0) nanoparticles in graphitic pockets dispersed throughout a 3D matrix of monolithic nanoporous carbon; and,
(b) partially or completely transmetalating the iron-doped carbon-monoliths by dipping the nanoporous product that includes the iron-doped carbon monoliths in solutions of metal ions to produce the M-doped carbon monoliths;

wherein M is one or more metals selected from the group of metals consisting of Fe, Au, Pt, Pd, Co, Ni, Ru, and Rh;

wherein said polymeric aerogel comprises the following repeating units:

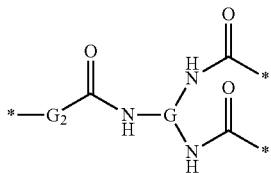

wherein:
G represents a group selected from aryl, (aryl)-R-(aryl), and (aryl)-R-(aryl)$_2$; where each aryl independently represents an optionally substituted aromatic ring; and where R is a bond or a $C_1$-$C_6$ straight chain or branched chain alkyl group;

$G_2$ represents a ferrocenyl moiety;

(*) denotes a linkage point and, wherein the polymeric aerogel includes a mixture of polyamide and polyurea.

7. The composition of claim 6 wherein the composition includes at least 50% v/v porous materials consisting of at least 50% w/w of carbon.

8. The composition of claim 7, wherein the carbon includes a substantial amount of disordered graphite, and contains in dispersed form nanoparticles of metal M in a w/w ratio of from about 1% to about 50%.

9. A method of catalysis of a chemical reaction in a mixture, the method comprising the step of contacting the mixture with a catalytic amount of a composition of matter comprising M-doped carbon monoliths obtained by the following steps:
(a) carbonizing a polymeric aerogel incorporating ferrocene in every repeating unit by pyrolizing said polymeric aerogel at temperatures in the range 500-2300° C. to yield a nanoporous product that includes iron-doped carbon-monoliths containing Fe(0) nanoparticles in graphitic pockets dispersed throughout a 3D matrix of monolithic nanoporous carbon; and,
(b) partially or completely transmetalating the iron-doped carbon-monoliths by dipping the nanoporous product that includes the iron-doped carbon monoliths in solutions of metal ions to produce the M-doped carbon monoliths;

wherein M is one or more metals selected from the group of metals consisting of Fe, Au, Pt, Pd, Co, Ni, Ru, and Rh; and, wherein said polymeric aerogel comprises the following repeating units:

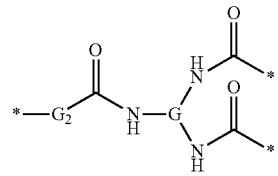

wherein:
G represents a group selected from awl, (aryl)-R-(aryl), and (aryl)-R-(aryl)$_2$; where each aryl independently represents an optionally substituted aromatic ring; and where R is a bond or a $C_1$-$C_6$ straight chain or branched chain alkyl group;

$G_2$ represents a ferrocenyl moiety;

(*) denotes a linkage point and, wherein the polymeric aerogel includes a mixture of polyamide and polyurea.

10. The method of claim 9, wherein the chemical reaction is selected from the group consisting of reduction of a nitro compound, oxidation of an alcohol, and a Heck coupling reaction.

* * * * *

UNITED STATES PATENT AND TRADEMARK OFFICE
CERTIFICATE OF CORRECTION

| | | |
|---|---|---|
| PATENT NO. | : 9,593,225 B2 | Page 1 of 1 |
| APPLICATION NO. | : 14/969650 | |
| DATED | : March 14, 2017 | |
| INVENTOR(S) | : Nicholas Leventis et al. | |

It is certified that error appears in the above-identified patent and that said Letters Patent is hereby corrected as shown below:

In the Claims

Column 61, Claim 3, Line 2, please delete "awl" and insert --aryl--.

Column 62, Claim 9, Line 46, please delete "awl" and insert --aryl--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*